US006277823B1

United States Patent
Kramer et al.

(12)

(10) Patent No.: US 6,277,823 B1
(45) Date of Patent: Aug. 21, 2001

(54) INSECTICIDAL TOXINS AND NUCLEIC ACID SEQUENCES CODING THEREFOR

(75) Inventors: Vance Cary Kramer, Hillsborough; Michael Kent Morgan, Durham; Arne Robert Anderson, Zebulon, all of NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/668,648

(22) Filed: Sep. 22, 2000

Related U.S. Application Data

(62) Division of application No. 09/293,395, filed on Apr. 16, 1999, now Pat. No. 6,174,860.
(60) Provisional application No. 60/145,748, filed on Apr. 21, 1998, provisional application No. 60/123,500, filed on Mar. 9, 1999, and provisional application No. 60/125,525, filed on Mar. 22, 1999.

(51) Int. Cl.[7] .................................................. A16K 38/00
(52) U.S. Cl. ......................... 514/12; 43/132.1; 424/405; 536/23.7
(58) Field of Search .......................... 43/132.1; 424/405; 514/12; 536/23.7

(56) References Cited

U.S. PATENT DOCUMENTS 5,972,687 * 10/1999 Smigielski et al. ............... 435/252.3

FOREIGN PATENT DOCUMENTS

| WO 93/03154 | 7/1992 | (WO) . |
| WO 95/00647 | 1/1995 | (WO) . |
| WO 96/38547 | 5/1996 | (WO) . |
| WO 97/17432 | 5/1997 | (WO) . |
| WO 98/08388 | 3/1998 | (WO) . |
| WO 98/08932 | 3/1998 | (WO) . |
| WO 99/03328 | 1/1999 | (WO) . |

OTHER PUBLICATIONS

Bintrim, S.B., Dissertation entitled, "A Study of the Crystalline Inclusion Proteins of *Photorhabdus luminescens*" (1994).

Bowen, D.J., Dissertation entitled, "Characterization of a high molecular weight insecticidal protein complex produced by the entomopathogenic bacterum *Photorhabdus liminescens*" (1995).
Forst et al., "Molecular Biology of the Symbiotic–Pathogenic Bacteria *Xenorhabdus* spp. and *Photorhabdus* spp.", *Microbiological Reviews* 60(1): 21–43 (Mar. 1996).
Forst et al., "*Xenorhabdus* and *Photorhabdus* SSP.: Bugs That Kill Bugs", *Annu. Rev Microbiol,.* 51: 47–72 (1997).
Hammock et al., "Expression and effects of the juvenile hormone esterase in a baculovirus vector", *Nature* 344: 458–461 (1990).
Vermunt et al., "Cloning and Sequence Analysis of cDNA Encoding a Putative Juvenile Hormone Esterase from the Colorado Potato Beetle", *Insect Biochem. Molec. Biol.* 27(11):919–928 (1997).
Stemmer, Nature, 370:389–391 (1994).
Bowen et al., Science, 280:2129–2132(1998).
Ivey et al. Accession U56090, Dec. 1, 1996.
Smith, A. Accession AC004083, 1/98.
Marra et al. Accession AA895852, 4/98.
Hillier et al. Accession T74981, 3/95.
Cho, Y. Accession X89403, 11/96.
Dante et al. Accession AC002066, 5/97.
Geisel et al. Accession AC002069, 5/97.
Pederson, B. Accession L26570, 2/96.
Hillier et al. Accession N99108.
Hudspeth et al. Accession X89403, 11/96.

* cited by examiner

*Primary Examiner*—Nashaat T. Nashed
*Assistant Examiner*—Christian L. Fronda
(74) *Attorney, Agent, or Firm*—J. Timothy Meigs; Jennifer L. Holmes; Larry W. Stults

(57) ABSTRACT

Novel nucleic acid sequences isolated from *Xenorhabdus nematophilus, Xenorhabdus poinarii,* and *Photorhabdus luminescens,* whose expression results in novel insecticidal toxins, are disclosed herein. The invention also discloses compositions and formulations containing the insecticidal toxins that are capable of controlling insect pests. The invention is further drawn to methods of making the toxins and to methods of using the nucleotide sequences, for example in microorganisms to control insect pests or in transgenic plants to confer insect resistance.

13 Claims, No Drawings

US 6,277,823 B1

INSECTICIDAL TOXINS AND NUCLEIC ACID SEQUENCES CODING THEREFOR

This application is a division of U.S. application Ser. No. 09/293,395, filed Apr. 16, 1999, U.S. Pat. No. 6,174,860, which claims the benefit of U.S. Provisional Application No. 60/154,748, filed Apr. 21, 1998; U.S. Provisional Application No. 60/123,500, filed Mar. 9, 1999; and U.S. Provisional Application No. 60/125,525, filed Mar. 22, 1999. The disclosure of each the aforementioned applications is hereby expressly incorporated by reference in its entirety into the instant disclosure.

FIELD OF THE INVENTION

The invention relates to novel toxins from *Xenorhabdus nematophilus*, *Xenorhabdus poinarii*, and *Photorhabdus luminescens*, nucleic acid sequences whose expression results in said toxins, and methods of making and methods of using the toxins and corresponding nucleic acid sequences to control insects.

BACKGROUND OF THE INVENTION

Insect pests are a major cause of crop losses. Solely in the US, about $7.7 billion are lost every year due to infestation by various genera of insects. In addition to losses in field crops, insect pests are also a burden to vegetable and fruit growers, to producers of ornamental flowers, and they are a nuisance to gardeners and home owners.

Insect pests are mainly controlled by intensive applications of chemical insecticides, which are active through inhibition of insect growth, prevention of insect feeding or reproduction, or death of the insects. Good insect control can thus be reached, but these chemicals can sometimes also affect other, beneficial insects. Another problem resulting from the wide use of chemical pesticides is the appearance of resistant insect varieties. This has been partially alleviated by various resistance management strategies, but there is an increasing need for alternative pest control agents. Biological insect control agents, such as *Bacillus thuringiensis* strains expressing insecticidal toxins like δ-endotoxins, have also been applied with satisfactory results, offering an alternative or a complement to chemical insecticides. Recently, the genes coding for some of these δ-endotoxins have been isolated and their expression in heterologous hosts have been shown to provide another tool for the control of economically important insect pests. In particular, the expression of insecticidal toxins in transgenic plants, such as *Bacillus thuringiensis* δ-endotoxins, has provided efficient protection against selected insect pests, and transgenic plants expressing such toxins have been commercialized, allowing farmers to reduce applications of chemical insect control agents. Yet, even in this case, the development of resistance remains a possibility and only a few specific insect pests are controllable. Consequently, there remains a long-felt but unfulfilled need to discover new and effective insect control agents that provide an economic benefit to farmers and that are environmentally acceptable.

SUMMARY OF THE INVENTION

The present invention addresses the long-standing need for novel insect control agents. Particularly needed are control agents that are targeted to economically important insect pests and that efficiently control insect strains resistant to existing insect control agents. Furthermore, agents whose application minimizes the burden on the environment are desirable.

In the search for novel insect control agents, certain classes of nematodes from the genera Heterorhabdus and Steinemema are of particular interest because of their insecticidal properties. They kill insect larvae and their offspring feed in the dead larvae. Indeed, the insecticidal activity is due to symbiotic bacteria living in the nematodes. These symbiotic bacteria are Photorhabdus in the case of Heterorhabdus and Xenorhabdus in the case of Steinemema.

The present invention is drawn to nucleotide sequences isolated from *Xenorhabdus nematophilus*, and nucleotide sequences substantially similar thereto, whose expression result in insecticidal toxins that are highly toxic to economically important pests, particularly plant pests. The invention is further drawn to the insecticidal toxin resulting from the expression of the nucleotide sequence, and to compositions and formulations containing the insecticidal toxin, that are capable of inhibiting the ability of insect pests to survive, grow or reproduce, or of limiting insect-related damage or loss in crop plants. The invention is further drawn to a method of making the toxin and to methods of using the nucleotide sequence, for example in microorganisms to control insects or in transgenic plants to confer insect resistance, and to a method of using the toxin, and compositions and formulations comprising the toxin, for example applying the toxin, composition or formulation to insect infested areas, or to prophylactically treat insect susceptible areas or plants to confer protection or resistance against harmful insects.

The novel toxin is highly insecticidal against *Plutella xylostella* (diamondback moth), an economically important insect pest. The toxin can be used in multiple insect control strategies, resulting in maximal efficiency with minimal impact on the environment.

According to one aspect, the present invention provides an isolated nucleic acid molecule comprising: (a) a nucleotide sequence substantially similar to a nucleotide sequence selected from the group consisting of: nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14; or (b) a nucleotide sequence isocoding with the nucleotide sequence of (a); wherein expression of said nucleic acid molecule results in at least one toxin that is active against insects. In one embodiment of this aspect, the nucleotide sequence is isocoding with a nucleotide sequence substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. Preferably, the nucleotide sequence is substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. More preferably, the nucleotide sequence encodes an amino acid sequence selected from the group consisting of SEQ ID NOs:2, 3, 5, 7, 9, 11, 13, and 15. Most preferably, the nucleotide sequence comprises nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. In another embodiment, the nucleotide sequence comprises the approximately 3.0 kb DNA fragment comprised in pCIB9369 (NRRL B-21883).

According to a preferred embodiment, the toxins resulting from expression of the nucleic acid molecules of the invention have activity against *Plutella xylostella*.

In another aspect, the present invention provides an isolated nucleic acid molecule comprising a 20, 25, 30, 35, 40, 45, or 50 (preferably 20) base pair nucleotide portion identical in sequence to a respective consecutive 20, 25, 30, 35, 40, 45, or 50 (preferably 20) base pair nucleotide portion of a nucleotide sequence selected from the group consisting of: nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14, wherein expression of said nucleic acid molecule results in at least one toxin that is active against insects.

The present invention also provides a chimeric gene comprising a heterologous promoter sequence operatively linked to a nucleic acid molecule of the invention. Further, the present invention provides a recombinant vector comprising such a chimeric gene. Still further, the present invention provides a host cell comprising such a chimeric gene. A host cell according to this aspect of the invention may be a bacterial cell, a yeast cell, or a plant cell, preferably a plant cell. Even further, the present invention provides a plant comprising such a plant cell. Preferably, the plant is maize.

In yet another aspect, the present invention provides toxins produced by the expression of DNA molecules of the present invention. According to a preferred embodiment, the toxins of the invention have activity against *Plutella xylostella*.

In one embodiment, the toxins are produced by the *E. coli* strain designated as NRRL accession number B-21883.

In another embodiment, a toxin of the invention comprises an amino acid sequence selected from the group consisting of: SEQ ID NOs:2, 3, 5, 7, 9, 11, 13, and 15.

The present invention also provides a composition comprising an insecticidally effective amount of a toxin according to the invention.

In another aspect, the present invention provides a method of producing a toxin that is active against insects, comprising: (a) obtaining a host cell comprising a chimeric gene, which itself comprises a heterologous promoter sequence operatively linked to the nucleic acid molecule of the invention; and (b) expressing the nucleic acid molecule in the cell, which results in at least one toxin that is active against insects.

In a further aspect, the present invention provides a method of producing an insect-resistant plant, comprising introducing a nucleic acid molecule of the invention into the plant, wherein the nucleic acid molecule is expressible in the plant in an effective amount to control insects. According to a preferred embodiment, the insects are *Plutella xylostella*.

In a still further aspect, the present invention provides a method of controlling insects comprising delivering to the insects an effective amount of a toxin according to the present invention. According to a preferred embodiment, the insects are *Plutella xylostella*. Preferably, the toxin is delivered to the insects orally.

Yet another aspect of the present invention is the provision of a method for mutagenizing a nucleic acid molecule according to the present invention, wherein the nucleic acid molecule has been cleaved into population of double-stranded random fragments of a desired size, comprising: (a) adding to the population of double-stranded random fragments one or more single- or double-stranded oligonucleotides, wherein the oligonucleotides each comprise an area of identity and an area of heterology to a double-stranded template polynucleotide; (b) denaturing the resultant mixture of double-stranded random fragments and oligonucleotides into single-stranded fragments; (c) incubating the resultant population of single-stranded fragments with a polymerase under conditions which result in the annealing of the single-stranded fragments at the areas of identity to form pairs of annealed fragments, the areas of identity being sufficient for one member of a pair to prime replication of the other, thereby forming a mutagenized double-stranded polynucleotide; and (d) repeating the second and third steps for at least two further cycles, wherein the resultant mixture in the second step of a further cycle includes the mutagenized double-stranded polynucleotide from the third step of the previous cycle, and wherein the further cycle forms a further mutagenized double-stranded polynucleotide.

Other aspects and advantages of the present invention will become apparent to those skilled in the art from a study of the following description of the invention and non-limiting examples.

DEFINITIONS

"Activity" of the toxins of the invention is meant that the toxins function as orally active insect control agents, have a toxic effect, or are able to disrupt or deter insect feeding, which may or may not cause death of the insect. When a toxin of the invention is delivered to the insect, the result is typically death of the insect, or the insect does not feed upon the source that makes the toxin available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

A "nucleic acid molecule" or "nucleic acid sequence" is a linear segment of single- or double-stranded DNA or RNA that can be isolated from any source. In the context of the present invention, the nucleic acid molecule is preferably a segment of DNA. "ORF" means open reading frame.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90%, more preferably at least 95%, still more preferably at least 99%. A nucleotide sequence "substantially similar" to reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gin; Q), glutamic acid (Glu; E), glycine (Gly; G), histidine (His; H), isoleucine (Iie; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

BRIEF DESCRIPTION OF THE SEQUENCES IN THE SEQUENCE LISTING

SEQ ID NO:1 is the sequence of the approximately 3.0 kb DNA fragment comprised in *Xenorhabdus nematophilus* clone pCIB9369, which comprises the following ORFs at the specified nucleotide positions:

| Name | Start | End |
| --- | --- | --- |
| orf1 | 569 | 979 |
| orf2 | 1045 | 2334 |

SEQ ID NO:2 is the sequence of the ~15 kDa protein encoded by orf1 of clone pCIB9369.
SEQ ID NO:3 is the sequence of the ~47.7 kDa Juvenile Hormone Esterase-like protein encoded by orf2 of clone pCIB9369.
SEQ ID NO:4 is the DNA sequence of orf1 of *Xenorhabdus nematophilus* clone pCIB9381.
SEQ ID NO:5 is the sequence of the protein encoded by orf1 of clone pCIB9381.
SEQ ID NO:6 is the DNA sequence of orf2 of *Xenorhabdus nematophilus* clone pCIB9381.
SEQ ID NO:7 is the sequence of the Juvenile Hormone Esterase-like protein encoded by orf2 of clone pCIB9381.
SEQ ID NO:8 is the DNA sequence of orf1 of *Xenorhabdus poinarii* clone pCIB9354.
SEQ ID NO:9 is the sequence of the protein encoded by orf1 of clone pCIB9354.
SEQ ID NO:10 is the DNA sequence of orf2 of *Xenorhabdus poinarii* clone pCIB9354.
SEQ ID NO:11 is the sequence of the Juvenile Hormone Esterase-like protein encoded by orf2 of clone pCIB9354.
SEQ ID NO:12 is the DNA sequence of orf1 of *Photorhabdus luminescens* clone pCIB9383-21.
SEQ ID NO:13 is the sequence of the protein encoded by orf1 of clone pCIB9383-21.
SEQ ID NO:14 is the DNA sequence of orf2 of *Photorhabdus luminescens* clone pCIB9383-21.
SEQ ID NO:15 is the sequence of the Juvenile Hormone Esterase-like protein encoded by orf2 of clone pCIB9383-21.

DEPOSITS

The following material has been deposited with the Agricultural Research Service, Patent Culture Collection (NRRL), 1815 North University Street, Peoria, Ill. 61604, under the terms of the Budapest Treaty on the International Recognition of the Deposit of Microorganisms for the Purposes of Patent Procedure. All restrictions on the availability of the deposited material will be irrevocably removed upon the granting of a patent.

| Clone | Accession Number | Date of Deposit |
| --- | --- | --- |
| pCIB9369 | NRRL B-21883 | November 12, 1997 |
| pCIB9354 | NRRL B-30109 | February 25, 1999 |
| pCIB9381 | NRRL B-30110 | February 25, 1999 |
| pCIB9383-21 | NRRL B-30111 | February 25, 1999 |

DETAILED DESCRIPTION OF THE INVENTION

Novel Nucleic Acid Sequences whose Expression Results in Insecticidal Toxins

This invention relates to nucleic acid sequences whose expression results in novel toxins, and to the making and using of the toxins to control insect pests. The nucleic acid sequences are isolated from *Xenorhabdus nematophilus*, *Xenorhabdus poinarii*, and *Photorhabdus luminescens*, members of the Enterobacteriaceae family. Xenorhabdus are symbiotic bacteria of nematodes of the genus Steinernema. Photorhabdus are symbiotic bacteria of nematodes of the genus Heterorhabditis. The nematodes colonize insect larva, kill them, and their offspring feed on the dead larvae. The insecticidal activity is actually produced by the symbiotic Xenorhabdus and Photorhabdus bacteria. The inventors are the first to isolate the nucleic acid sequences of the present invention. The expression of the nucleic acid sequences of the present invention results in toxins that can be used to control Lepidopteran insects such as *Plutella xylostella* (Diamondback Moth).

A nucleotide sequence of the present invention in clone pCIB9369 is characterized by an approximately 3.0 kb DNA fragment deposited pursuant to the Budapest Treaty for Patent Deposits under Accession Number NRRL B-21883. The sequence of this DNA fragment is set forth in SEQ ID NO:1. Two open reading frames (ORF) are present in SEQ ID NO:1 (nucleotides 569–979 and nucleotides 1045–2334, respectively), coding for proteins of predicted sizes of 15 kDa and 47.7 kDa (SEQ ID NOs:2 and 3, respectively). The two ORFs are arranged in an operon-like structure. A search for known sequences showing homology to each individual ORF using the UWGCG Blast and Gap programs does not reveal any significant match for ORF #1 and reveals 21% identity between ORF #2 and *Bacillus thuringensis* cry3A protein, which is not considered to be significant in the art. A Gap analysis of the protein encoded by ORF #2 of pCIB9369 by the Blast program identifies 30.6% AA identity and 44.1% AA similarity to a juvenile hormone esterase-related protein (GenBank accession 2921553; Henikoff et al., *PNAS USA* 89: 10915–10919 (1992)). The nucleotide sequence of the present invention is also compared to known *Xenorhabdus nematophilus* sequences encoding the insecticidal toxin toxb4 (WO 95/00647), but no significant homology is found. The 3.0 kb DNA fragment is also compared to the nucleotide sequence published in WO 98/08388. Twenty-two sequences of 60 nucleotides each (60-mers) from the 38.2 kb DNA fragment described in WO 98/08388 are compared to the 3.0 kb DNA fragment of the present invention using the UWGCG Gap program. The nucleotide sequence of the first 60-mer starts at base 1 of the 38.2 kb DNA fragment and the other 60-mers are located at approximately 2.0 kb intervals. Each of the 22 sequences as well as their complementary sequences are tested. The highest percent of identity between the 3.0 kb DNA fragment of the present invention and one of these 60-mers is 53%, which is not a significant homology. Furthermore, five different DNA fragments of the 38.2 kb sequence are tested for hybridization to the 3.0 kb fragment of the present invention by Southern blot analysis. None of them reveal a positive hybridization signal.

The nucleotide sequences of pCIB9381, pCIB9354, and pCIB9383-21 also reveal two open reading frames in each of these clones. The nucleotide sequences of the two ORFs in each of pCIB9381 and pCIB9383-21 are highly homologous to those in pCIB9369. Hence, the ORF #2 proteins of pCIB9381 and pCIB9383-21 have essentially the same homology to the juvenile hormone esterase-related protein as does the ORF #2 protein of pCIB9369. The nucleotide sequence of ORF #1 of pCIB9354 is 77% identical to the nucleotide sequence of ORF #1 of pCIB9369, and the nucleotide sequence of ORF #2 of pCIB9354 is 79% identical to the nucleotide sequence of ORF #2 of pCiB9369. The ORF #2 protein of pCIB9354 also has homology to the juvenile hormone esterase-related protein (29.2% AA identity and 42.2% AA similarity).

In a preferred embodiment, the invention encompasses a nucleotide sequence substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14, whose expression results in an insecticidal toxin. The present invention also encompasses recombinant vectors comprising the nucleic acid sequences of this invention. In such vectors, the nucleic acid sequences are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In one embodiment, host cells for such vectors are microorganisms, such as bacteria, in particular *E. coli*. In another embodiment, host cells for such recombinant vectors are endophytes or epiphytes. A preferred host cell for such vectors is a eukaryotic cell, such as a yeast, a plant cell, or an insect cell. Plant cells such as maize cells are most preferred host cells. In another preferred embodiment, such vectors are viral vectors and are used for replication of the nucleotide sequences in particular host cells, e.g. insect cells or plant cells. Recombinant vectors are also used for transformation of the nucleotide sequences of this invention into host cells, whereby the nucleotide sequences are stably integrated into the DNA of such host cells. In one, such host cells are prokaryotic cells. In a preferred embodiment, such host cells are eukaryotic cells, such as yeast cells, insect cells, or plant cells. In a most preferred embodiment, the host cells are plant cells, such as maize cells.

The nucleotide sequences of the invention can be isolated using the techniques described in the examples below, or by PCR using the sequences set forth in the sequence listing as the basis for constructing PCR primers. For example, oligonucleotides having the sequence of approximately the first and last 20–25 consecutive nucleotides of orf1 of SEQ ID NO:1 (e.g., nucleotides 569–588 and 957–976 of SEQ ID NO:1) can be used as PCR primers to amplify the orf1 coding sequence (nucleotides 569–976 of SEQ ID NO:1) directly from the source strain (*Xenorhabdus nematophilus* strain ATCC 19061). The other gene sequences of the invention can likewise be amplified by PCR from the respective source strains using the ends of the coding sequences set forth in the sequence listing as the basis for PCR primers.

In another preferred embodiment, the insecticidal toxins comprise at least one polypeptide encoded by a nucleotide sequence of the invention. The molecular weight of an insecticidal toxin according to the invention is larger than 6,000, as determined by size fractionation experiments. After treatment with proteinase K, only a minimal decrease in insecticidal activity is observed in the insect bioassay, indicating that the insecticidal toxins are substantially resistant to proteinase K treatment. The insecticidal toxins retain their insecticidal activity after being stored at 22° C. or at 4° C. for 2 weeks. They also retains their insecticidal activity after being freeze dried and stored at 22° C. for 2 weeks. The insecticidal toxins are also still active after incubation for 5 minutes at 60° C., but they loses their insecticidal activity after incubation for 5 minutes at 100° C. or 80° C.

In further embodiments, the nucleotide sequences of the invention can be modified by incorporation of random mutations in a technique known as in-vitro recombination or DNA shuffling. This technique is described in Stemmer et al., Nature 370: 389–391 (1994) and U.S. Pat. No. 5,605,793, which are incorporated herein by reference. Millions of mutant copies of a nucleotide sequence are produced based on an original nucleotide sequence of this invention and variants with improved properties, such as increased insecticidal activity, enhanced stability, or different specificity or range of target insect pests are recovered. The method encompasses forming a mutagenized double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles.

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, *Xenorhabdus nematophilus, Xenorhabdus poinarii*, or *Photorhabdus luminescens* cells comprising modifications of at least one nucleotide sequence of this invention at its chromosomal location are described. Such modifications encompass mutations or deletions of existing regulatory elements, thus leading to altered expression of the nucleotide sequence, or the incorporation of new regulatory elements controlling the expression of the nucleotide sequence. In another embodiment, additional copies of one or more of the nucleotide sequences are added to *Xenorhabdus nematophilus, Xenorhabdus poinarii*, or *Photorhabdus luminescens* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in-vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces and Xanthomonas. Symbiotic fungi, such as Trichoderma and Gliocladium are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely for example, on yeast vectors and include the use of Pichia, Saccharomyces and Kluyveromyces (Sreekrishna, In: Industrial microorganisms: basic and applied molecular genetics, Baltz, Hegeman, and Skatrud eds., American Society for Microbiology, Washington (1993); Dequin & Barre, Biotechnology 12:173–177 (1994); van den Berg et al., Biotechnology 8:135–139 (1990)).

In another preferred embodiment, at least one of the described nucleotide sequences is transferred to and expressed in Pseudomonas fluorescens strain CGA267356 (described in the published application EU 0 472 494 and in WO 94/01561) which has biocontrol characteristics. In another preferred embodiment, a nucleotide sequence of the invention is transferred to *Pseudomonas aureofaciens* strain 30-84 which also has biocontrol characteristics. Expression in heterologous biocontrol strains requires the selection of vectors appropriate for replication in the chosen host and a suitable choice of promoter. Techniques are well known in the art for expression in gram-negative and gram-positive bacteria and fungi.

Expression of the Nucleotide Sequences in Plant Tissue

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, Arabidopsis, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least 35% about GC content, preferably more than about 45%, more preferably more than about 50%, and most preferably more than about 60%. Microbial nucleotide sequences which have low GC contents may express poorly in plants due to the existence of ATTTA motifs which may destabilize messages, and AATAAA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy).

For efficient initiation of translation, sequences adjacent to the initiating methionine may require modification. For example, they can be modified by the inclusion of sequences known to be effective in plants. Joshi has suggested an appropriate consensus for plants (NAR 15: 6643–6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters shown to be functional in plants. The choice of promoter will vary depending on the temporal and spatial requirements for expression, and also depending on the target species. Thus, expression of the nucleotide sequences of this invention in leaves, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expressiori in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CaMV 35S and 19S promoters. The nucleotide sequences of this invention can also be expressed under the regulation of promoters that are chemically regulated. This enables the insecticidal toxins to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells which need to synthesize the insecticidal toxins to kill the invading insect pest. Preferred promoters of this kind include those described by Stanford et al. Mol. Gen. Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12: 579–589 (1989)). A preferred promoter for root specific expression is that described by de Framond (FEBS 290: 103–106 (1991); EP 0 452 269 to Ciba-Geigy). A preferred stem specific promoter is that described in U.S. Pat. No. 5,625,136 (to Ciba-Geigy) and which drives expression of the maize trpA gene.

Especially preferred embodiments of the invention are transgenic plants expressing at least one of the nucleotide sequences of the invention in a root-preferred or root-specific fashion. Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tm1 from CaMV, E9 from rbcS). Any available terminator known to function in plants can be used in the context of this invention.

Numerous other sequences can be incorporated into expression cassettes described in this invention. These include sequences which have been shown to enhance expression such as intron sequences (e.g. from Adh1 and bronze1) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093–1096 (1986)). For both direct gene transfer and Agrobacterium-mediated transfer, transformation is usually (but not necessarily) undertaken with a selectable marker which may provide resistance to an antibiotic (kanamycin, hygromycin or methotrexate) or a herbicide (basta). Examples of such markers are neomycin phosphotransferase, hygromycin phosphotransferase, dihydrofolate reductase, phosphinothricin acetyltransferase, 2,2-dichloroproprionic acid dehalogenase, acetohydroxyacid synthase, 5-enolpyruvyl-shikimate-phosphate synthase, haloarylnitrilase, protoporhyrinogen oxidase, acetyl-coenzyme A carboxylase, dihydropteroate synthase, chloramphenicol acetyl transferase, and β-glucuronidase. The choice of selectable or screenable marker for plant transformation is not, however, critical to the invention.

The recombinant DNA described above can be introduced into the plant cell in a number of art-recognized ways. Those skilled in the art will appreciate that the choice of method might depend on the type of plant targeted for transformation. Suitable methods of transforming plant cells include microinjection (Crossway et al., BioTechniques 4:320–334 (1986)), electroporation (Riggs et al., *Proc. Natl. Acad. Sci. USA* 83:5602–5606 (1986), Agrobacterium-mediated transformation (Hinchee et al., *Biotechnology* 6:915–921 (1988); See also, Ishida et al., *Nature Biotechnology* 14:745–750 (June 1996) for maize transformation), direct gene transfer (Paszkowski et al., *EMBO J.* 3:2717–2722 (1984); Hayashimoto et al., *Plant Physiol* 93:857–863 (1990)(rice)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6:923–926 (1988)). See also, Weissinger et al., *Annual Rev. Genet.* 22:421–477 (1988); Sanford et al., *Particulate Science and Technology* 5.27–37 91987)(onion); Svab et al., *Proc. Natl. Acad. Sci. USA* 87:8526–8530 (1990) (tobacco chloroplast); Christou et al., *Plant Physiol.* 87:671–674 (1988)(soybean); McCabe et al., *Bio/Technology* 6.923–926 (1988)(soybean); Klein et al., *Proc. Natl. Acad. Sci. USA,* 85:4305–4309 (1988)(maize); Klein et al., *Bio/Technology* 6:559–563 (1988) (maize); Klein et al., *Plant Physiol.* 91:440–444 (1988) (maize); Fromm et al., *Bio/Technology* 8:833–839 (1990); and Gordon-Kamm et al., *Plant Cell* 2: 603–618 (1990) (maize); Koziel et al., *Biotechnology* 11: 194–200 (1993) (maize); Shimamoto et al., *Nature* 338: 274–277 (1989) (rice); Christou et al., *Biotechnology* 9: 957–962 (1991) (rice); Datta et al., *Biol/Technology* 3:736–740 (1990) (rice); European Patent Application EP 0 332 581 (orchardgrass and other Pooideae); Vasil et al., *Biotechnology* 11: 1553–1558 (1993) (wheat); Weeks et al., *Plant Physiol.* 102: 1077–1084 (1993) (wheat); Wan et al., *Plant Physiol.* 104: 37–48 (1994) (barley); Jahne et al., *Theor. Appl. Genet.* 89:525–533 (1994)(barley); Umbeck et al., *Bio/Technology* 5: 263–266 (1987) (cotton); Casas et al., *Proc. Natl. Acad. Sci. USA* 90:11212–11216 (December 1993) (sorghum); Somers et al., *Bio/Technology* 10:1589–1594 (December 1992) (oat); Torbert et al., *Plant Cell Reports* 14:635–640 (1995) (oat); Weeks et al., *Plant Physiol.* 102:1077–1084 (1993) (wheat); Chang et al., WO 94/13822 (wheat) and Nehra et al., *The Plant Journal* 5:285–297 (1994) (wheat). A particularly preferred set of embodiments for the introduction of recombinant DNA molecules into maize by microprojectile bombardment can be found in Koziel et al., *Biotechnology* 11: 194–200 (1993), Hill et al., *Euphytica* 85:119–123 (1995) and Koziel et al., *Annals of the New York Academy of Sciences* 792:164–171 (1996). An additional preferred embodiment is the protoplast transformation method for maize as disclosed in EP 0 292 435. Transformation of plants can be undertaken with a single DNA species or multiple DNA species (i.e. co-transformation) and both these techniques are suitable for use with the peroxidase coding sequence.

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) *EMBO J.* 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913–917). Previously, this marker had been used successfully for high-frequency transformation of the plastid genome of the green alga *Chlamydomonas reinhardtii* (Goldschmidt-Clermont, M. (1991) *Nucl. Acids Res.* 19: 4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

Formulation of Insecticidal Compositions

The invention also includes compositions comprising at least one of the insecticidal toxins of the present invention. In order to effectively control insect pests such compositions preferably contain sufficient amounts of toxin. Such amounts vary depending on the crop to be protected, on the particular pest to be targeted, and on the environmental conditions, such as humidity, temperature or type of soil. In a preferred embodiment, compositions comprising the insecticidal toxins comprise host cells expressing the toxins without additional purification. In another preferred embodiment, the cells expressing the insecticidal toxins are lyophilized prior to their use as an insecticidal agent. In another embodiment, the insecticidal toxins are engineered to be secreted from the host cells. In cases where purification of the toxins from the host cells in which they are expressed is desired, various degrees of purification of the insecticidal toxins are reached.

The present invention further embraces the preparation of compositions comprising at least one insecticidal toxin of the present invention, which is homogeneously mixed with one or more compounds or groups of compounds described herein. The present invention also relates to methods of treating plants, which comprise application of the insecticidal toxins or compositions containing the insecticidal toxins, to plants. The insecticidal toxins can be applied to the crop area in the form of compositions or plant to be treated, simultaneously or in succession, with further compounds. These compounds can be both fertilizers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying insecticidal toxins of the present invention is by spraying to the environment hosting the insect pest like the soil, water, or foliage of plants. The number of applications and the rate of application depend on the type and intensity of infestation by the insect pest. The insecticidal toxins can also penetrate the plant through the roots via the soil (systemic action) by impregnating the locus of the plant with a liquid composition, or by applying the compounds in solid form to the soil, e.g. in granular form (soil application). The insecticidal toxins may also be applied to seeds (coating) by impregnating the seeds either with a liquid formulation containing insecticidal toxins, or coating them with a solid formulation. In special cases, further types of application are also possible, for example, selective treatment of the plant stems or buds. The insecticidal toxins can also be provided as bait located above or below the ground.

The insecticidal toxins are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances.

The formulations, compositions or preparations containing the insecticidal toxins and, where appropriate, a solid or liquid adjuvant, are prepared in known manner, for example by homogeneously mixing and/or grinding the insecticidal toxins with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimdthyl formamide, as well as epoxidized vegetable oils such as epoxidized coconut oil or soybean oil or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Suitable surface-active compounds are nonionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutyinapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one C8–C22 alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

A. Isolation Of Nucleotide Sequences Whose Expression Results In Toxins Active Against Lepidopteran Insects Example 1

Growth of Xenorhabdus and Photorhabdus Strains

For insect bioassays, the following strains are grown in nutrient broth at 25° C. for 3 days in the growth media recommended by ATCC. For DNA isolation, the cultures are grown for 24 hr under the same conditions.

Xenorhabdus nematophilus strain ATCC 19061
Xenorhabdus nematophilus strain Ps1 (a USDA isolate)
Xenorhabdus poinarii strain ATCC 49122
Photorhabdus luminescens strain Ps5 (a USDA isolate)

Example 2

Insect Bioassay

Plutella xylostella (Px) bioassays are performed by aliquoting 50 µl of each E. coli culture on the solid artificial P. xylostella diet (Biever and Boldt, Annals of Entomological Society of America, 1971; Shelton, et al J. Ent. Sci 26:17). 4 ml of the diet is poured into 1 oz. clear plastic cups (Bioserve product #9051). 5 neonate P. xylostella from a diet adapted lab colony are placed in each diet containing cup and then covered with a white paper lid (Bioserve product #9049). 10 larvae are assayed per concentration. Trays of cups are placed in an incubator for 3 days at 72° F. with a 14:10 (hours) light: dark cycle. The number of live larvae in each cup is recorded.

Example 3

Results of Bioassays

The broth of Xenorhabdus nematophilus strain ATCC 19061 gives 100% mortality against Plutella xylostella (Px) in the insect bioassay of Example 2. Broth of each of Xenorhabdus nematophilus strain Ps1, Xenorhabdus poinarii strain ATCC 49122, and Photorhabdus luminescens strain Ps5, likewise gives 100% mortality against Plutella xylostella (Px) in the insect bioassay of Example 2.

Example 4

Construction of Cosmid Libraries

Total DNA is isolated from Xenorhabdus nematophilus strain ATCC 19061 by treating freshly grown cells resuspended in 100 mM Tris pH 8, 10 mM EDTA with 2 mg/ml lysozyme for 30 minutes at 37° C. Proteinase K is added to a final concentration of 100 µg/ml in 0.5% SDS and incubated at 45° C. The solution clears and becomes very viscous. The SDS concentration is increased to 1% and 300 mM NaCl and equal volume of phenol-chloroform-isoamyl alcohol are added. The sample is gently mixed for 5 minutes and centrifuged at 3K. This is repeated twice. The aqueous phase is then mixed with 0.7 volumes isopropanol and centrifuged. The DNA pellet is washed three times with 70% ethanol and gently resuspended in 0.5×XTE. 6 µg of DNA are treated with 0.3 unit of Sau3A per gg of DNA at 37° C. for 3.5 minutes in a volume of 100 µl. The sample is then heated for 30 minutes at 65° C. to inactivate the enzyme, then incubated with 2 units of calf intestinal alkaline phosphatase for 30 minutes at 37° C. The sample is mixed with an equal volume of phenol-chloroform-isoamyl alcohol and centrifuged. The aqueous phase is removed and mixed with 0.7 volumes isopropanol and centrifuged. The pellet is resuspended in 0.5×XTE at a concentration of 100 ng/ml.

SuperCos cosmid vector (Stratagene, La Jolla, Calif.) is prepared as described by the supplier utilizing the BamHI cloning site. Prepared SuperCos at 100 ηg/ml is ligated with the X. nematophilus DNA previously digested with Sau3A at a ratio of 2:1 in a 5 µl volume overnight at 6° C. The ligation mixture is packaged using Gigapack XL III (Stratagene) as described by the supplier. Packaged phages are infected into XL-1MR E. coli cells (Stratagene) as described by the supplier. The cosmid library is plated on L-agar with 50 µg/ml 'kanamycin and incubated 16 hours at 37° C. 500 colonies are patched to fresh L-kan plates at a density of 50/plate. The cells are washed off with L broth and mixed with 20% glycerol and frozen at −80° C.

In the case of the 4.2 Mb large genome of X. nematophilus, 450 clones with an average size of 40 Kb correspond to a 4-fold coverage of the genome. Therefore, screening of 450 clones should result in a 99% probability of finding any gene.

Cosmid libraries from Xenorhabdus nematophilus strain Ps1, Xenorhabdus poinarii strain ATCC 49122, and Photorhabdus luminescens strain Ps5 are constructed in a like manner.

Example 5

Results of the Cosmids Bioassays and Identification of Clones Having Insecticidal Activity 400 E. coli clones from each cosmid library are screened by insect bioassay yielding clones with activity against Plutella xylostella. An insecticidal cosmid clone from Xenorhabdus nematophilus strain ATCC 19061 is identified as pCIB9362. A 42 kb insecticidal cosmid clone from Xenorhabdus nematophilus strain Ps1 is identified as pCIB9379. A 42 kb insecticidal cosmid clone from Xenorhabdus poinarii strain ATCC 49122 is identified as pCIB9354. A 7 kb insecticidal cosmid clone from Photorhabdus luminescens strain Ps5 is identified as pCIB9383-21.

Example 6

Isolation of Subclones Having Insecticidal Activity

Clone pCIB9362 is digested with Sacll and a 9 kb DNA fragment is isolated. This fragment is ligated into Bluescript cut with Sacll. The ligation mixture is transformed into DH5α *E. coli* cells as described in Molecular Cloning, second edition (Sambrook et al.). The transformation mixture is plated on L agar plus 100 μg/ml ampillicin and incubated at 37° C. overnight. Isolated colonies are grown up in L broth with 100 μg/ml ampillicin and plasmid DNA isolated by alkaline minipreps as described in Molecular Cloning, second edition. The 9 kb Sacll clone is identified as pCIB9362-3 and gives 100% mortality when bioassayed against *Plutella xylostella.* 3 μg of pCIB9362-3 is isolated, digested with 0.3 unit of Sau3A per μg DNA for 4, 6 and 8 min. at 37° C. and heated at 75° C. for 15 min. Samples are pooled and ligated into pUC19 previously digested with BamHl and treated with calf intestinal alkaline phosphatase. The ligation is transformed into DH5α *E. coli* cells, plated on L agar with Xgal/Amp as described in Molecular Cloning and grown overnight at 37° C. White colonies are picked and grown up in L broth with 100 μg/ml ampicillin and plasmid DNA is isolated as previously described. DNA is digested with EcoRI/Hindlll and novel restriction patterns are sequenced. Sequencing primers are ordered from Genosys Biotechnologies (Woodlands, Tex.). Sequencing is performed using the dideoxy chain-termination method and is completed using Applied Biosystems Inc. model 377 automated DNA sequencer (Foster City, Calif.). The sequence is assembled using Sequencher 3.0 from Gene Codes Corporation (Ann Arbor, Mich.).

After identification of restriction sites and of potential ORF's, pCIB9362-3 is digested with Clal and a 3.0 kb fragment is isolated cloned into Bluescript and transformed into DH5α *E. coli* cells. The isolated colonies are grown as previously described and plasmid DNA isolated by the alkaline method. The subclone is identified as pCIB9369 and gives 100% mortality against *Plutella xylostella* in a bioassay. pCIB9369 has been deposited on Nov. 12, 1997 and identified by NRRL Number B-21883 at the USDA ARS Patent Culture Collection.

A 20 kb fragment identified as pCIB9381 is subcloned from cosmid pCIB9379 using a Notl digest.

Example 7

Bioassay Results

Insect Bioassays are conducted for pCIB9369 for a variety of insects.

| Insect | pCIB9369 |
|---|---|
| *Plutella xylostella* | +++ |
| *Hellothis virescens* | na |
| *Helioverpa zea* | na |
| *Spodoptera exguia* | na |
| C. elegans | na | na = not active
+ = significant growth inhibition
++ = >40% mortality, but less than 100%
+++ = 100% mortality These results show that the insecticidal toxin resulting from expression of the 3.0 kb nucleotide sequence in pCIB9369 is highly active against *Plutella xylostella.*

Bioassays for pCIB9381, pCIB9354, and pCIB9383-21 also show high insecticidal activity against *Plutella xylostella.*

Example 8

Size Fraction of the Insecticidal Activity

*Xenorhabdus nematophilus* cosmid clone pCIB9369 and Stratagene's Blue Script vector in *E. coli* host DH5 are grown in media consisting of 50% Terrific broth and 50% Luria broth, supplemented with 50 μg/ml of ampicilin. Shake flask cultures (300 ml in 1000 ml baffled flasks ) are grown at 250 RPM, overnight at 37° C. Cultures of each strain are centrifuged at 7,000 RPM in a Sorvall GS-3 rotor at 4° C. The pelleted cells are resuspended in 30 ml of 5 mM NaCl, 25 mM Tris base, pH 7.0. The concentrated cells are disrupted by sonication using a Branson Model 450 Sonicator for approximately eight 10 second cycles with cooling on ice between cycles. The sonicates are centrifuged in a Sorvall SS34 rotor at 6,000 RPM for 10 minutes at 4° C. The resultant supernatants are filtered through a 0.2 µ filter. The pellets from the centrifuged sonicates are resuspended in 30 ml of 5 mM NaCl, 25 mM Tris base, pH 7.0.

The 3 ml fractions of the filtrates are applied to Bio-Rad Econo-Pac 10DG columns that had been previously equilibrated with 10 ml of 5 mM NaCl, 25 mM Tris base, pH 7.0. The flow through collected during sample loading is discarded. The samples are fractionated with two subsequent additions of 4 ml each of the NaCl—Tris equilibration buffer. The first three fractions are saved for testing. The first fraction should contain all material above about 6,000 mol. wt. The subsequent fractions should contain material smaller than 6,000 mol. wt.

A sample of the sonicated filtrate and the resuspended pellet following sonication, are tested along with the three fractions from the 10DG column for activity on *P. xylostella* neonates in surface contamination assays. The filtered supernatant of the sonicate and the first column fraction from the 9369 sample is highly active on *P. xylostella*. The second and third fractions from the 9369 sample are not active. None of the samples from the DH5a with the Blue Script pasmid culture have activity. These results suggest that the insecticidal activity encoded on *X. nematophilus* clone pCIB9369 as well as the homologues from pCIB9381, pCIB9354, and pCIB9383-21 are larger than 6,000 molecular weight.

Example 9

Stability of the Insecticidal Activity

A 300 ml of Luria broth supplemented with 100 μg/ml ampicillin is inoculated with pCIB9369 and grown over night at 37° C. The samples are placed in sterile 15 ml screw cap tubes and stored at 22° C. and 4° C. One sample is centrifuged and the supernatant removed, freeze dried and stored at 22° C. These samples are stored in these conditions for 2 weeks and then bioassayed against Px. The freeze dried material is resuspended in the same volume as prior to freeze drying the sample. All samples are resuspended by vortexing. Another sample is treated at 100° C. for 5 minutes.

| Treatment | Result |
|---|---|
| 22° C. (2 weeks) | ++ |
| 4° C. (2 weeks) | ++ |
| Freeze Dried (2 weeks) | ++ |
| 100° C. for 5 minutes | na | na = not active.

Example 10

Heat Inactivation of the Insecticidal Activity

The heat stability of the toxin is determined. Overnight cultures of the *E. coli* strain pCIB9369 (*E. coli* host DH5a, carrying the 3.0 kb DNA of *Xenorhabdus nematophilus*) are grown in a 50:50 mixture of Luria broth and terrific broth. Cultures are grown at 37° C. in culture tubes on a tube roller. Samples of one ml each of the culture are placed in a 1.5 ml eppendorf tube and placed at 60° C., 80° C. The samples are removed after five minutes and allowed to cool to room temperature. This sample along with an untreated portion of the culture is assayed on *P. xylostella*. 50 μl of sample of sample is spread on diet, allowed to dry and neonate larvae *P. xylostella* applied to the surface. The assay is incubated for 5 days at room temperature.

The untreated sample and the sample treated at 60° C. cause 100% mortality. The sample treated at 80° C. and a diet alone control do not cause observable mortality.

Example 11

Protease Treatment of the Insecticidal Activity

*Xenorhabdus nematophilus* cosmid clone pCIB9369 and Stratagene's Blue Script vector in *E. coli* host DH5 are grown in media consisting of 50% Terrific broth and 50% Luria broth, supplemented with 50 μg/ml of ampicilin. Shake flask cultures (300 ml in 1000 ml baffled flasks) are grown at 250 RPM, overnight at 37° C. Cultures of each strain are centrifuged at 7,000 RPM in a Sorvall GS-3 rotor at 4° C. The pelleted cells are resuspended in 30 ml of 5 mM NaCl, 25 mM Tris base, pH 7.0. The concentrated cells are disrupted by sonication using a Branson Model 450 Sonicator for approximately eight 10 second cycles with cooling on ice between cycles. The sonicates are centrifuged in a Sorvall SS34 rotor at 6,000 RPM for 10 minutes at 4° C. The resultant supernatants are filtered through a 0.2 μ filter. One ml samples of the supernatants are adjusted to 5 mM Ca++ with the addition of $CaCl_2$. Protease K (Gibco BRL; Gaithersburg, Md.) is added to 500 μg/ml. Samples are incubated for 2 and 24 hr at 37° C. Control samples are prepared and incubated with added Ca++ but no protease.

The sonicate filtrate from pCIB9369 and the pCIB9369 samples incubated in the presence of 5 mM Ca++ produce 100% mortality on *Plutella xylostella* neonate larvae. The pCIB9369 samples incubated with protease K in addition to Ca++ show slightly less mortality, approximately 90% mortality on Plutella.

Example 12

Sequence Comparisons with the Protein Sequence of cry3A and the Protein Sequence of a Juvenile Hormone Esterase The nucleotide sequence of pCIB9369 (SEQ ID NO:1) reveals two open reading frames (ORFs) at nucleotides 569–976 and 1045–2334. ORF #1 has no homology to any sequences in Genbank after a search with the UWGCG Blast and Gap programs. A Gap analysis of the protein encoded by ORF #2 of pCIB9369 by the Blast program identifies some insignificant homology (21% identity) to *Bacillus thuringensis* cry3A protein. However, a Gap analysis of the protein encoded by ORF #2 of pCIB9369 (SEQ ID NO:3) by the Blast program does identify homology (30.6% AA identity and 44.1% AA similarity) to a juvenile hormone esterase-related protein (GenBank accession 2921553; Henikoff et al., *PNAS USA* 89: 10915–10919 (1992)).

The nucleotide sequences of pCIB9381, pCIB9354, and pCIB9383-21 also reveal two open reading frames in each of these clones. The nucleotide sequences of the two ORFs in each of pCIB9381 and pCIB9383-21 are all over 90% identical to those in pCIB9369. Hence, the ORF #2 proteins of pCIB9381 and pCIB9383-21 have essentially the same homology to the juvenile hormone esterase-related protein as does the ORF #2 protein of pCIB9369. The nucleotide sequence of ORF #1 of pCIB9354 is 77% identical to the nucleotide sequence of ORF #1 of pCIB9369, and the nucleotide sequence of ORF #2 of pCIB9354 is 79% identical to the nucleotide sequence of ORF #2 of pCIB9369. The ORF #2 protein of pCIB9354 also has homology to the juvenile hormone esterase-related protein (29.2% AA identity and 42.2% AA similarity).

Example 13

Sequence Comparison of pCIB9369 and Sequences from WO 98/08388

Twenty-two sequences of 60 nucleotides each (60-mers) are derived from the 38.2 kb DNA fragment whose nucleotide sequence is described in WO 98/08388 and are compared to the nucleotide sequence of pCIB9362–3, which comprises pCIB9369. The first 60-mer starts at base 1 in the 38.2 kb DNA fragment, while the other 60-mers are located at approximately 2 kb intervals on the DNA fragment. Their positions on the 38.2 kb DNA fragment are listed below:

1–60; 2,041–2,100; 4,021–4,080; 6,001–6,060; 8,041–8, 100; 10,021–10,080; 12,001–12,060; 14,041–14,100; 16,021–16,080; 18,001–18,060; 20,041–20,100; 22,021–22, 080; 24,001–24,060; 26,041–26,100; 28,021–28,080; 30,001–30,060; 32,041–32,100; 34,021–34,080; 36,001–36, 060; 38,041–38,100; 38,161–38,220.

The sequences are compared using UWGCG Gap program and each of the 22 60-mer sequences as well as their complementary sequences are tested. The results of these alignments indicate that the highest percentage of identity is 53%, which is not considered to be a significant homology in the art.

Example 14

Southern Blot Analysis using Probes Derived from WO 98/08388 Sequences

Pairs of oligonucleotides are designed to amplify DNA fragments of the 38.2 kb DNA fragment published in WO 98/08388. The oligonucleotides are ordered from Genosys Biotechnologies (The Woodlands, Tex.) and their positions in the 38.2 kb DNA fragment are indicated below. Also listed are their and the sizes of the amplified PCR fragments:
VK1046: positions 20–40
VK1047: positions 2,078–2,100
Size of the PCR fragment amplified using VK1046 and VK1047: 2,080 bp
VK1048: positions 11,221–11,241
VK1049: positions 13,360–13,380
Size of the PCR fragment amplified using VK1048 and VK1049: 2,120 bp
VK1050: positions 26,581–26,601
VK1051: positions 28,537–28,560
Size of the PCR fragment amplified using VK1050 and VK1051: 1,979 bp
VK1052: positions 18,901–18,921
VK1053: positions 20,321–20,340
Size of the PCR fragment amplified using VK1052 and VK1053: 1,439 bp
VK1054: positions 34,261–34,281
VK1055: positions 35,320–35,340 BP
Size of the PCR fragment amplified using VK1054 and VK1055: 1,079 bp The PCR reactions are completed using a Perkin-Elmer 9600 Thermo-Cycler with the following conditions: 94° C., 2 min.; then 30 cycles at 94° C., 30 sec; 54° C., 30 sec; 72° C., 4 min. The samples contain 800 ng of Xenorhabdus nematophilus DNA, 0.1–0.5 µM of each pair of oligonucleotides, 250 µM dNTP, 5U Taq Polymerase and 1×buffer (Perkin-Elmer) in a final volume of 100 µl. The completed reactions are precipitated in ethanol, resuspended in TE and loaded on a 1% SeaPlaque (FMC, Rockland, Me.) TBE gel. After electrophoresis, the fragments are cut out from the gel after ethidium bromide staining and visualization under UV light. The gel slices are melted at 65° C. and 10 µl aliquots are mixed with 10 µl distilled water, boiled for 5 min. and placed on ice. Then, 15 µl of Random Priming label buffer (GIBCO-BRL, Gaithersburg, Md.), 6µ dNTP mix (without dCTP), 80 µlCi α-dCT$^{32}$P and 1 µl Klenow are mixed. The labeling reaction is carried out during 60 min. at room temperature. The samples are cleaned up on Nick columns (Pharmacia Biotech) according to the supplier's recommendations. The probes are boiled for 5 min. and placed on ice.

A Southern blot is performed by digesting Xenorhabdus nematophilus total DNA, DNA derived from cosmids pCIB9362 and pCIB9363 (these cosmids overlap over 25 kb and both contain the DNA fragment of pCIB9369; pCIB9362 was used for subcloning), DNA derived from subclones pCIB9362-3 (9 kb SacII fragment) and pCIB9369 (2.96 kb ClaI fragment), digested with ClaI, SacII or HindIII. The digestion reactions are loaded on a 0.75% agarose TBE gel and run overnight. A picture is taken and the gel is treated as described by Bio-Rad for blotting to a Zeta-Probe hybridization membrane. After blotting, the membrane is baked at 80° C. for 30 min. The membrane is then placed in 7% SDS, 250 mM sodium phosphate, pH 7.2 and incubated at 67° C. for 30 min. Fresh solution is added and after equilibration to 67° C., the radioactive probes described above are added and allowed to hybridize overnight. The membrane is washed in 2×SSC, 0.5% SDS for 30 min. at 67° C. and then 0.5×SSC, 0.5% SDS for 30 min. at 67° C. The membrane is exposed on to a film for 1 hr and 3 hr. The film is developed and the results show that the PCR probes from the WO 98/08388 sequence do not hybridize to the DNA of the cosmids or the DNA of the subclones described in this invention. However, a strong hybridization signal is observed with X. nematophilus DNA.

These results corroborate the results of the sequence comparisons and show that clone pCIB9369 is different from the nucleotide sequence described in WO 98/08388.

B. Expression of the Nucleic Acid Sequences of the Invention in Heterologous Microbial Hosts Microorganisms which are suitable for the heterologous expression of the nucleotide sequences of the invention are all microorganisms which are capable of colonizing plants or the rhizosphere. As such they will be brought into contact with insect pests. These include gram-negative microorganisms such as Pseudomonas, Enterobacterand Serratia, the gram-positive microorganism Bacillus and the fungi Trichoderma, Gliocladium, and Saccharomyces cerevisiae. Particularly preferred heterologous hosts are Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum, Gliocladium virens, and Saccharomyces cerevisiae.

Example 19

Expression of the Nucleotide Sequences in E. coli and Other Gram-Negative Bacteria Many genes have been expressed in gram-negative bacteria in a heterologous manner. Expression vector pKK223-3

(Pharmacia catalogue #27-4935-01) allows expression in *E. coli*. This vector has a strong tac promoter (Brosius, J. et al., Proc. Natl. Acad. Sci. USA 81) regulated by the lac repressor and induced by IPTG. A number of other expression systems have been developed for use in *E. coli*. The thermoinducible expression vector $pP_L$ (Pharmacia #27-4946-01) uses a tightly regulated bacteriophage λ promoter which allows for high level expression of proteins. The lac promoter provides another means of expression but the promoter is not expressed at such high levels as the tac promoter. With the addition of broad host range replicons to some of these expression system vectors, expression of the nucleotide sequence in closely related gram negative-bacteria such as Pseudomonas, Enterobacter, Serratia and Erwinia is possible. For example, pLRKD211 (Kaiser & Kroos, Proc. Natl. Acad. Sci. USA 81: 5816–5820 (1984)) contains the broad host range replicon ori T which allows replication in many gram-negative bacteria.

In *E. coli*, induction by IPTG is required for expression of the tac (i.e. trp-lac) promoter. When this same promoter (e.g. on wide-host range plasmid pLRKD211) is introduced into Pseudomonas it is constitutively active without induction by IPTG. This trp-lac promoter can be placed in front of any gene or operon of interest for expression in Pseudomonas or any other closely related bacterium for the purposes of the constitutive expression of such a gene. Thus, a nucleotide sequence whose expression results in an insecticidal toxin can therefore be placed behind a strong constitutive promoter, transferred to a bacterium which has plant or rhizosphere colonizing properties turning this organism to an insecticidal agent. Other possible promoters can be used for the constitutive expression of the nucleotide sequence in gram-negative bacteria. These include, for example, the promoter from the Pseudomonas regulatory genes gafA and lemA (WO 94/01561) and the Pseudomonas savastanoi IAA operon promoter (Gaffney et al., *J. Bacteriol.* 172: 5593–5601 (1990).

Example 20

Expression of the Nucleotide Sequences in Gram-Positive Bacteria

Heterologous expression of the nucleotides sequence in gram-positive bacteria is another means of producing the insecticidal toxins. Expression systems for Bacillus and Streptomyces are the best characterized. The promoter for the erythromycin resistance gene (ermR) from *Streptococcus pneumoniae* has been shown to be active in gram-positive aerobes and anaerobes and also in *E. coli* (Trieu-Cuot et al., Nuci Acids Res 18: 3660 (1990)). A further antibiotic resistance promoter from the thiostreptone gene has been used in Streptomyces cloning vectors (Bibb, Mol Gen Genet 199: 26–36 (1985)). The shuttle vector pHT3101 is also appropriate for expression in Bacillus (Lereclus, FEMS Microbiol Lett 60: 211–218 (1989)). A significant advantage of this approach is that many gram-positive bacteria produce spores which can be used in formulations that produce insecticidal agents with a longer shelf life. Bacillus and Streptomyces species are aggressive colonizers of soils Example 21

Expression of the Nucleotide Sequences in Fungi

*Trichoderma harzianum* and *Gliocladium virens* have been shown to provide varying levels of biocontrol in the field (U.S. Pat. No. 5,165,928 and U.S. Pat. No. 4,996,157, both to Cornell Research Foundation). A nucleotide sequence whose expression results in an insecticidal toxin could be expressed in such a fungus. This could be accomplished by a number of ways which are well known in the art. One is protoplast-mediated transformation of the fungus by PEG or electroporation-mediated techniques. Alternatively, particle bombardment can be used to transform protoplasts or other fungal cells with the ability to develop into regenerated mature structures. The vector pAN7-1, originally developed for Aspergillus transformation and now used widely for fungal transformation (Curragh et al., *Mycol. Res.* 97(3): 313–317 (1992); Trooley et al., *Curr. Genet.* 21: 55–60 (1992); Punt et al., Gene 56: 117–124 (1987)) is engineered to contain the nucleotide sequence. This plasmid contains the *E. coil* the hygromycin B resistance gene flanked by the *Aspergillus nidulans* gpd promoter and the trpC terminator (Punt et al., Gene 56: 117–124 (1987)).

In a preferred embodiment, the nucleic acid sequences of the invention are expressed in the yeast *Saccharomyces cerevisiae*. For example, each of the two ORF's from pCIB9369, pCIB9381, pCIB9354, or pCIB9383 are cloned into individual vectors with the GAL1 inducible promoter and the CYC1 terminator. Each vector has ampicillin resistance and the 2 micron replicon. The vectors preferably differ in their yeast growth markers. The constructs are transformed into *S. cerevisiae* independently and together. The ORFs are expressed together and tested for protein expression and insecticidal activity.

C. Formulation of the Insecticidal Toxin

Insecticidal formulations are made using active ingredients which comprise either the isolated toxin or alternatively suspensions or concentrates of cells which produce it and which are described in the examples above. For example, *E. coli* cells expressing the insecticidal toxin may be used for the control of the insect pests. Formulations are made in liquid or solid form and are described below.

Example 18

Liquid Formulation of Insecticidal Compositions

In the following examples, percentages of composition are given by weight:

| 1. Emulsifiable concentrates: | a | b | c |
| --- | --- | --- | --- |
| Active ingredient | 20% | 40% | 50% |
| Calcium dodecylbenzenesulfonate | 5% | 8% | 6% |
| Castor oil polyethlene glycol ether (36 moles of ethylene oxide) | 5% | — | — |
| Tributylphenol polyethylene glyco ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160–190°) | — | — | 94% | — |

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgit | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 19

Solid Formulation of Insecticidal Compositions

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethyfene oxide) | 4% |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

D. Expression of the Nucleotide Sequences in Transgenic Plants

The nucleic acid sequences described in this application can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgtl1, λgtl0 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAll; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the nucleotide sequence of the invention confer insect resistance to the transgenic plants.

Example 22

Modification of Coding Sequences and Adjacent Sequences

The nucleotide sequences described in this application can be modified for expression in transgenic plant hosts. A host plant expressing the nucleotide sequences and which produces the insecticidal toxins in its cells has enhanced resistance to insect attack and is thus better equipped to withstand crop losses associated with such attack.

The transgenic expression in plants of genes derived from microbial sources may require the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (Science 261: 754–756 (1993)) have expressed the Pseudomonas nahG gene in transgenic plants under the control of the CaMV 35S promoter and the CaMV tml terminator successfully without modification of the coding sequence and with x bp of the Pseudomonas gene upstream of the ATG still attached, and y bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as Bacillus. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (NAR 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | | |
|---|---|---|---|---|---|---|---|---|---|---|
| | -10 | -9 | -8 | -7 | -6 | -5 | -4 | -3 | -2 | -1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

Example 23

Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and Arabidopsis—Norris et al., *Plant Mol. Biol.* 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The *Arabidopsis ubiquitin* promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRl site between the promoter and the terminator and has a pUC-type backbone. A derivative of pCGN1761 is constructed which has a modified polylinker which includes Notl and Xhol sites in addition to the existing EcoRl site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by Hindlll, Sphl, Sall, and Xbal sites 5' to the promoter and Xbal, BamHl and Bgll sites 3' to the terminator for transfer to transformation vectors such as those described below. Furthermore, the double 35S promoter fragment can be removed by 5' excision with Hindlll, Sphl, Sall, Xbal, or Pstl, and 3' excision with any of the polylinker restriction sites (EcoRl, Notl or Xhol for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the Actl promoter have been constructed specifically for use in monocotyledons (McElroy et al. Mol. Gen. Genet. 231: 150–160 (1991)). These incorporate the ActI-intron 1, Adhl 5' flanking sequence and Adhl-intron 1 (from the maize alcohol dehydrogenase gene) and sequence from the CaMV 35S promoter. Vectors showing highest expression were fusions of 35S and Actl intron or the Actl 5' flanking sequence and the Actl intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice Actl promoter with its first intron has also been found to direct high expression in cultured barley cells (Chibbar et al. Plant Cell Rep. 12: 506–509 (1993)).

d. Inducible Expression, the PR-1 Promoter

The double 35S promoter in pCGN1761ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., 1992). pCIB1004 is cleaved with Ncol and the resultant 3' overhang of the linearized fragment is rendered blunt by treatment with T4 DNA polymerase. The fragment is then cleaved with Hindlll and the resultant PR-1a promoter-containing fragment is gel purified and cloned into pCGN1761 ENX from which the double 35S promoter has been removed. This is done by cleavage with Xhol and blunting with T4 polymerase, followed by cleavage with Hindlll and isolation of the larger vector-terminator containing fragment into which the pCIB1004 promoter fragment is cloned. This generates a pCGN1761ENX derivative with the PR-1a promoter and the tml terminator and an intervening polylinker with unique EcoRl and Notl sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans*, the alcA gene encodes alcohol dehydrogenase 1, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6×GAL4/minimal promoter. Thus, tissue- or organ-specificity of the fusion protein is achieved leading to inducible tissue- or organ-specificity of the insecticidal toxin.

g. Root Specific Expression

Another pattern of gene expression is root expression. A suitable root promoter is described by de Framond (FEBS 290: 103–106 (1991)) and also in the published patent application EP 0 452 269, which is herein incorporated by reference. This promoter is transferred to a suitable vector such as pCGN1761 ENX for the insertion of a selected gene and subsequent transfer of the entire promoter-gene-terminator cassette to a transformation vector of interest.

h. Wound-Inducible Promoters

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wun1 gene. Xu et al. show that a wound-inducible promoter from the dicotyledon potato (pin2) is active in the monocotyledon rice. Further, Rohrmeier & Lehle describe the cloning of the maize Wip1 cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-preferred Expression

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-specific Expression

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-specific Expression

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15: 65–79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Example 24

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptil gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below, the construction of two typical vectors suitable for Agrobacterium transformation is described.

a. pCIB200 and pCIB2001

The binary vectors pcIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTIl (Messing & Vierra, Gene 19: 259–268 (1982): Bevan et al., Nature 304: 184–187 (1983): McBride et al., Plant Molecular Biology 14: 266–276 (1990)). Xhol linkers are ligated to the EcoRV fragment of PCIB7 which contains the left and right T-DNA borders, a plant selectable nos/nptll chimeric gene and the pUC polylinker (Rothstein et al., Gene 53: 153–161 (1987)), and the Xhol-digested digested fragment are cloned into SallI-digested pTJS75kan to create pCIB200 (see also EP 0 332 104, example 19). pCIB200 contains the following unique polylinker restriction sites: EcoRl, Sstl, Kpnl, Bglll, Xbal, and SalI. pCIB2001 is a derivative of pCIB200 created by the insertion into the polylinker of additional restriction sites. Unique restriction sites in the polylinker of pCIB2001 are EcoRl, Sstl, Kpnl, Bglll, Xbal, Sall, Mlul, Bcll, Avrll, Apal, Hpal, and Stul. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriTand OriVfunctions also from RK2. The pCIB2001 polylinker is suitable for the cloning of plant expression cassettes containing their own regulatory signals.

b. pCIB10 and Hygromycin Selection Derivatives thereof

The binary vector pCIB10 contains a gene encoding kanamycin resistance for selection in plants and T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites Sspl and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Center, Norwich and the a 400 bp SmaI fragment containing the bar gene from *Streptomyces viridochromogenes* is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites Sphl, Pstl, Hindlll, and BamHl. This vector is suitable for the cloning of plant expression cassettes containing their own regulatory signals.

b. pSOG19 and pSOG35 pSOG35 is a transformation vector that utilizes the *E. coli* gene dihydrofolate reductase (DFR) as a selectable marker conferring resistance to methotrexate. PCR is used to amplify the 35S promoter (−800 bp), intron 6 from the maize Adh1 gene (−550 bp) and 18 bp of the GUS untranslated leader sequence from pSOG10. A 250-bp fragment encoding the *E. coli* dihydrofolate reductase type II gene is also amplified by PCR and these two PCR fragments are assembled with a Sacl-Pstl fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have Hindulll, Sphl, Pstl and EcoRl sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Example 25

Transformation

Once a nucleic acid sequence of the invention has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterlum strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep Z: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using Agrobacterium has also been described. See, WO 94/00977 and U.S. Pat. No. 5,591,616, which are incorporated herein by reference.

3. Transformation of Plastids

Seeds of *Nicotiana tabacum* c.v. 'Xanthi nc' are germinated seven per plate in a 1" circular array on T agar medium and bombarded 12–14 days after sowing with 1 µm tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings are incubated on T medium for two days after which leaves are excised and placed abaxial side up in bright light (350–500 µmol photons/m$^2$/s) on plates of RMOP medium (Svab, Z., Haidukiewicz, P. and Maliga, P. (1990) *PNAS* 87, 8526–8530) containing 500 µg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloninq: A Laboratory Manual*, Cold Spring Harbor Laboratory, Cold Spring Harbor). BamHl/EcoRl-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHl/Hindlll DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

E. Breeding and Seed Production

Example 26

Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of *Plant Genetics and Breeding*, John Wiley & Sons, New York (1981); *Crop Breeding*, Wood D. R. (Ed.) American Society of Agronomy Madison, Wis. (1983); Mayo O., The Theory of Plant Bieeding, Second Edition, Clarendon Press, Oxford (1987); Singh, D. P., Breeding for Resistance to Diseases and Insect Pests, Springer-Verlag, New York (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pestidice treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

Example 27

Seed Production

In seed production, germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods, such as the methods exemplified above, which are characterized by the use of transgenic plants, transgenic plant material, or transgenic seed according to the present invention.

The seeds may be provided in a bag, container or vessel comprised of a suitable packaging material, the bag or container capable of being closed to contain seeds. The bag, container or vessel may be designed for either short term or long term storage, or both, of the seed. Examples of a suitable packaging material include paper, such as kraft paper, rigid or pliable plastic or other polymeric material, glass or metal. Desirably the bag, container, or vessel is comprised of a plurality of layers of packaging materials, of the same or differing type. In one embodiment the bag, container or vessel is provided so as to exclude or limit water and moisture from contacting the seed. In one example, the bag, container or vessel is sealed, for example heat sealed, to prevent water or moisture from entering. In another embodiment water absorbent materials are placed between or adjacent to packaging material layers. In yet another embodiment the bag, container or vessel, or packaging material of which it is comprised is treated to limit, suppress or prevent disease, contamination or other adverse affects of storage or transport of the seed. An example of such treatment is sterilization, for example by chemical means or by exposure to radiation. Comprised by the present invention is a commercial bag comprising seed of a transgenic plant comprising a gene of the present invention that is expressed in said transformed plant at higher levels than in a wild type plant, together with a suitable carrier, together with label instructions for the use thereof for conferring broad spectrum disease resistance to plants.

The above disclosed embodiments are illustrative. This disclosure of the invention will place one skilled in the art in possession of many variations of the invention. All such obvious and foreseeable variations are intended to be encompassed by the appended claims.

What is claimed is:

1. An isolated toxin that is active against insects, wherein said toxin comprises an amino acid sequence encoded by a nucleotide sequence that has a compliment that hybridizes to a nucleotide sequence selected from the group consisting of nucleotides 569–979 of SEQ ID NO: 1, nucleotides 1045–2334 of SEQ ID NO: 1, SEQ ID NO: 4, SEQ ID NO: 6, SEQ ID NO: 8, SEQ ID NO: 10, SEQ ID NO: 12, and SEQ ID NO: 14 in 7% sodium dodecyl sulfate (SDS), 0.5 M NaPO$_4$, 1 mM EDTA at 50° C. with washing in 0.1×SSC, 0.1% SDS at 65° C.

2. A toxin according to claim 1, wherein said toxin is active against *Plutelia xylostella*.

3. A toxin according to claim 1, wherein said toxin is produced by the *E. coli* strain designated as NRRL accession number B-21883.

4. A toxin according to claim 1, wherein said toxin comprises an amino acid sequence selected from the group consisting of: SEQ ID NOs:2, 3, 5, 7, 9, 11, 13, and 15.

5. A toxin according to claim 4, wherein said toxin comprises an amino acid sequence selected from the group consisting of: SEQ ID NOs:2, 5, 9, and 13.

6. A toxin according to claim 4, wherein said toxin comprises an amino acid sequence selected from the group consisting of: SEQ ID NOs:3, 7, 11, and 15.

7. A composition comprising an insecticidally effective amount of a toxin according to claim 1.

8. A method of controlling an insect comprising delivering to the insect an effective amount of a toxin according to claim 1.

9. The method of claim 8, wherein the insect is *Plutella xylostella*.

10. The method of claim 9, wherein the toxin is delivered to the insect orally.

11. A toxin according to claim 1, wherein said nucleotide sequence has a compliment that hybridizes to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14 in 7% sodium dodecyl sulfate (SDS), 0.5 M NaPO$_4$, 1 mM EDTA at 50° C. with washing in 0.1×SSC, 0.1% SDS at 65° C.

12. A toxin according to claim 1, wherein said nucleotide sequence has a compliment that hybridizes to nucleotides 569–979 of SEQ ID NO:1, SEQ ID NO:4, SEQ ID NO:8, or SEQ ID NO:12 in 7% sodium dodecyl sulfate (SDS), 0.5 M NaPO$_4$, 1 mM EDTA at 50° C. with washing in 0.1×SSC, 0.1% SDS at 65° C.

13. A toxin according to claim 1, wherein said nucleotide sequence has a compliment that hybridizes to nucleotides 1045–2334 of SEQ ID NO:1, SEQ ID NO:6, SEQ ID NO:10, or SEQ ID NO:14 in 7% sodium dodecyl sulfate (SDS), 0.5 M NaPO$_4$, 1 mM EDTA at 50° C. with washing in 0.1×SSC, 0.1% SDS at 65° C.

* * * * *

UNITED STATES PATENT AND TRADEMARK OFFICE
CERTIFICATE OF CORRECTION

PATENT NO. : 6,277,823 B1
APPLICATION NO. : 09/668648
DATED : August 21, 2001
INVENTOR(S) : Kramer et al.

It is certified that error appears in the above-identified patent and that said Letters Patent is hereby corrected as shown below:

COL. 45. LN 58, To COL. 76, LN 67
Please include the following sequence listing into the patent, see attached pages 1-18.

Signed and Sealed this

Eighth Day of August, 2006

JON W. DUDAS
*Director of the United States Patent and Trademark Office*

SEQUENCE LISTING

<110> Kramer, Vance
      Morgan, Michael
      Anderson, Arne

<120> NOVEL INSECTICIDAL TOXINS
      AND NUCLEIC ACID SEQUENCES CODING THEREFOR

<130> PB/5-30472A/USN

<140>
<141>

<160> 15

<170> PatentIn Ver. 2.0

<210> 1
<211> 2978
<212> DNA
<213> Xenorhabdus nematophilus

<220>
<221> CDS
<222> (569)..(976)
<223> orf1

<220>
<221> CDS
<222> (1045)..(2331)
<223> JHE-like orf2

<220>
<223> pCIB9369

<400> 1
```
atcgatgtga cggcagagta tttttattcc tgtaaactga cgacaatgca tttctaagat  60
atcaatataa taatgataaa tttattgatc atatatctgt tatattttga ttgaaaatta 120
ttgaatatac ctcttgtact aaattcatta cattttttt actttaaaca acattaaatt 180
cacacataat acagcttaaa tataacatgt gatatatatt atgattataa aaaacattaa 240
aataaataat acgccacata tattaacaat atctaattac tgatgatact attttctgag 300
tatatataaa tcttaaagaa aataattatt ttttatattt cacatcaatt taaaatctgc 360
ttagaatgcc ccccggcatc acaagaaaac aaaatcattc aagtaataca atagagttaa 420
atttaaaaat aacatgtata acaaaataca tagacaatta tacatgtaaa tgacagacaa 480
ctgacaaaac atagcaaaaa aacgccttaa atattaaggt atcaaaacaa tatatcagac 540
tatcttaaat ctaataggag aatccctc atg att aca ata cat atc agt ggt    592
                                Met Ile Thr Ile His Ile Ser Gly
                                 1               5 ggt agt gta aca att aat aac aat ata gta aca gaa act gat gtc caa    640
Gly Ser Val Thr Ile Asn Asn Asn Ile Val Thr Glu Thr Asp Val Gln
     10              15                  20 aat aca ccc gct tca gcg cct tta tca att act aat ttt agg gat atg    688
Asn Thr Pro Ala Ser Ala Pro Leu Ser Ile Thr Asn Phe Arg Asp Met
 25              30                  35                  40
```

```
aca ata gaa cct cat tca tct gtt gag gcg ata aga acc gat aca ccg    736
Thr Ile Glu Pro His Ser Ser Val Glu Ala Ile Arg Thr Asp Thr Pro
                 45                  50                  55 att att cct gaa tca cga cca aat tac tat gtt gct aat tct ggc ccg    784
Ile Ile Pro Glu Ser Arg Pro Asn Tyr Tyr Val Ala Asn Ser Gly Pro
                 60                  65                  70 gcc tca tca gtc aga gct gtt ttc tat tgg tcc cac tct ttt aca tca    832
Ala Ser Ser Val Arg Ala Val Phe Tyr Trp Ser His Ser Phe Thr Ser
                 75                  80                  85 gaa tgg ttt gaa tct tcc tct att att gta aaa gca ggc gaa gac gga    880
Glu Trp Phe Glu Ser Ser Ser Ile Ile Val Lys Ala Gly Glu Asp Gly
         90                  95                 100 gtc tta cat tca ccg ggt aat tct tta tat tac agc aag gtt gta att    928
Val Leu His Ser Pro Gly Asn Ser Leu Tyr Tyr Ser Lys Val Val Ile
105                 110                 115                 120 tat aac gat aca gac aaa cgt gct ttt gtt acc ggc tac aat cta taa    976
Tyr Asn Asp Thr Asp Lys Arg Ala Phe Val Thr Gly Tyr Asn Leu
                125                 130                 135 taacgcagaa atacaatcca tatttccaat gaatttcaaa taacatcctt aaggcaagaa 1036 acaaaatc atg aat aat gaa ccg atg aat act aat gaa tca caa gct tca  1086
         Met Asn Asn Glu Pro Met Asn Thr Asn Glu Ser Gln Ala Ser
                         140                 145                 150 gag ata gta ccc tca atg aat gaa tct ata tta gca gca cct tat tca   1134
Glu Ile Val Pro Ser Met Asn Glu Ser Ile Leu Ala Ala Pro Tyr Ser
                 155                 160                 165 att tct aca cct aat tat gaa tgg gat atg tca tca ata ata aaa gat   1182
Ile Ser Thr Pro Asn Tyr Glu Trp Asp Met Ser Ser Ile Ile Lys Asp
                 170                 175                 180 gct att att ggt ggt ata ggc ttt att cct ggt ccg ggc tca gca ata   1230
Ala Ile Ile Gly Gly Ile Gly Phe Ile Pro Gly Pro Gly Ser Ala Ile
                 185                 190                 195 tca ttt ttg tta ggg tta ttt tgg cca caa caa acc gac aat act tgg   1278
Ser Phe Leu Leu Gly Leu Phe Trp Pro Gln Gln Thr Asp Asn Thr Trp
         200                 205                 210 gag caa att ctc caa aaa gta gaa caa atg atc gag caa gcc aat ctc   1326
Glu Gln Ile Leu Gln Lys Val Glu Gln Met Ile Glu Gln Ala Asn Leu
215                 220                 225                 230 aaa act att caa gga ata ttg aac ggc gat ata caa gaa att aaa ggc   1374
Lys Thr Ile Gln Gly Ile Leu Asn Gly Asp Ile Gln Glu Ile Lys Gly
                 235                 240                 245 aaa atg gaa cat gtg caa ttc atg cta gaa tcc tca cct ggc act caa   1422
Lys Met Glu His Val Gln Phe Met Leu Glu Ser Ser Pro Gly Thr Gln
                 250                 255                 260 gaa agc cat gac gca tac atg ttt ctg gcg aga tat ctg gtc agt ata   1470
Glu Ser His Asp Ala Tyr Met Phe Leu Ala Arg Tyr Leu Val Ser Ile
                 265                 270                 275 gac gaa aaa ttc aag tct ttt gat aac aaa aca aat tat caa att ctt   1518
Asp Glu Lys Phe Lys Ser Phe Asp Asn Lys Thr Asn Tyr Gln Ile Leu
         280                 285                 290
```

```
ccc atg tat acc aat acg att atg tta caa gcc cct tat tgg aaa atg    1566
Pro Met Tyr Thr Asn Thr Ile Met Leu Gln Ala Pro Tyr Trp Lys Met
295                 300                 305                 310 ggt ata gag aga aaa gat gag atc aaa cta aca gat ata gaa gtt aat    1614
Gly Ile Glu Arg Lys Asp Glu Ile Lys Leu Thr Asp Ile Glu Val Asn
            315                 320                 325 gaa tta aaa gag ctg ata gga aaa tta tct acc agc gcc gat aaa tat    1662
Glu Leu Lys Glu Leu Ile Gly Lys Leu Ser Thr Ser Ala Asp Lys Tyr
                330                 335                 340 att cat gat gtc tat act cgt gaa tat gat aat gcg atg aac act tca    1710
Ile His Asp Val Tyr Thr Arg Glu Tyr Asp Asn Ala Met Asn Thr Ser
            345                 350                 355 aca gca gca aat atc acc aat aat tta tta tct gta aga ggc tat tgt    1758
Thr Ala Ala Asn Ile Thr Asn Asn Leu Leu Ser Val Arg Gly Tyr Cys
        360                 365                 370 tta tta cat ggt tta gaa tgt ctc gaa gtc att aac cat ata caa aat    1806
Leu Leu His Gly Leu Glu Cys Leu Glu Val Ile Asn His Ile Gln Asn
375                 380                 385                 390 aat agc ctt gag caa agt ttt tat cct aaa act atc agc tac tcc acc    1854
Asn Ser Leu Glu Gln Ser Phe Tyr Pro Lys Thr Ile Ser Tyr Ser Thr
            395                 400                 405 gta ttc gat cgc cag aca aat aaa aca agg gtt caa gcc ctg aca gaa    1902
Val Phe Asp Arg Gln Thr Asn Lys Thr Arg Val Gln Ala Leu Thr Glu
                410                 415                 420 gac gat caa atg caa gag cca ttc aag cct gct tta att aat ggg aag    1950
Asp Asp Gln Met Gln Glu Pro Phe Lys Pro Ala Leu Ile Asn Gly Lys
            425                 430                 435 tac aac aaa ata aaa tca ttg att ggg tat gta caa aga atc gga aac    1998
Tyr Asn Lys Ile Lys Ser Leu Ile Gly Tyr Val Gln Arg Ile Gly Asn
        440                 445                 450 gca ccc aga gtt gga ggc att aaa gtc aca ttt gca aac gat gca tct    2046
Ala Pro Arg Val Gly Gly Ile Lys Val Thr Phe Ala Asn Asp Ala Ser
455                 460                 465                 470 tat acc ctc ggt aca gta act tca gaa gta aac tca att gaa ctg aat    2094
Tyr Thr Leu Gly Thr Val Thr Ser Glu Val Asn Ser Ile Glu Leu Asn
            475                 480                 485 gac agc gtt ata acc agc ctg gaa gta tgg gga aat ggc gct att gat    2142
Asp Ser Val Ile Thr Ser Leu Glu Val Trp Gly Asn Gly Ala Ile Asp
                490                 495                 500 gag gca ttc ttt aca tta agt gac gga cgt caa ttt agg ctt ggc caa    2190
Glu Ala Phe Phe Thr Leu Ser Asp Gly Arg Gln Phe Arg Leu Gly Gln
            505                 510                 515 cgc tat gcc agt aac tat aga aaa tat gct gtc gat aac cac tat att    2238
Arg Tyr Ala Ser Asn Tyr Arg Lys Tyr Ala Val Asp Asn His Tyr Ile
        520                 525                 530 tca gga ttg tac tta gcc agt gat gaa cct tca ttg gca ggt caa gca    2286
Ser Gly Leu Tyr Leu Ala Ser Asp Glu Pro Ser Leu Ala Gly Gln Ala
535                 540                 545                 550 gca ggc att gca gtt tca tac cat atg ata gct gat aaa aaa tca         2331
```

```
Ala Gly Ile Ala Val Ser Tyr His Met Ile Ala Asp Lys Lys Ser
                555                 560                 565 tagtattaac aggcttctga tttcagacta agcaagtaag cggatcttca gagtcatata 2391 gcatgctata tgactgaaga gttatccgct cctcactttt aactaaactc attacatcct 2451 ccactaattt attcagcgat aaaaaacaca caatgaaaac caaacatttg tttgttattt 2511 tcataaaaaa tgcaactctt tgtttaataa aaatttatcg cagtataaaa tattgccagt 2571 tttatagact atattatatt ctcactttat ctatattttt agtttaaaat tcaagactaa 2631 aatcacactt ttatgcaaaa tgttcacttt ataaactta cgatcgtact ctcataatta 2691 gaatcaaata tcaaaataat ctttactgtt tatcagacat gcaatacaac attaatacaa 2751 aaaatagcta aggacatgat atgttgaaaa gggaaaatca gatattgcaa ctactgaagg 2811 gcgatccttt catgcagcag caagaaatcg ctgatatcct tggaattagc cgctcgtgtg 2871 ttgcaggaca tattatgaac taagcaaaa aaggatatat taaaggcaaa gggtatatct 2931 tatctaatga tgtttatact gttacaattg gtgctgccaa tatcgat             2978
```

<210> 2
<211> 135
<212> PRT
<213> Xenorhabdus nematophilus

<400> 2
```
Met Ile Thr Ile His Ile Ser Gly Gly Ser Val Thr Ile Asn Asn Asn
  1               5                  10                  15

Ile Val Thr Glu Thr Asp Val Gln Asn Thr Pro Ala Ser Ala Pro Leu
             20                  25                  30

Ser Ile Thr Asn Phe Arg Asp Met Thr Ile Glu Pro His Ser Ser Val
         35                  40                  45

Glu Ala Ile Arg Thr Asp Thr Pro Ile Ile Pro Glu Ser Arg Pro Asn
     50                  55                  60

Tyr Tyr Val Ala Asn Ser Gly Pro Ala Ser Val Arg Ala Val Phe
 65                  70                  75                  80

Tyr Trp Ser His Ser Phe Thr Ser Glu Trp Phe Glu Ser Ser Ile
             85                  90                  95

Ile Val Lys Ala Gly Glu Asp Gly Val Leu His Ser Pro Gly Asn Ser
             100                 105                 110

Leu Tyr Tyr Ser Lys Val Val Ile Tyr Asn Asp Thr Asp Lys Arg Ala
         115                 120                 125

Phe Val Thr Gly Tyr Asn Leu
     130                 135
```

<210> 3
<211> 429
<212> PRT
<213> Xenorhabdus nematophilus

<400> 3

```
Met Asn Asn Glu Pro Met Asn Thr Asn Glu Ser Gln Ala Ser Glu Ile
 1               5                   10                  15
Val Pro Ser Met Asn Glu Ser Ile Leu Ala Ala Pro Tyr Ser Ile Ser
            20                  25                  30
Thr Pro Asn Tyr Glu Trp Asp Met Ser Ser Ile Ile Lys Asp Ala Ile
            35                  40                  45
Ile Gly Gly Ile Gly Phe Ile Pro Gly Pro Gly Ser Ala Ile Ser Phe
    50                  55                  60
Leu Leu Gly Leu Phe Trp Pro Gln Gln Thr Asp Asn Thr Trp Glu Gln
 65                  70                  75                  80
Ile Leu Gln Lys Val Glu Gln Met Ile Glu Gln Ala Asn Leu Lys Thr
                85                  90                  95
Ile Gln Gly Ile Leu Asn Gly Asp Ile Gln Glu Ile Lys Gly Lys Met
            100                 105                 110
Glu His Val Gln Phe Met Leu Glu Ser Ser Pro Gly Thr Gln Glu Ser
            115                 120                 125
His Asp Ala Tyr Met Phe Leu Ala Arg Tyr Leu Val Ser Ile Asp Glu
            130                 135                 140
Lys Phe Lys Ser Phe Asp Asn Lys Thr Asn Tyr Gln Ile Leu Pro Met
145             150                 155                 160
Tyr Thr Asn Thr Ile Met Leu Gln Ala Pro Tyr Trp Lys Met Gly Ile
                165                 170                 175
Glu Arg Lys Asp Glu Ile Lys Leu Thr Asp Ile Glu Val Asn Glu Leu
            180                 185                 190
Lys Glu Leu Ile Gly Lys Leu Ser Thr Ser Ala Asp Lys Tyr Ile His
            195                 200                 205
Asp Val Tyr Thr Arg Glu Tyr Asp Asn Ala Met Asn Thr Ser Thr Ala
    210                 215                 220
Ala Asn Ile Thr Asn Asn Leu Leu Ser Val Arg Gly Tyr Cys Leu Leu
225                 230                 235                 240
His Gly Leu Glu Cys Leu Glu Val Ile Asn His Ile Gln Asn Asn Ser
                245                 250                 255
Leu Glu Gln Ser Phe Tyr Pro Lys Thr Ile Ser Tyr Ser Thr Val Phe
            260                 265                 270
Asp Arg Gln Thr Asn Lys Thr Arg Val Gln Ala Leu Thr Glu Asp Asp
            275                 280                 285
Gln Met Gln Glu Pro Phe Lys Pro Ala Leu Ile Asn Gly Lys Tyr Asn
    290                 295                 300
Lys Ile Lys Ser Leu Ile Gly Tyr Val Gln Arg Ile Gly Asn Ala Pro
305                 310                 315                 320
Arg Val Gly Gly Ile Lys Val Thr Phe Ala Asn Asp Ala Ser Tyr Thr
            325                 330                 335
Leu Gly Thr Val Thr Ser Glu Val Asn Ser Ile Glu Leu Asn Asp Ser
            340                 345                 350
```

```
Val Ile Thr Ser Leu Glu Val Trp Gly Asn Gly Ala Ile Asp Glu Ala
        355                 360                 365

Phe Phe Thr Leu Ser Asp Gly Arg Gln Phe Arg Leu Gly Gln Arg Tyr
    370                 375                 380

Ala Ser Asn Tyr Arg Lys Tyr Ala Val Asp Asn His Tyr Ile Ser Gly
385                 390                 395                 400

Leu Tyr Leu Ala Ser Asp Glu Pro Ser Leu Ala Gly Gln Ala Ala Gly
                405                 410                 415

Ile Ala Val Ser Tyr His Met Ile Ala Asp Lys Lys Ser
                420                 425
```

<210> 4
<211> 408
<212> DNA
<213> Xenorhabdus nematophilus

<220>
<221> CDS
<222> (1)..(405)
<223> orf1 of pCIB9381

<400> 4
```
atg att aca atc aat atc act ggt gat aat gta aga gtt aat aac aat    48
Met Ile Thr Ile Asn Ile Thr Gly Asp Asn Val Arg Val Asn Asn Asn
  1               5                  10                  15 ata gca aca gaa acc gac ctc caa aat aca cct gct tca gca ccc tta    96
Ile Ala Thr Glu Thr Asp Leu Gln Asn Thr Pro Ala Ser Ala Pro Leu
                 20                  25                  30 tca att att aat ttt agg gat atg aca ata gaa cct cat tca tct gtt   144
Ser Ile Ile Asn Phe Arg Asp Met Thr Ile Glu Pro His Ser Ser Val
             35                  40                  45 gag gcg ata aga acc gat aca ccg att att cct gaa tca cga cca aat   192
Glu Ala Ile Arg Thr Asp Thr Pro Ile Ile Pro Glu Ser Arg Pro Asn
         50                  55                  60 tac tat gtt gct aat tct ggc ccg gcc tca tca gtc aga gct gtt ttc   240
Tyr Tyr Val Ala Asn Ser Gly Pro Ala Ser Ser Val Arg Ala Val Phe
 65                  70                  75                  80 tat tgg tcc cac tct ttt aca tca gaa tgg ttt gaa tct tcc tct att   288
Tyr Trp Ser His Ser Phe Thr Ser Glu Trp Phe Glu Ser Ser Ser Ile
                     85                  90                  95 att gta aaa gca ggc gaa gac gga gtc tta cat tca ccg ggt aat tct   336
Ile Val Lys Ala Gly Glu Asp Gly Val Leu His Ser Pro Gly Asn Ser
                100                 105                 110 tta tat tac agc aag gtt gta att tat aac gat aca gac aaa cgt gct   384
Leu Tyr Tyr Ser Lys Val Val Ile Tyr Asn Asp Thr Asp Lys Arg Ala
            115                 120                 125 ttt gtt acc ggc tac aat cta taa                                    408
Phe Val Thr Gly Tyr Asn Leu
            130             135
```

<210> 5
<211> 135

<212> PRT
<213> Xenorhabdus nematophilus

<400> 5
Met Ile Thr Ile Asn Ile Thr Gly Asp Asn Val Arg Val Asn Asn Asn
 1               5                  10                  15

Ile Ala Thr Glu Thr Asp Leu Gln Asn Thr Pro Ala Ser Ala Pro Leu
            20                  25                  30

Ser Ile Ile Asn Phe Arg Asp Met Thr Ile Glu Pro His Ser Ser Val
             35                  40                  45

Glu Ala Ile Arg Thr Asp Thr Pro Ile Ile Pro Glu Ser Arg Pro Asn
         50                  55                  60

Tyr Tyr Val Ala Asn Ser Gly Pro Ala Ser Ser Val Arg Ala Val Phe
 65                  70                  75                  80

Tyr Trp Ser His Ser Phe Thr Ser Glu Trp Phe Glu Ser Ser Ser Ile
             85                  90                  95

Ile Val Lys Ala Gly Glu Asp Gly Val Leu His Ser Pro Gly Asn Ser
             100                 105                 110

Leu Tyr Tyr Ser Lys Val Val Ile Tyr Asn Asp Thr Asp Lys Arg Ala
            115                 120                 125

Phe Val Thr Gly Tyr Asn Leu
        130                 135

<210> 6
<211> 1290
<212> DNA
<213> Xenorhabdus nematophilus

<220>
<221> CDS
<222> (1)..(1287)
<223> JHE-like orf2 of pCIB9381

<400> 6
```
atg aat aat gaa ccg atg aat act aat gaa tca caa gtt tca gag ata    48
Met Asn Asn Glu Pro Met Asn Thr Asn Glu Ser Gln Val Ser Glu Ile
 1               5                  10                  15 gta ccc tca atg aat gaa tct ata tta gca gca cct tat tca att tct    96
Val Pro Ser Met Asn Glu Ser Ile Leu Ala Ala Pro Tyr Ser Ile Ser
             20                  25                  30 aca cct aat tat gaa tgg gat atg tca tca ata ata aaa gat gcc att   144
Thr Pro Asn Tyr Glu Trp Asp Met Ser Ser Ile Ile Lys Asp Ala Ile
         35                  40                  45 att ggt ggt ata ggc ttt att cct ggt ccg ggc tca gca ata tca ttt   192
Ile Gly Gly Ile Gly Phe Ile Pro Gly Pro Gly Ser Ala Ile Ser Phe
     50                  55                  60 ttg tta ggg tta ttt tgg cca caa caa acc gac aat act tgg gag caa   240
Leu Leu Gly Leu Phe Trp Pro Gln Gln Thr Asp Asn Thr Trp Glu Gln
 65                  70                  75                  80 att ctc caa aaa gta gaa caa atg atc gag caa gcc aat ctc aaa act   288
Ile Leu Gln Lys Val Glu Gln Met Ile Glu Gln Ala Asn Leu Lys Thr
             85                  90                  95
```

| | |
|---|---|
| att caa gga ata ttg aac ggc gat ata caa gaa att aaa ggc aaa atg<br>Ile Gln Gly Ile Leu Asn Gly Asp Ile Gln Glu Ile Lys Gly Lys Met<br>100 105 110 | 336 |
| gaa cat gtg caa ttc atg cta gaa tcc tca cct ggc act caa gaa agc<br>Glu His Val Gln Phe Met Leu Glu Ser Ser Pro Gly Thr Gln Glu Ser<br>115 120 125 | 384 |
| cat gac gca tac atg ttt ctg gcg aga tat ctg gtc agt ata gac gaa<br>His Asp Ala Tyr Met Phe Leu Ala Arg Tyr Leu Val Ser Ile Asp Glu<br>130 135 140 | 432 |
| aaa ttc aag tct ttt gat aac aaa aca aat tat caa att ctt ccc atg<br>Lys Phe Lys Ser Phe Asp Asn Lys Thr Asn Tyr Gln Ile Leu Pro Met<br>145 150 155 160 | 480 |
| tat acc aat acg att atg tta caa gcc cct tat tgg aaa atg ggt ata<br>Tyr Thr Asn Thr Ile Met Leu Gln Ala Pro Tyr Trp Lys Met Gly Ile<br>165 170 175 | 528 |
| gag aga aaa gat gag ata aaa cta aca gat ata gaa gtt aat gaa tta<br>Glu Arg Lys Asp Glu Ile Lys Leu Thr Asp Ile Glu Val Asn Glu Leu<br>180 185 190 | 576 |
| aaa gag ctg ata gga aaa tta tct acc agc gcc gat aaa tat att cat<br>Lys Glu Leu Ile Gly Lys Leu Ser Thr Ser Ala Asp Lys Tyr Ile His<br>195 200 205 | 624 |
| gat gtc tat act cgt gaa tat gat aat gcg atg aac act tca aca gca<br>Asp Val Tyr Thr Arg Glu Tyr Asp Asn Ala Met Asn Thr Ser Thr Ala<br>210 215 220 | 672 |
| gca aat atc acc aat aat tta tta tct gta aga ggc tat tgt tta tta<br>Ala Asn Ile Thr Asn Asn Leu Leu Ser Val Arg Gly Tyr Cys Leu Leu<br>225 230 235 240 | 720 |
| cat ggt tta gaa tgt ctc gaa gtc att aac cat ata caa aat aat agc<br>His Gly Leu Glu Cys Leu Glu Val Ile Asn His Ile Gln Asn Asn Ser<br>245 250 255 | 768 |
| ctt gag caa agt ttt tat cct aaa act atc agc tac tcc acc gta ttc<br>Leu Glu Gln Ser Phe Tyr Pro Lys Thr Ile Ser Tyr Ser Thr Val Phe<br>260 265 270 | 816 |
| gat cgc cag aca aat aaa aca agg gtt caa gcc ctg aca gaa gac gat<br>Asp Arg Gln Thr Asn Lys Thr Arg Val Gln Ala Leu Thr Glu Asp Asp<br>275 280 285 | 864 |
| caa atg caa gag cca ttc aag cct gct tta att aat ggg aag tac aac<br>Gln Met Gln Glu Pro Phe Lys Pro Ala Leu Ile Asn Gly Lys Tyr Asn<br>290 295 300 | 912 |
| aaa ata aaa tca ttg att ggg tat gta caa aga atc gga aac gca ccc<br>Lys Ile Lys Ser Leu Ile Gly Tyr Val Gln Arg Ile Gly Asn Ala Pro<br>305 310 315 320 | 960 |
| aga gtt gga ggc att aaa gtc aca ttt gca aac gat gca tct tat acc<br>Arg Val Gly Gly Ile Lys Val Thr Phe Ala Asn Asp Ala Ser Tyr Thr<br>325 330 335 | 1008 |
| ctc ggt aca gta act tca gaa gta aac tca att gaa ctg aat gac agc<br>Leu Gly Thr Val Thr Ser Glu Val Asn Ser Ile Glu Leu Asn Asp Ser<br>340 345 350 | 1056 |
| gtt ata acc agc ctg gaa gta tgg gga aat ggc gct gtt gat gag gca | 1104 |

```
Val Ile Thr Ser Leu Glu Val Trp Gly Asn Gly Ala Val Asp Glu Ala
        355                 360                 365
ttc ttt aca tta agt gac gga cgt caa ttt agg ctt ggc caa cgc tat    1152
Phe Phe Thr Leu Ser Asp Gly Arg Gln Phe Arg Leu Gly Gln Arg Tyr
    370                 375                 380
gcc agt aac tat aga aaa tat gct gtc gat aac cac tat att tca gga    1200
Ala Ser Asn Tyr Arg Lys Tyr Ala Val Asp Asn His Tyr Ile Ser Gly
385                 390                 395                 400
ttg tac tta gcc agt gat gaa cct tca ttg gca ggt caa gca gca ggc    1248
Leu Tyr Leu Ala Ser Asp Glu Pro Ser Leu Ala Gly Gln Ala Ala Gly
                405                 410                 415
att gca gtt tca tac cat atg ata gct gat aaa aaa tca tag            1290
Ile Ala Val Ser Tyr His Met Ile Ala Asp Lys Lys Ser
                420                 425
```

<210> 7
<211> 429
<212> PRT
<213> Xenorhabdus nematophilus

<400> 7
```
Met Asn Asn Glu Pro Met Asn Thr Asn Glu Ser Gln Val Ser Glu Ile
 1                   5                  10                  15

Val Pro Ser Met Asn Glu Ser Ile Leu Ala Ala Pro Tyr Ser Ile Ser
                20                  25                  30

Thr Pro Asn Tyr Glu Trp Asp Met Ser Ser Ile Ile Lys Asp Ala Ile
            35                  40                  45

Ile Gly Gly Ile Gly Phe Ile Pro Gly Pro Gly Ser Ala Ile Ser Phe
        50                  55                  60

Leu Leu Gly Leu Phe Trp Pro Gln Gln Thr Asp Asn Thr Trp Glu Gln
 65                 70                  75                  80

Ile Leu Gln Lys Val Glu Gln Met Ile Glu Gln Ala Asn Leu Lys Thr
                85                  90                  95

Ile Gln Gly Ile Leu Asn Gly Asp Ile Gln Glu Ile Lys Gly Lys Met
            100                 105                 110

Glu His Val Gln Phe Met Leu Glu Ser Ser Pro Gly Thr Gln Glu Ser
        115                 120                 125

His Asp Ala Tyr Met Phe Leu Ala Arg Tyr Leu Val Ser Ile Asp Glu
    130                 135                 140

Lys Phe Lys Ser Phe Asp Asn Lys Thr Asn Tyr Gln Ile Leu Pro Met
145                 150                 155                 160

Tyr Thr Asn Thr Ile Met Leu Gln Ala Pro Tyr Trp Lys Met Gly Ile
                165                 170                 175

Glu Arg Lys Asp Glu Ile Lys Leu Thr Asp Ile Glu Val Asn Glu Leu
            180                 185                 190

Lys Glu Leu Ile Gly Lys Leu Ser Thr Ser Ala Asp Lys Tyr Ile His
        195                 200                 205

Asp Val Tyr Thr Arg Glu Tyr Asp Asn Ala Met Asn Thr Ser Thr Ala
```

```
                210                     215                     220
Ala Asn Ile Thr Asn Asn Leu Leu Ser Val Arg Gly Tyr Cys Leu Leu
225                 230                 235                 240

His Gly Leu Glu Cys Leu Glu Val Ile Asn His Ile Gln Asn Asn Ser
                245                 250                 255

Leu Glu Gln Ser Phe Tyr Pro Lys Thr Ile Ser Tyr Ser Thr Val Phe
                260                 265                 270

Asp Arg Gln Thr Asn Lys Thr Arg Val Gln Ala Leu Thr Glu Asp Asp
                275                 280                 285

Gln Met Gln Glu Pro Phe Lys Pro Ala Leu Ile Asn Gly Lys Tyr Asn
    290                 295                 300

Lys Ile Lys Ser Leu Ile Gly Tyr Val Gln Arg Ile Gly Asn Ala Pro
305                 310                 315                 320

Arg Val Gly Gly Ile Lys Val Thr Phe Ala Asn Asp Ala Ser Tyr Thr
                325                 330                 335

Leu Gly Thr Val Thr Ser Glu Val Asn Ser Ile Glu Leu Asn Asp Ser
                340                 345                 350

Val Ile Thr Ser Leu Glu Val Trp Gly Asn Gly Ala Val Asp Glu Ala
                355                 360                 365

Phe Phe Thr Leu Ser Asp Gly Arg Gln Phe Arg Leu Gly Gln Arg Tyr
    370                 375                 380

Ala Ser Asn Tyr Arg Lys Tyr Ala Val Asp Asn His Tyr Ile Ser Gly
385                 390                 395                 400

Leu Tyr Leu Ala Ser Asp Glu Pro Ser Leu Ala Gly Gln Ala Ala Gly
                405                 410                 415

Ile Ala Val Ser Tyr His Met Ile Ala Asp Lys Lys Ser
                420                 425
```

<210> 8
<211> 408
<212> DNA
<213> Xenorhabdus poinarii

<220>
<221> CDS
<222> (1)..(405)
<223> orf1 of pCIB9354

```
<400> 8
atg atc aca atc aat atc agt ggt ggt aat gta aca att aat aac aat    48
Met Ile Thr Ile Asn Ile Ser Gly Gly Asn Val Thr Ile Asn Asn Asn
  1               5                  10                  15 atc agt tca gta acg gat atc caa aaa ccc ctt gat gca gaa ccc ctc    96
Ile Ser Ser Val Thr Asp Ile Gln Lys Pro Leu Asp Ala Glu Pro Leu
                 20                  25                  30 tca gtc acg aat tat aga gat ctg aca ata gag ccg cac tca tct att   144
Ser Val Thr Asn Tyr Arg Asp Leu Thr Ile Glu Pro His Ser Ser Ile
             35                  40                  45 caa gca gac aga acg gac acc ccc att att cct gaa aca cgc cct gat   192
```

```
                Gln Ala Asp Arg Thr Asp Thr Pro Ile Ile Pro Glu Thr Arg Pro Asp
                    50                  55                  60 tat tat atc gct aac tca ggc cct gct tca tca gtc aaa gct gtg ttt      240
Tyr Tyr Ile Ala Asn Ser Gly Pro Ala Ser Ser Val Lys Ala Val Phe
 65              70                  75                  80 tat tgg tcg cat tcg ttt aca tcg gaa tgg ttc gag tat tca tct atc      288
Tyr Trp Ser His Ser Phe Thr Ser Glu Trp Phe Glu Tyr Ser Ser Ile
                 85                  90                  95 acg gta aaa gca gga gaa gat gga ata tta aaa tca ccg agt aat gct      336
Thr Val Lys Ala Gly Glu Asp Gly Ile Leu Lys Ser Pro Ser Asn Ala
             100                 105                 110 gta tat tac agt aaa gta gtc att tat aat gat aca gat aag cgg gct      384
Val Tyr Tyr Ser Lys Val Val Ile Tyr Asn Asp Thr Asp Lys Arg Ala
         115                 120                 125 ttt gtg act gga tat aac atg taa                                      408
Phe Val Thr Gly Tyr Asn Met
     130                 135
```

<210> 9
<211> 135
<212> PRT
<213> Xenorhabdus poinarii

<400> 9
```
Met Ile Thr Ile Asn Ile Ser Gly Gly Asn Val Thr Ile Asn Asn Asn
 1               5                  10                  15

Ile Ser Ser Val Thr Asp Ile Gln Lys Pro Leu Asp Ala Glu Pro Leu
             20                  25                  30

Ser Val Thr Asn Tyr Arg Asp Leu Thr Ile Glu Pro His Ser Ser Ile
         35                  40                  45

Gln Ala Asp Arg Thr Asp Thr Pro Ile Ile Pro Glu Thr Arg Pro Asp
     50                  55                  60

Tyr Tyr Ile Ala Asn Ser Gly Pro Ala Ser Ser Val Lys Ala Val Phe
 65                  70                  75                  80

Tyr Trp Ser His Ser Phe Thr Ser Glu Trp Phe Glu Tyr Ser Ser Ile
                 85                  90                  95

Thr Val Lys Ala Gly Glu Asp Gly Ile Leu Lys Ser Pro Ser Asn Ala
             100                 105                 110

Val Tyr Tyr Ser Lys Val Val Ile Tyr Asn Asp Thr Asp Lys Arg Ala
         115                 120                 125

Phe Val Thr Gly Tyr Asn Met
     130                 135
```

<210> 10
<211> 1056
<212> DNA
<213> Xenorhabdus poinarii

<220>
<221> CDS
<222> (1)..(1053)

<223> JHE-like orf2 of pCIB9354

<400> 10

| | | | | | | | | | | | | | | | | |
|---|---|---|---|---|---|---|---|---|---|---|---|---|---|---|---|---|
| atg | aat | aat | agt | cca | atg | aat | gat | cag | tta | tca | aca | gcg | cct | tat | tca | 48 |
| Met | Asn | Asn | Ser | Pro | Met | Asn | Asp | Gln | Leu | Ser | Thr | Ala | Pro | Tyr | Ser | |
| 1 | | | | 5 | | | | | 10 | | | | | 15 | | |
| att | tcg | aca | ccc | aat | tat | gaa | tgg | gat | atg | tca | tca | atc | ata | aaa | gat | 96 |
| Ile | Ser | Thr | Pro | Asn | Tyr | Glu | Trp | Asp | Met | Ser | Ser | Ile | Ile | Lys | Asp | |
| | | | 20 | | | | | 25 | | | | | 30 | | | |
| gcc | att | atc | ggt | ggc | ata | gga | ttt | att | ccc | gga | cca | ggc | cct | gca | atc | 144 |
| Ala | Ile | Ile | Gly | Gly | Ile | Gly | Phe | Ile | Pro | Gly | Pro | Gly | Pro | Ala | Ile | |
| | | 35 | | | | | 40 | | | | | 45 | | | | |
| tct | ttt | tta | tta | gga | ctg | ttc | tgg | cca | caa | cag | aca | gac | aat | acc | tgg | 192 |
| Ser | Phe | Leu | Leu | Gly | Leu | Phe | Trp | Pro | Gln | Gln | Thr | Asp | Asn | Thr | Trp | |
| | 50 | | | | | 55 | | | | | 60 | | | | | |
| gat | caa | atc | ctc | caa | aaa | atc | gaa | caa | atg | ata | gaa | gaa | gcg | aat | tta | 240 |
| Asp | Gln | Ile | Leu | Gln | Lys | Ile | Glu | Gln | Met | Ile | Glu | Glu | Ala | Asn | Leu | |
| 65 | | | | | 70 | | | | | 75 | | | | | 80 | |
| aaa | acc | att | aaa | ggt | ata | tta | aat | gga | gat | ata | caa | gaa | att | aaa | gga | 288 |
| Lys | Thr | Ile | Lys | Gly | Ile | Leu | Asn | Gly | Asp | Ile | Gln | Glu | Ile | Lys | Gly | |
| | | | | 85 | | | | | 90 | | | | | 95 | | |
| aaa | atg | gac | cat | gtg | aaa | tct | atg | cta | gag | aat | tct | cct | ggc | agc | cag | 336 |
| Lys | Met | Asp | His | Val | Lys | Ser | Met | Leu | Glu | Asn | Ser | Pro | Gly | Ser | Gln | |
| | | | 100 | | | | | 105 | | | | | 110 | | | |
| gaa | agc | cat | gat | gct | tat | atg | ttt | ctg | gca | agg | ttt | ttg | gtc | agt | att | 384 |
| Glu | Ser | His | Asp | Ala | Tyr | Met | Phe | Leu | Ala | Arg | Phe | Leu | Val | Ser | Ile | |
| | | 115 | | | | | 120 | | | | | 125 | | | | |
| gat | gaa | aaa | ttc | aaa | tct | ttc | gat | gat | aga | aca | aat | tat | caa | att | ctt | 432 |
| Asp | Glu | Lys | Phe | Lys | Ser | Phe | Asp | Asp | Arg | Thr | Asn | Tyr | Gln | Ile | Leu | |
| | 130 | | | | | 135 | | | | | 140 | | | | | |
| ccc | atg | tac | acg | aat | aca | att | atg | tta | caa | gcg | cct | tat | tgg | aaa | atg | 480 |
| Pro | Met | Tyr | Thr | Asn | Thr | Ile | Met | Leu | Gln | Ala | Pro | Tyr | Trp | Lys | Met | |
| 145 | | | | | 150 | | | | | 155 | | | | | 160 | |
| ggc | atc | gaa | aag | aaa | gag | gat | atc | ggt | tta | acc | gat | att | gaa | gtt | ggt | 528 |
| Gly | Ile | Glu | Lys | Lys | Glu | Asp | Ile | Gly | Leu | Thr | Asp | Ile | Glu | Val | Gly | |
| | | | | 165 | | | | | 170 | | | | | 175 | | |
| gaa | tta | aaa | gaa | ctt | atc | gat | aaa | tta | tat | act | aaa | tca | tat | gat | tat | 576 |
| Glu | Leu | Lys | Glu | Leu | Ile | Asp | Lys | Leu | Tyr | Thr | Lys | Ser | Tyr | Asp | Tyr | |
| | | | 180 | | | | | 185 | | | | | 190 | | | |
| atc | aat | aat | acg | tat | aat | cgt | gaa | tat | aat | aat | gca | atc | aat | acg | tca | 624 |
| Ile | Asn | Asn | Thr | Tyr | Asn | Arg | Glu | Tyr | Asn | Asn | Ala | Ile | Asn | Thr | Ser | |
| | | 195 | | | | | 200 | | | | | 205 | | | | |
| acc | gca | gag | agt | atc | acc | aat | aat | tta | ttg | tct | gtc | aga | gga | tat | tgt | 672 |
| Thr | Ala | Glu | Ser | Ile | Thr | Asn | Asn | Leu | Leu | Ser | Val | Arg | Gly | Tyr | Cys | |
| | 210 | | | | | 215 | | | | | 220 | | | | | |
| tta | tta | cat | ggt | tgt | gaa | tgc | ctt | gaa | gtt | att | gcg | cat | ata | caa | aac | 720 |
| Leu | Leu | His | Gly | Cys | Glu | Cys | Leu | Glu | Val | Ile | Ala | His | Ile | Gln | Asn | |
| 225 | | | | | 230 | | | | | 235 | | | | | 240 | |
| aat | agt | ctt | gat | aaa | ggc | ttc | tac | cct | aaa | acg | atc | agc | tat | tcg | agt | 768 |
| Asn | Ser | Leu | Asp | Lys | Gly | Phe | Tyr | Pro | Lys | Thr | Ile | Ser | Tyr | Ser | Ser | |
| | | | | 245 | | | | | 250 | | | | | 255 | | |

```
gtt ttc gat cgt cct aca aac aaa atg aga att cag gcg ctt aca gaa      816
Val Phe Asp Arg Pro Thr Asn Lys Met Arg Ile Gln Ala Leu Thr Glu
            260                 265                 270 gat gac caa atg caa gaa ccg ttc aaa cct tct ttc gtc aat ggt caa      864
Asp Asp Gln Met Gln Glu Pro Phe Lys Pro Ser Phe Val Asn Gly Gln
        275                 280                 285 tat aat aaa ata aaa tca ttg gag ggt tat gtc aca agg atc ggc aat      912
Tyr Asn Lys Ile Lys Ser Leu Glu Gly Tyr Val Thr Arg Ile Gly Asn
    290                 295                 300 gcc ccc cga gtc ggc gga att aaa atc aca ttt gaa aac aac gca tct      960
Ala Pro Arg Val Gly Gly Ile Lys Ile Thr Phe Glu Asn Asn Ala Ser
305                 310                 315                 320 tat act ctt ggc act gta act tca gaa aca acc tct att gaa ctc aat     1008
Tyr Thr Leu Gly Thr Val Thr Ser Glu Thr Thr Ser Ile Glu Leu Asn
                325                 330                 335 gag agt gtt ata acc agc ata gaa gtg tgg gga gag tgg tgc cgt tga     1056
Glu Ser Val Ile Thr Ser Ile Glu Val Trp Gly Glu Trp Cys Arg
            340                 345                 350
```

<210> 11
<211> 351
<212> PRT
<213> Xenorhabdus poinarii

<400> 11

Met Asn Asn Ser Pro Met Asn Asp Gln Leu Ser Thr Ala Pro Tyr Ser
 1               5                  10                  15

Ile Ser Thr Pro Asn Tyr Glu Trp Asp Met Ser Ser Ile Ile Lys Asp
                20                  25                  30

Ala Ile Ile Gly Gly Ile Gly Phe Ile Pro Gly Pro Gly Pro Ala Ile
            35                  40                  45

Ser Phe Leu Leu Gly Leu Phe Trp Pro Gln Gln Thr Asp Asn Thr Trp
        50                  55                  60

Asp Gln Ile Leu Gln Lys Ile Glu Gln Met Ile Glu Glu Ala Asn Leu
65                  70                  75                  80

Lys Thr Ile Lys Gly Ile Leu Asn Gly Asp Ile Gln Glu Ile Lys Gly
                85                  90                  95

Lys Met Asp His Val Lys Ser Met Leu Glu Asn Ser Pro Gly Ser Gln
            100                 105                 110

Glu Ser His Asp Ala Tyr Met Phe Leu Ala Arg Phe Leu Val Ser Ile
        115                 120                 125

Asp Glu Lys Phe Lys Ser Phe Asp Asp Arg Thr Asn Tyr Gln Ile Leu
130                 135                 140

Pro Met Tyr Thr Asn Thr Ile Met Leu Gln Ala Pro Tyr Trp Lys Met
145                 150                 155                 160

Gly Ile Glu Lys Lys Glu Asp Ile Gly Leu Thr Asp Ile Glu Val Gly
                165                 170                 175

Glu Leu Lys Glu Leu Ile Asp Lys Leu Tyr Thr Lys Ser Tyr Asp Tyr

```
                       180                     185                       190
Ile Asn Asn Thr Tyr Asn Arg Glu Tyr Asn Asn Ala Ile Asn Thr Ser
            195                     200                 205

Thr Ala Glu Ser Ile Thr Asn Asn Leu Leu Ser Val Arg Gly Tyr Cys
        210                     215                 220

Leu Leu His Gly Cys Glu Cys Leu Glu Val Ile Ala His Ile Gln Asn
225                     230                     235                 240

Asn Ser Leu Asp Lys Gly Phe Tyr Pro Lys Thr Ile Ser Tyr Ser Ser
                245                     250                 255

Val Phe Asp Arg Pro Thr Asn Lys Met Arg Ile Gln Ala Leu Thr Glu
            260                     265                 270

Asp Asp Gln Met Gln Glu Pro Phe Lys Pro Ser Phe Val Asn Gly Gln
        275                     280                 285

Tyr Asn Lys Ile Lys Ser Leu Glu Gly Tyr Val Thr Arg Ile Gly Asn
    290                     295                 300

Ala Pro Arg Val Gly Gly Ile Lys Ile Thr Phe Glu Asn Asn Ala Ser
305                     310                     315                 320

Tyr Thr Leu Gly Thr Val Thr Ser Glu Thr Thr Ser Ile Glu Leu Asn
                325                     330                 335

Glu Ser Val Ile Thr Ser Ile Glu Val Trp Gly Glu Trp Cys Arg
            340                     345                 350
```

<210> 12
<211> 408
<212> DNA
<213> Photorhabdus luminescens

<220>
<221> CDS
<222> (1)..(405)
<223> orf1 of pCIB9383-21

<400> 12
```
atg att aca atc aat atc act ggt gat aat gta aga gtt aat aac aat    48
Met Ile Thr Ile Asn Ile Thr Gly Asp Asn Val Arg Val Asn Asn Asn
 1               5                  10                  15 ata gca aca gaa acc gac ctc caa aat aca cct gct tca gca ccc tta    96
Ile Ala Thr Glu Thr Asp Leu Gln Asn Thr Pro Ala Ser Ala Pro Leu
             20                  25                  30 tca att att aat ttt agg gat atg aca ata gaa cct cat tca tct gtt   144
Ser Ile Ile Asn Phe Arg Asp Met Thr Ile Glu Pro His Ser Ser Val
         35                  40                  45 gag gcg ata aga acc gat aca ccg att att cct gaa tca cga cca aat   192
Glu Ala Ile Arg Thr Asp Thr Pro Ile Ile Pro Glu Ser Arg Pro Asn
     50                  55                  60 tac tat gtt gct aat tct ggc ccg gcc tca tca gtc aga gct gtt ttc   240
Tyr Tyr Val Ala Asn Ser Gly Pro Ala Ser Ser Val Arg Ala Val Phe
 65                  70                  75                  80 tat tgg tcc cac tct ttt aca tca gaa tgg ttt gaa tct tcc tct att   288
Tyr Trp Ser His Ser Phe Thr Ser Glu Trp Phe Glu Ser Ser Ser Ile
```

```
                     85                    90                    95
att gta aaa gca ggc gaa gac gga gtc tta cat tca ccg ggt aat tct    336
Ile Val Lys Ala Gly Glu Asp Gly Val Leu His Ser Pro Gly Asn Ser
            100                 105                 110 tta tat tac agc aag gtt gta att tat aac gat aca gac aaa cgt gct    384
Leu Tyr Tyr Ser Lys Val Val Ile Tyr Asn Asp Thr Asp Lys Arg Ala
            115                 120                 125 ttt gtt acc ggc tac aat cta taa                                    408
Phe Val Thr Gly Tyr Asn Leu
            130             135

<210> 13
<211> 135
<212> PRT
<213> Photorhabdus luminescens

<400> 13
Met Ile Thr Ile Asn Ile Thr Gly Asp Asn Val Arg Val Asn Asn Asn
  1               5                  10                  15

Ile Ala Thr Glu Thr Asp Leu Gln Asn Thr Pro Ala Ser Ala Pro Leu
              20                  25                  30

Ser Ile Ile Asn Phe Arg Asp Met Thr Ile Glu Pro His Ser Ser Val
              35                  40                  45

Glu Ala Ile Arg Thr Asp Thr Pro Ile Ile Pro Glu Ser Arg Pro Asn
          50                  55                  60

Tyr Tyr Val Ala Asn Ser Gly Pro Ala Ser Ser Val Arg Ala Val Phe
 65                  70                  75                  80

Tyr Trp Ser His Ser Phe Thr Ser Glu Trp Phe Glu Ser Ser Ser Ile
              85                  90                  95

Ile Val Lys Ala Gly Glu Asp Gly Val Leu His Ser Pro Gly Asn Ser
             100                 105                 110

Leu Tyr Tyr Ser Lys Val Val Ile Tyr Asn Asp Thr Asp Lys Arg Ala
             115                 120                 125

Phe Val Thr Gly Tyr Asn Leu
             130             135

<210> 14
<211> 1320
<212> DNA
<213> Photorhabdus luminescens

<220>
<221> CDS
<222> (1)..(1317)
<223> JHE-like orf2 of pCIB9383-21

<400> 14
atg aat aat gaa ccg atg aat act aat gaa tca caa gct tca gag ata    48
Met Asn Asn Glu Pro Met Asn Thr Asn Glu Ser Gln Ala Ser Glu Ile
  1               5                  10                  15 gta ccc tca atg aat gaa tct ata tta aat gaa tct ata tta aat gaa    96
Val Pro Ser Met Asn Glu Ser Ile Leu Asn Glu Ser Ile Leu Asn Glu
```

```
                    20                          25                          30
tct ata tta gca gca cct tat tca att tct aca cct aat tat gaa tgg    144
Ser Ile Leu Ala Ala Pro Tyr Ser Ile Ser Thr Pro Asn Tyr Glu Trp
        35                      40                      45 gat atg tca tca ata ata aaa gat gcc att att ggt ggt ata ggc ttt    192
Asp Met Ser Ser Ile Ile Lys Asp Ala Ile Ile Gly Gly Ile Gly Phe
    50                      55                      60 att cct ggt ccg ggc tca gca ata tca ttt ttg tta ggg tta ttt tgg    240
Ile Pro Gly Pro Gly Ser Ala Ile Ser Phe Leu Leu Gly Leu Phe Trp
65                      70                      75                  80 cca caa caa acc gac aat act tgg gag caa att ctc caa aaa gta gaa    288
Pro Gln Gln Thr Asp Asn Thr Trp Glu Gln Ile Leu Gln Lys Val Glu
                85                      90                      95 caa atg atc gag caa gcc aat ctc aaa act att caa gga ata ttg aac    336
Gln Met Ile Glu Gln Ala Asn Leu Lys Thr Ile Gln Gly Ile Leu Asn
            100                     105                     110 ggc gat ata caa gaa att aaa ggc aaa atg gaa cat gtg caa ttc atg    384
Gly Asp Ile Gln Glu Ile Lys Gly Lys Met Glu His Val Gln Phe Met
            115                     120                     125 cta gaa tcc tca cct ggc act caa gaa agc cat gac gca tac atg ttt    432
Leu Glu Ser Ser Pro Gly Thr Gln Glu Ser His Asp Ala Tyr Met Phe
130                     135                     140 ctg gcg aga tat ctg gtc agt ata gac gaa aaa ttc aag tct ttt gat    480
Leu Ala Arg Tyr Leu Val Ser Ile Asp Glu Lys Phe Lys Ser Phe Asp
145                     150                     155                 160 aac aaa aca aat tat caa att ctt ccc atg tat acc aat acg att atg    528
Asn Lys Thr Asn Tyr Gln Ile Leu Pro Met Tyr Thr Asn Thr Ile Met
                165                     170                     175 tta caa gcc cct tat tgg aaa atg ggt ata gag aga aaa gat gag ata    576
Leu Gln Ala Pro Tyr Trp Lys Met Gly Ile Glu Arg Lys Asp Glu Ile
            180                     185                     190 aaa cta aca gat ata gaa gtt aat gaa tta aaa gag ctg ata gga aaa    624
Lys Leu Thr Asp Ile Glu Val Asn Glu Leu Lys Glu Leu Ile Gly Lys
        195                     200                     205 tta tct acc agc gcc gat aaa tat att cat gat gtc tat act cgt gaa    672
Leu Ser Thr Ser Ala Asp Lys Tyr Ile His Asp Val Tyr Thr Arg Glu
210                     215                     220 tat gat aat gcg atg aac act tca aca gca gca aat atc acc aat aat    720
Tyr Asp Asn Ala Met Asn Thr Ser Thr Ala Ala Asn Ile Thr Asn Asn
225                     230                     235                 240 tta tta tct gta aga ggc tat tgt tta tta cat ggt tta gaa tgt ctc    768
Leu Leu Ser Val Arg Gly Tyr Cys Leu Leu His Gly Leu Glu Cys Leu
            245                     250                     255 gaa gtc att aac cat ata caa aat aat agc ctt gag caa agt ttt tat    816
Glu Val Ile Asn His Ile Gln Asn Asn Ser Leu Glu Gln Ser Phe Tyr
            260                     265                     270 cct aaa act atc agc tac tcc acc gta ttc gat cgc cag aca aat aaa    864
Pro Lys Thr Ile Ser Tyr Ser Thr Val Phe Asp Arg Gln Thr Asn Lys
        275                     280                     285
```

```
aca agg gtt caa gcc ctg aca gaa gac gat caa atg caa gag cca ttc    912
Thr Arg Val Gln Ala Leu Thr Glu Asp Asp Gln Met Gln Glu Pro Phe
    290                 295                 300 aag cct gct tta att aat ggg aag tac aac aaa ata aaa tca ttg att    960
Lys Pro Ala Leu Ile Asn Gly Lys Tyr Asn Lys Ile Lys Ser Leu Ile
305                 310                 315                 320 ggg tat gta caa aga atc gga aac gca ccc aga gtt gga ggc att aaa   1008
Gly Tyr Val Gln Arg Ile Gly Asn Ala Pro Arg Val Gly Gly Ile Lys
                325                 330                 335 gtc aca ttt gca aac gat gca tct tat acc ctc ggt aca gta act tca   1056
Val Thr Phe Ala Asn Asp Ala Ser Tyr Thr Leu Gly Thr Val Thr Ser
            340                 345                 350 gaa gta aac tca att gaa ctg aat gac agc gtt ata acc agc ctg gaa   1104
Glu Val Asn Ser Ile Glu Leu Asn Asp Ser Val Ile Thr Ser Leu Glu
        355                 360                 365 gta tgg gga aat ggc gct gtt gat gag gca ttc ttt aca tta agt gac   1152
Val Trp Gly Asn Gly Ala Val Asp Glu Ala Phe Phe Thr Leu Ser Asp
    370                 375                 380 gga cgt caa ttt agg ctt ggc caa cgc tat gcc agt aac tat aga aaa   1200
Gly Arg Gln Phe Arg Leu Gly Gln Arg Tyr Ala Ser Asn Tyr Arg Lys
385                 390                 395                 400 tat gct gtc gat aac cac tat att tca gga ttg tac tta gcc agt gat   1248
Tyr Ala Val Asp Asn His Tyr Ile Ser Gly Leu Tyr Leu Ala Ser Asp
                405                 410                 415 gaa cct tca ttg gca ggt caa gca gca ggc att gca gtt tca tac cat   1296
Glu Pro Ser Leu Ala Gly Gln Ala Ala Gly Ile Ala Val Ser Tyr His
            420                 425                 430 atg ata gct gat aaa aaa tca tag                                   1320
Met Ile Ala Asp Lys Lys Ser
        435
```

<210> 15
<211> 439
<212> PRT
<213> Photorhabdus luminescens

<400> 15

```
Met Asn Asn Glu Pro Met Asn Thr Asn Glu Ser Gln Ala Ser Glu Ile
  1               5                  10                  15

Val Pro Ser Met Asn Glu Ser Ile Leu Asn Glu Ser Ile Leu Asn Glu
             20                  25                  30

Ser Ile Leu Ala Ala Pro Tyr Ser Ile Ser Thr Pro Asn Tyr Glu Trp
         35                  40                  45

Asp Met Ser Ser Ile Ile Lys Asp Ala Ile Ile Gly Gly Ile Gly Phe
     50                  55                  60

Ile Pro Gly Pro Gly Ser Ala Ile Ser Phe Leu Leu Gly Leu Phe Trp
 65                  70                  75                  80

Pro Gln Gln Thr Asp Asn Thr Trp Glu Gln Ile Leu Gln Lys Val Glu
                 85                  90                  95

Gln Met Ile Glu Gln Ala Asn Leu Lys Thr Ile Gln Gly Ile Leu Asn
```

```
                    100                     105                     110
Gly Asp Ile Gln Glu Ile Lys Gly Lys Met Glu His Val Gln Phe Met
            115                 120                 125
Leu Glu Ser Ser Pro Gly Thr Gln Glu Ser His Asp Ala Tyr Met Phe
            130                 135                 140
Leu Ala Arg Tyr Leu Val Ser Ile Asp Glu Lys Phe Lys Ser Phe Asp
145                 150                 155                 160
Asn Lys Thr Asn Tyr Gln Ile Leu Pro Met Tyr Thr Asn Thr Ile Met
                165                 170                 175
Leu Gln Ala Pro Tyr Trp Lys Met Gly Ile Glu Arg Lys Asp Glu Ile
            180                 185                 190
Lys Leu Thr Asp Ile Glu Val Asn Glu Leu Lys Glu Leu Ile Gly Lys
            195                 200                 205
Leu Ser Thr Ser Ala Asp Lys Tyr Ile His Asp Val Tyr Thr Arg Glu
            210                 215                 220
Tyr Asp Asn Ala Met Asn Thr Ser Thr Ala Ala Asn Ile Thr Asn Asn
225                 230                 235                 240
Leu Leu Ser Val Arg Gly Tyr Cys Leu Leu His Gly Leu Glu Cys Leu
                245                 250                 255
Glu Val Ile Asn His Ile Gln Asn Asn Ser Leu Glu Gln Ser Phe Tyr
            260                 265                 270
Pro Lys Thr Ile Ser Tyr Ser Thr Val Phe Asp Arg Gln Thr Asn Lys
            275                 280                 285
Thr Arg Val Gln Ala Leu Thr Glu Asp Asp Gln Met Gln Glu Pro Phe
            290                 295                 300
Lys Pro Ala Leu Ile Asn Gly Lys Tyr Asn Lys Ile Lys Ser Leu Ile
305                 310                 315                 320
Gly Tyr Val Gln Arg Ile Gly Asn Ala Pro Arg Val Gly Gly Ile Lys
                325                 330                 335
Val Thr Phe Ala Asn Asp Ala Ser Tyr Thr Leu Gly Thr Val Thr Ser
            340                 345                 350
Glu Val Asn Ser Ile Glu Leu Asn Asp Ser Val Ile Thr Ser Leu Glu
            355                 360                 365
Val Trp Gly Asn Gly Ala Val Asp Glu Ala Phe Phe Thr Leu Ser Asp
            370                 375                 380
Gly Arg Gln Phe Arg Leu Gly Gln Arg Tyr Ala Ser Asn Tyr Arg Lys
385                 390                 395                 400
Tyr Ala Val Asp Asn His Tyr Ile Ser Gly Leu Tyr Leu Ala Ser Asp
                405                 410                 415
Glu Pro Ser Leu Ala Gly Gln Ala Ala Gly Ile Ala Val Ser Tyr His
            420                 425                 430
Met Ile Ala Asp Lys Lys Ser
            435
```

UNITED STATES PATENT AND TRADEMARK OFFICE
CERTIFICATE OF CORRECTION

PATENT NO.       : 6,277,823 B1
APPLICATION NO.  : 09/668648
DATED            : August 21, 2001
INVENTOR(S)      : Kramer et al.

It is certified that error appears in the above-identified patent and that said Letters Patent is hereby corrected as shown below:

Delete Columns 1-48 in printed patent and substitute therefor the attached columns 1-78.

This certificate supersedes the Certificate of Correction issued August 8, 2006.

Signed and Sealed this

Eighth Day of July, 2008

JON W. DUDAS
*Director of the United States Patent and Trademark Office*

INSECTICIDAL TOXINS AND NUCLEIC ACID SEQUENCES CODING THEREFOR

This application is a division of U.S. application Ser. No. 09/293,395, filed Apr. 16, 1999 U.S. Pat. No. 6,174,860, which claims the benefit of U.S. Provisional Application No. 60/145,148, filed Apr. 21, 1998, U.S. Provisional Application No. 60/123,500, filed Mar. 9, 1999; and U.S. Provisional Application No. 60/125,525, filed Mar. 22, 1999. The disclosure of each the aforementioned application is hereby expressing incorporated by reference in its entirety into the instant disclosure.

FIELD OF THE INVENTION

The invention relates to novel toxins from *Xenorhabdus nematophilus*, *Xenorhabdus poinarii*, and *Photorhabdus luminescens*, nucleic acid sequences whose expression results in said toxins, said methods of making and methods of using the toxins and corresponding nucleic acid sequences to control insects.

BACKGROUND OF THE INVENTION

Insect pests are a major causes of crop losses. Solely in the U.S., about $7.7 billion are lost every year due to infestation by various genera of insects. In addition to losses in field crops, insect pests are also a burden to vegetable and fruit growers, to producers of ornamental flowers, and they are a nuisance to gardeners and home owners.

Insect pests are mainly controlled by intensive applications of chemical insecticides, which are active through inhibition of insect growth, prevention of insect feeding or reproduction, or death of the insects. Good insect control can thus be reached, but these chemicals can sometimes also affect other, beneficial insects. Another problem resulting from the wide use of chemical pesticides is the appearance of resistant insect varieties. This has been partially alleviated by various resistance management strategies, but there is an increasing need for alternative pest control agents. Biological insect control agents, such as *Bacillus thuringiensis* strains expressing insecticidal toxins like δ-endotoxins, have also been applied with satisfactorily results, offering an alternative or a complement to chemical insecticides. Recently, the genes coding for some of these δ-endotoxins have been isolated and their expression in heterologous hosts have been shown to provide another tool for the control of economically important insect pests. In particular, the expression of insecticidal toxins in transgenic plants, such as *Bacillus thuringiensis* δ-endotoxins, has provided efficient projection against selected insect pests, and transgenic plants expressing such toxins have been commercialized, allowing farmers to reduce applications of chemical insect control agents. Yet, even in this case, the development of resistance remains a possibility and only a few specific insect pests are controllable. Consequently, there remains a long-felt but unfulfilled need to discover new and effective insect control agents that provide an economic benefit to farmers and that are environmentally acceptable.

SUMMARY OF THE INVENTION

The present invention addresses the long-standing need for novel insect control agents. Particularly needed are control agents that are targeted to economically important insect pests and that efficiently control insect strains resistant to existing insect control agents. Furthermore, agents whose application minimizes the burden on the environment are desirable.

In the search for novel insect control agents, certain classes of nematodes from the genera *Heterorhabdus* and *Steinernema* are of particular interest because of their insecticidal properties. They kill insect larvae and their offspring feed in the dead larvae. Indeed, the insecticidal activity is due to symbiotic bacteria living in the nematodes. These symbiotic bacteria are *Photorhabdus* in the case of *Heterorhabdus* and *Xenorhabdus* in the case of *Steinernema*.

The present invention is drawn to nucleotide sequences isolated from *Xenorhabdus nematophilus*, and nucleotide sequences substantially similar thereto, whose expression result in insecticidal toxins that are highly toxic to economically important pests, particularly plant pests. The invention is further drawn to the insecticidal toxin resulting from the expression of the nucleotide sequence, and to compositions and formulations containing the insecticidal toxin, that are capable of inhibiting the ability of insect pests to survive, grow or reproduce, or of limiting insect-related damage or loss in crop plants. The invention is further drawn to a method of making the toxin and to methods of using the nucleotide sequence, for example in microorganisms to control insects or in transgenic plants to confer insect resistance, and to a method of using the toxin, and compositions and formulations comprising the toxin, for example applying the toxin, composition or formulation to insect infested areas, or to prophylactically treat insect susceptible areas or plants to confer protection or resistance against harmful insects.

The novel toxin is highly insecticidal against *Plutella xylostella* (diamondback moth), an economically important insect pest. The toxin can be used in multiple insect control strategies, resulting in maximal efficiency with minimal impact on the environment.

According to one aspect, the present invention provides an isolated nucleic acid molecule comprising: (a) a nucleotide sequence substantially similar to a nucleotide sequence selected from the group consisting of: nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14; or (b) a nucleotide sequence isocoding with the nucleotide sequence of (a); wherein expression of said nucleic acid molecule results in at least one toxin that is active against insects. In one embodiment of this aspect, the nucleotide sequence is isocoding with a nucleotide sequence substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. Preferably, the nucleotide sequence is substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. More preferably, the nucleotide sequence encodes an amino acid sequence selected from the group consisting of SEQ ID NOs:2, 3, 5, 7, 9, 11, 13, and 15. Most preferably, the nucleotide sequence comprises nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. In another embodiment, the nucleotide sequence comprises the approximately 3.0 kb DNA fragment comprised in pCIB9369 (NRRL B-21883).

According to a preferred embodiment, the toxins resulting from expression of the nucleic acid molecules of the invention have activity against *Plutella xylostella*.

In another aspect, the present invention provides an isolated nucleic acid molecule comprising a 20, 25, 30, 35, 40, 45, or 50 (preferably 20) base pair nucleotide portion identical in sequence to a respective consecutive 20, 25, 30, 35, 40, 45, or 50 (preferably 20) base pair nucleotide portion of a nucleotide sequence selected from the group consisting of: nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14, wherein expression of said nucleic acid molecule results in at least one toxin that is active against insects.

The present invention also provides a chimeric gene comprising a heterologous promoter sequence operatively linked to a nucleic acid molecule of the invention. Further, the present invention provides a recombinant vector comprising such a chimeric gene. Still further, the present invention provides a host cell comprising such a chimeric gene. A host cell according to this aspect of the invention may be a bacteril cell, a yeast cell, or a plant cell, preferably a plant cell. Even further, the present invention provides a plant comprising such a plant cell. Preferably, the plant is maize.

In yet another aspect, the present invention provides toxins produced by the expression of DNA molecules of the present invention. According to a preferred embodiment, the toxins of the invention have activity against *Plutella xylostella*.

In one embodiment, the toxins are produced by the *E. coli* strain designated as NRRL accession number B-21883.

In another embodiment, a toxin of the invention comprises an amino acid sequence selected from the group consisting of: SEQ ID NOs:2, 3, 5, 7, 9, 11, 13, and 15.

The present invention also provides a composition comprising an insecticidally effective amount of a toxin according to the invention.

In another aspect, the present invention provides a method of producing a toxin that is active against insects, comprising: (a) obtaining a host cell comprising a chimeric gene, which itself comprises a heterologous promoter sequence operatively linked to the nucleic acid molecule of the invention; and (b) expressing the nucleic acid molecule in the cell, which results in at least one toxin that is active against insects.

In a further aspect, the present invention provides a method of producing an insect-resistant plant, comprising introducing a nucleic acid molecule of the invention into the plant, wherein the nucleic acid molecule is expressible in the plant in an effective amount to control insects. According to a preferred embodiment, the insects are *Plutella xylostella*.

In a still further aspect, the present invention provides a method of controlling insects comprising delivering to the insects an effective amount of a toxin according to the present invention. According to a preferred embodiment, the insects are *Plutella xylostella*. Preferably, the toxin is delivered to the insects orally.

Yet another aspect of the present invention is the provision of a method for mutagenizing a nucelic acid molecule according to the present invention, wherein the nucleic acid molecule has been cleaved into population of double-stranded random fragments of a desired size, comprising: (a) adding to the population of double-stranded random fragments one or more single- or double-stranded oligonucleotides, wherein the oligonucleotides each comprise an area of identity and an area of heterology to a double-stranded template polynucleotide; (b) denaturing the resultant mixture of double-stranded random fragments and oligonucleotides into single-stranded fragments; (c) incubating the resultant population of single-stranded fragments with a polymerase under conditions which result in the annealing of the single-stranded fragments at the areas of identity to form pairs of annealed fragments, the areas of identity being sufficient for one member of a pair to prime replication of the other, thereby forming a mutagenized double-stranded polynucleotide; and (d) repeating the second and third steps for at least two further cycles, wherein the resultant mixture in the second step of a further cycle includes the mutagenized double-stranded polynucleotide from the third step of the previous cycle, and wherein the further cycle forms a further mutagenized double-stranded polynucleotide.

Other aspects and advantages of the present invention will become apparent to those skilled in the art from a study of the following description of the invention and non-limiting examples.

DEFINITIONS

"Activity" of the toxins of the invention is meant that the toxins function as orally active insect control agents, have a toxic effect, or are able to disrupt or deter insect feeding, which may or may not cause death of the insect. When a toxin of the invention is delivered to the insect, the result is typically death of the insect, or the insect does not feed upon the source that makes the toxin available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid and sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper transition of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterogous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copiers of a naturally occurring nucelic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-invasive environment such as, for example, a recombinant host cell.

A "nucleic acid molecule" or "nucleic acid sequence" is a linear segment of single- or double-stranded DNA or RNA that can be isolated from any source. In the context of the present invention, the nucleic acid molecule is preferably a segment of DNA. "ORF" means upon reading frame.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, culture in plant tissues, pollen, pollen tubes, ovules, embryo, sacs, zygotes and embryos at various stages of development.

"Plant material" refers to leaves, stems, roots, flowers of flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue cultures and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only charges in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90% more preferably at least 95%, still more preferably at least 99%. A nucleotide sequence "substantially similar" to reference nucleotide sequence hybrids to the reference nucleotide sequence in 7% sodium dodecyl sulfate (SDS), 0.5 M $NaPO_4$, 1 mM EDTA at 50° C. with washing in 2× SSC, 0.1% SDS at 50° C., more desirably in 7% sodium dodecyl sulfate (SDS), 0.5 M $NaPO_4$, 1 mM EDTA at 50° C. with washing in 1× SSC, 0.1% SDS at 50° C., more desirably still in 7% sodium dodecyl sulfate (SDS), 0.5 M $NaPO_4$, 1 mM EDTA at 50° C. with washing in 0.5× SSC, 0.1% SDS at 50° C., preferably in 7% sodium dodecyl sulfate (SDS), 0.5 M $NaPO_4$, 1 mM EDTA at 50° C. with washing in 0.1× SSC, 0.1% SDS at 50° C., more preferably in 7% sodium dodecyl sulfate (SDS), 0.5 M $NaPO_4$, 1 mM EDTA at 50° C. with washing in 0.1× SSC, 0.1% SDS at 65° C.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

BRIEF DESCRIPTION OF THE SEQUENCES IN THE SEQUENCE LISTING

SEQ ID NO:1 is the sequence of the approximately 3.0 kb DNA fragment comprised in *Xenorhabdus nematophilus* clone pCIB9369, which comprises the following ORFs at the specified nucleotide positions:

| Name | Start | End |
|---|---|---|
| orf1 | 569 | 979 |
| orf2 | 1045 | 2334 |

SEQ ID NO:2 is the sequence of the ~15 kDa protein encoded by orf1 of clone pCIB9369.

SEQ ID NO:3 is the sequence of the ~47.7 kDa Juvenile Hormone Esterase-like protein encoded by orf2 of clone pCIB9369.

SEQ ID NO:4 is the DNA sequence of orf1 of *Xenorhabdus nematophilus* clone pCIB9381.

SEQ ID NO:5 is the sequence of the protein encoded by orf1 of clone pCIB9381.

SEQ ID NO:6 is the DNA sequence of orf2 of *Xenorhabdus nematophilus* clone pCIB9381.

SEQ ID NO:7 is the sequence of the Juvenile Hormone Esterase-like protein encoded by orf2 of clone pCIB9381.

SEQ ID NO:8 is the DNA sequence of orf1 of *Xenorhabdus poinarii* clone pCIB9354.

SEQ ID NO:9 is sequence of the protein encoded by orf1 of clone pCIB9354.

SEQ ID NO:10 is the DNA sequence of orf2 of *Xenorhabdus poinarii* clone pCIB9354.

SEQ ID NO:11 is the sequence of the Juvenile Hormone Esterase-like protein encoded by orf2 of clone pCIB9354.

SEQ ID NO:12 is the DNA sequence of orf1 of *Photorhabdus luminescens* clone pCIB9383-21.

SEQ ID NO:13 is the sequence of the protein encoded by orf1 of clone pCIB9383-21.

SEQ ID NO:14 is the DNA sequence of orf2 of *Photorhabdus luminescens* clone pCIB9383-21.

SEQ ID NO:15 is the sequence of the Juvenile Hormone Esterase-like protein encoded by orf2 of clone pCIB9383-21.

DEPOSITS

The following material has been deposited with the Agriculture Research Service, Patent Culture Collection (NRRL), 1815 North University Street, Peoria, Ill. 61604, under the terms of the Budapest Treaty on the International Recognition of the Deposit of Microorganisms for the Purpose of Patent Procedure. All restrictions on the availability of the terms of the Budapest Treaty on the International Recognition of the Deposit of Microorganisms for the Purposes of Patent Procedure. All restrictions on the availability of the deposited material will be irrevocably removed upon the granting of a patent.

| Clone | Accession Number | Date of Deposit |
|---|---|---|
| pCIB9369 | NRRL B-21883 | Nov. 12, 1997 |
| pCIB9354 | NRRL B-30109 | Feb. 25, 1999 |
| pCIB9381 | NRRL B-30110 | Feb. 25, 1999 |
| pCIB9383-21 | NRRL B-30111 | Feb. 25, 1999 |

DETAILED DESCRIPTION OF THE INVENTION

Novel Nucleic Acid Sequences whose Expression Results in Insecticidal Toxins

This invention relates to nucleic acid sequences whose expression results in novel toxins, and to the making and using of the toxins to control insect pests. The nucleic acid sequences are isolated from *Xenorhabdus nematophilus*, *Xenorhabdus poinarii*, and *Photorhabdus luminescens*, members of the *Enterobacteriaceae* family. *Xenorhabdus* are symbiotic bacteria of nematodes of the genus *Steinernema*. *Photorhabdus* are symbiotic bacteria of nematodes of the genus *Heterorhabditis*. The nematodes colonize insect larva, kill them, and their offspring feed on the dead larvae. The insecticidal activity is actually produced by the symbiotic *Xenorhabdus* and *Photorhabdus* bacteria. The inventors are the first to isolate the nucleic acid sequences of the present invention. The expression of the nucleic acid sequences of the present invention results in toxins that can be used to control Lepidopteran insects such as *Plutella xylostella* (Diamondback Moth).

A nucleotide sequence of the present invention in clone pCIB9369 is characterized by an approximately 3.0 kb DNA fragment deposited pursuant to the Budapest Treaty for Patent Deposits under Accession Number NRRL B-21883.

The sequence of this DNA fragment is set forth in SEQ ID NO:1. Two open reading frames (ORF) are present in SEQ ID NO:1 (nucleotides 569–979 and nucleotides 1045–2334, respectively), coding for proteins of predicted sizes of 15 kDa and 47.7 kDa (SEQ ID NOs:2 and 3, respectively). The two ORFs are arranged in an operon-like structure. A search for known sequences showing homology to each individual ORF using the UWGCG Blast and Gap programs does not reveal any significant match for ORF #1 and reveals 21% identity between ORF #2 and *Bacillus thuringensis* cry3A protein, which is not considered to be significant in the art. A Gap analysis of the protein encoded by ORF #2 of pCIB9369 by the Blast program identifies 30.6% AA identity and 44.1% AA similarity to a juvenile hormone esterase-related protein (GenBank accession 2921553; Henikoff et al., *PNAS USA* 89: 10915–10919 (1992)). The nucleotide sequence of the present invention is also compared to known *Xenorhabdus nematophilus* sequences encoding the insecticidal toxin tnxb4 (WO 95/00647), but no significant homology is found. The 3.0 kb DNA fragment is also compared to the nucleotide sequence published in WO 98/08388. Twenty-two sequences of 60 nucleotides each (60-mers) from the 38.2 kb DNA fragment described in WO 98/08388 are compared to the 3.0 kb DNA fragment of the present invention using the UWGCG Gap program. The nucleotide sequence of the first 60-mer starts at base 1 of the 38.2 kb DNA fragment and the other 60-mers are located at approximately 2.0 kb intervals. Each of the 22 sequences as well as their complementary sequences are tested. The highest percent of identity between the 3.0 kb DNA fragment of the present invention and one of these 60-mers in 53%, which is not a significant homology. Furthermore, five different DNA fragments of the 38.2 kb sequence are tested for hybridization to the 3.0 kb fragment of the present invention by Southern blot analysis. None of them reveal a positive hybridization signal.

The nucleotide sequences of pCIB9381, pCIB9354, and pCIB9383-21 also reveal two open reading frames in each of these clones. The nucleotide sequences of the two ORFs in each of pCIB9381 and pCIB9383-21 are highly homologous to those in pCIB9369. Hence, the ORF#2 proteins of pCIB9381 and pCIB9383-21 have essentially the same homology to the juvenile hormone esterase-related protein as does the ORF #2 protein of pCIB9369. The nucleotide sequence of ORF #1 of pCIB9354 is 77% identical to the nucleotide sequence of ORF #1 of pCIB9369, and the nucleotide sequence of ORF #2 of pCIB9354 is 79% identical to the nucleotide sequence of ORF #2 of pCIB9369. The ORF #2 protein of pCIB9354 also has homology to the juvenile hormone esterase-related protein (29.2% AA identity and 42.2% AA similarity).

In a preferred embodiment, the invention encompasses a nucleotide sequence substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14, whose expression results in an insecticidal toxin. The present invention also encompasses recombinant vectors comprising the nucleic acid sequences of this invention. In such vectors, the nucleic acid sequences are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In one embodiment, host cells for such vectors are microorganisms, such as bacteria, in particular *E. coli*. In another embodiment, host cells for such recombinant vectors are endophytes or epiphytes. A preferred host cell for such vectors is a eukaryotic cell, such as a yeast, a plant cell, or an insect cell. Plant cells such as maize cells are most preferred host cells. In another preferred embodiment, such vectors are viral vectors and are used for replication of the nucleotide sequences in particular host cells, e.g. insect cells or plant cells. Recombinant vectors are also used for transformation of the nucleotide sequences of this invention into host cells, whereby the nucleotide sequences are stably integrated into the DNA of such host cells. In one such host cells are prokaryotic cells. In a preferred embodiment, such host cells are eukaryotic cells, such as yeast cells, insect cells, or plant cells. In a most preferred embodiment, the host cells are plant cells, such as maize cells.

The nucleotide sequences of the invention can be isolated using the techniques described in the examples below, or by PCR using the sequences set forth in the sequence listing as the basis for constructing PCR primers. For example, oligonucleotides having the sequence of approximately the first and last 20–25 consecutive nucleotides of orf1 of SEQ ID NO:1 (e.g. nucleotides 569–588 and 957–976 of SEQ ID NO:1) can be used as PCR primers to amplify the orf1 coding sequence (nucleotides 569–976 of SEQ ID NO:1) directly from the source strain (*Xenorhabdus nematophilus* strain ATCC 19061). The other gene sequences of the invention can likewise be amplified by PCR from the respective source strains using the ends of the coding sequences set forth in the sequence listing as the basis for PCR primers.

In another preferred embodiment, the insecticidal toxins comprise at least one polypeptide encoded by a nucleotide sequence of the invention. The molecular weight of an insecticidal toxin according to the invention is larger than 6,000, as determined by size fractionation experiments. After treatment with proteinase K, only a minimal decrease in insecticidal activity is observed in the insect bioassay, indicating that the insecticidal toxins are substantially resistant to proteinase K treatment. The insecticidal toxins retain their insecticidal activity after being stored at 22° C. or at 4° C. for 2 weeks. They also retains their insecticidal activity after being freeze dried and stored at 22° C. for 2 weeks. The insecticidal toxins are also still active after incubation for 5 minutes at 60° C., but they loses their insecticidal activity after incubation for 5 minutes at 100° C. or 80° C.

In further embodiments, the nucleotide sequences of the invention can be modified by incorporation of random mutations in a technique known as in-vitro recombination or DNA shuffling. This technique is described in Stemmer et al., *Nature* 370: 389–391 (1994) and U.S. Pat. No. 5,605,793, which are incorporated herein by reference. Millions of mutant copies of a nucleotide sequence are produced based on an original nucleotide sequence of this invention and variants with improved properties, such as increased insecticidal activity, enhanced stability, or different specificity or range of target insect pests are recovered. The method encompasses forming a mutagenized double-stranded polynucleotide from a template double-stranded polynucleotide comprising a nucleotide sequence of this invention, wherein the temple double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles.

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, *Xenorhabdus nematophilus*, *Xenorhabdus poinarii*, or *Photorhabdus luminescens* cells comprising modifications of at least one nucleotide sequence of this invention at its chromosomal location are described. Such modifications encompass mutations or deletions of existing regulatory elements, thus leading to altered expression of the nucleotide sequence, or the incorporation of new regulatory elements controlling the expression of the nucleotide sequence. In another embodiment, additional copies of one or more of the nucleotide sequences are added to *Xenorhabdus nematophilus*, *Xenorhabdus poinarii*, or *Photorhabdus luminescens* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as the virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in-vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colorizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In: Industrial microorganisms: basic and applied molecular genetics, Baltz, Hegeman, and Skatrud eds., American Society for Microbiology, Washington (1993); Dequin & Barre, Biotechnology 12:173–177 (1994); van den Berg et al., Biotechnology 8:135–139 (1990)).

In another preferred embodiment, at least one of the described nucleotide sequences is transferred to and expressed in *Pseudomonas fluorescens* strain CGA267356 (described in the published application EU 0 472 494 and in WO 94/01561) which has biocontrol characteristics. In another preferred embodiment, a nucleotide sequence of the invention is transferred to *Pseudomonas aureofaciens* strain 30–84 which also has biocontrol characteristics. Expression in heterologous biocontrol strains request the selection of vectors appropriate for replication in the chosen host and a suitable choice of promoter. Techniques are well known in the art for expression in gram-negative and gram-positive bacteria and fungi.

Expression of the Nucleotide Sequences in Plant Tissue

In a particularly preferred embodiment at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidoposis*, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least 35% about GC content, preferably more than about 45%, more preferably more than about 50%, and most preferably more than about 60%. Microbial nucleotide sequences which have low GC contents may express poorly in plants due to the existence of ATTA motifs which may destabilize messages, and AATAAA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). In addition, the nucleotide sequences are screened for the existence of illegitimate spice sites that may cause message truncation. All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy).

For efficient initiation of translation, sequences adjacent to the initiating methionine may require modification. For example, they can be modified by the inclusion of sequences known to be effective in plants. Joshi has suggested an appropriate consensus for plants (NAR 15: 6643–6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters shown to be functional in plants. The choice of promoter will vary depending on the temporal and spatial requirements for expression, and also depending on the target species. Thus, expression of the nucleotide sequences of this invention in leaves, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CaMV 35S and 19S promoters. The nucleotide sequences of this invention can also be expressed under the regulation of promoters that are chemically regulated. This enables the insecticidal toxins to be synthesized only when the crop plants are treated with the inducing chemicals. Preferred technology for chemical induction of gene expression is detailed in the published application EP 0 322 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells which need to synthesize the insecticidal toxins to kill the invading insect past. Preferred promoters of this kind include those described by Stanford et al. *Mol. Gen. Genet.* 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12: 579–589 (1989)). A preferred promoter for root specific expression is that described by de Framond (FEBS 290: 103–106 (1991); EP 0 452 269 to Ciba-Geigy). A preferred stem specific promoter is that described in U.S. Pat. No. 5,625,136 (to Ciba-Geigy) and which drives expression of the maize trpA gene.

Especially preferred embodiments of the invention are transgenic plants expressing at least one of the nucleotide sequences of the invention in a root-preferred or root-specific fashion. Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences which have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093–1096 (1986)). For both direct gene transfer and *Agrobacterium*-mediated transfer, transformation is usually (but not necessarily) undertaken with a selectable marker which may provide resistance to an antibiotic (kanamycin, hygromycin or methotrexate) or a herbicide (basta). Examples of such markers are neomycin phosphotransferase, hygromycin phosphotransferase, dihydrofolate reductase, phosphinothricin acetyltransferase, 2, 2-dichloroproprionic acid dehalogenase, acetohydroxyacid synthase, 5-enolpyruvyl-shikimate-phosphate synthase, haloarylnitrilase, protoporhyrinogen oxidase, acetyl-coenzyme A carboxylase, dihydropteroate synthase, chloramphenicol acetyl transferase, and β-glucuronidase. The choice of selectable or screenable marker for plant transformation is not, however, critical to the invention.

The recombinant DNA described above can be introduced into the plant cell in a number of art-recognized ways. Those skilled in the art will appreciate that the choice of method might depend on the type of plant targeted for transformation. Suitable methods of transforming plant cells include microinjection (Crossway et al., *BioTechniques* 4:320–334 (1986)), electroporation (Riggs et al., *Proc. Nat. Acad. Sci. USA* 83:5602–5606 (1986), *Agrobacterium*-mediated transformation (Hinchee et al., Biotechnology 6:915–921 (1988); See also, Ishida et al., *Nature Biotechnology* 14:745–750 (June 1996) for maize transformation), direct gene transfer (Paszkowski et al., *EMBO J.* 3:2717–2722 (1984); Hayashimoto et al., *Plant Physiol.* 93:857–863 (1990)(rice)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6:923–926 (1988)). See also, Weissinger et al., *Annual Rev. Genet.* 22:421–477 (1988); Sanford et al., *Particulate Science and Technology* 5:27–37 91987)(onion); Svab et al., *Proc. Natl. Acad. Sci. USA* 87: 8526–8530 (1990) (tobacco chloroplast); Christou et al., *Plant Physiol.* 87:671–674 (1988)(soybean); McCabe et al., *Bio/Technology* 6:923–926 (1988)(soybean); Klein et al., *Proc. Natl. Acad. Sci. USA*, 85:4305–4309 (1988)(maize); Klein et al. *Bio/Technology* 6:559–563 (1988) (maize); Klein et al., *Plant Physiol.* 91:440–444 (1988) (maize); Fromm et al., *Bio/Technology* 8:833–839 (1990); and Gordon-Kamm et al., *Plant Cell* 2: 603–618 (1990) (maize); Koziel et al., *Biotechnology* 11: 194–200 (1993) (maize); Shimamoto et al., *Nature* 338: 274–277 (1989) (rice); Christou et al., *Biotechnology* 9: 957–962 (1991) (rice); Datta et al., *Bio/Technology* 8:736–740 (1990) (rice); European Patent Application EP 0 332 581 (orchardgrass and other Pooideae); Vasil et al., *Biotechnology* 11: 1553–1558 (1993) (wheat); Weeks et al., *Plant Physiol.* 102: 1077–1084 (1993) (wheat); Wan et al., *Plant Physiol.* 104: 37–48 (1994) (barley); Jahne et al., *Theor. Appl. Genet.* 89:525–533 (1994)(barley); Umbeck et al., *Bio/Technology* 5: 263–266 (1987) (cotton); Casas et al., *Proc. Natl. Acad. Sci. USA* 90:11212–11216 (Dec. 1993) (sorghum); Somers et al., *Bio/Technology* 10:1589–1594 (Dec. 1992) (oat); Torbet et al., *Plant Cell Reports* 14:635–640 (1995) (oat); Weeks et al., *Plant Physiol.* 102:1077–1084 (1993) (wheat); Chang et al., WO 94/13822 (wheat) and Nehra et al., *The Plant Journal* 5:285–297 (1994) (wheat). A particularly preferred set of embodiments for the introduction of recombinant DNA molecules into maize by microprojectile bombardment can be found in Koziel et al., *Biotechnology* 11: 194–200 (1993), Hill et al., *Euphytica* 85:119–123 (1995) and Koziel et al., *Annals of the New York Academy of Sciences* 792:164–171 (1996). An additional preferred embodiment is the protoplast transformation method for maize as disclosed in EP 0 292 435. Transformation of plants can be undertaken with a single DNA species or multiple DNA species (i.e. co-transformation) and both these techniques are suitable for use with the peroxidase coding sequence.

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastic transformation technology is extensively described in U.S. Plant Nos. 5,451,513, 5,545,817, and 5,545,818, in PCT application no. WO 95/16783, and in McBride et al. (1994) Proc. Natl. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub; J.

M., and Maliga, P. (1992) *Plant Cell* 4, 39–45). This resulted in stable homoplasmic transformants at a frequency of approximately one per 100 bombardments of target leaves. The presence of cloning sites between these markers allowed creation of a plastic targeting vector for introduction of foreign genes (Staub, J. M., and Maliga, P. (1993) *EMBO J.* 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913–917). Previously, this marker had been used successfully for high-frequency transformation of the plastic genome of the green alga *Chlamydomonas reinhardtii* (Goldschmidt-Clermont, M. (1991) *Nucl. Acids. Res.* 19: 4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plasmid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

Formulation of Insecticidal Compositions

The invention also includes compositions comprising at least one of the insecticidal toxins of the present invention. In order to effectively control insect pests such compositions preferably contain sufficient amounts of toxin. Such amounts vary depending on the crop to be protected, on the particular pest to be targeted, and on the environmental conditions, such as humidity, temperature or type or soil. In a preferred embodiment, compositions comprising the insecticidal toxins comprise host cells expressing the toxins without additional purification. In another preferred embodiment, the cells expressing the insecticidal toxins are lyophilized prior to their use as an insecticidal agent. In another embodiment, the insecticidal toxins are engineered to be selected from the host cells. In case where purification of the toxins from the host cells in which they are expressed is desired, various degrees of purification of the insecticidal toxins are reached.

The present invention further embraces the preparation of compositions comprising at least one insecticidal toxin of the present invention, which is homogeneously mixed with one or more compounds or groups of compounds described herein. The present invention also relates to methods of treating plants, which comprise application of the insecticidal toxins or compositions containing the insecticidal toxins, to plants. The insecticidal toxins can be applied to the crop area in the form of compositions or plant to be treated, simultaneously or in succession, with further compounds. These compounds can be both fertilizer or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying insecticidal toxins of the present invention is by spraying to the environmental hosting the insect pest like the soil, water, or foliage of plants. The number of applications and the rate of application depend on the type and intensity of infestation by the insect pest. The insecticidal toxins can also penetrate the plant through the roots via the soil (systemic action) by impregnating the locus of the plant with a liquid composition, or by applying the compounds in solid form to the soil, e.g. in granular form (soil application). The insecticidal toxins may also be applied to seeds (coating) by impregnating the seeds either with a liquid formulation containing insecticidal toxins, or coating them with a solid formulation. In special cases, further types of application are also possible, for example, selective treatment of the plant stems or buds. The insecticidal toxins can also be provided as bait located above or below the ground.

The insecticidal toxins are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances.

The formulations, compositions or preparations containing the insecticidal toxins and, where appropriate, a solid or liquid adjuvant, are prepared in known manner, for example by homogeneously mixing and/or grinding the insecticidal toxins with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohol and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Suitable surface-active compounds are nonionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds.

Suitable soaps are the alkali metals salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, benzimidazole derivatives or alkylarylsulfonates.

The fatty sulfonates or sulfates are usually in the form of alkali metal salts, alkaline earth metal salts or unsubstituted or substituted ammonium salts and have a 8 to 22 carbon alkyl radical which also includes the alkyl moiety or alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of alphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethyoxyethanols, castor oil polyglycol ethers, polypropylene/polyethylene oxide adducts, tributylphenoxypolyethoxyethanol, polyethylene glycol and octylphenoxyethoxyethanol. Fatty and esters of polyoxyethylene sorbitan and polyoxyethylene sorbitan trioleate are also suitable non-ionic surfactants.

Cationic surfactants are preferably quaternary ammonium salts which have, as N-substituent, at least one C8–C22 alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation as described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Procols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

A. Isolation Of Nucleotide Sequences Whose Expression Results in Toxins Active Against Lepidopteran Insects Example 1

Growth of *Xenorhabdus* and *Photorhabdus* Strains

For insect bioassays, the following stains are grown in nutrient broth at 25° C. for 3 days in the growth media recommended by ATCC. For DNA isolation, the cultures are grown for 24 hr under the same conditions.

*Xenorhabdus nematophilus* strain ATCC 19061
*Xenorhabdus nematophilus* strain Ps1 (a USDA isolate)
*Xenorhabdus poinarii* strain ATCC 49122
*Photorhabdus luminescens* strain Ps5 (a USDA isolate)

Example 2

Insect Bioassay

*Plutella xylostella* (Px) bioassays are performed by aliquoting 50 μl of each *E. coli* culture on the solid artificial *P. xylostella* diet (Biever and Boldt, Annals of Entomological Society of America, 1971; Shelton, et al J. Ent. Sci 26:17). 4 ml of the diet is poured into 1 oz. clear plastic cups (Bioserve product #9051). 5 neonate *P. xylostella* from a diet adapted lab colony are placed on each diet containing cup and then covered with a white paper lid (Bioserve product #9049). 10 larvae are assayed per concentration. Trays of cups are placed in an incubator for 3 days at 72° F. with a 14:10 (hours) light; dark cycle. The number of live larvae in each cup is recorded.

Example 3

Results of Bioassays

The broth of *Xenorhabdus nematophilus* strain ATCC 19061 gives 100% mortality against *Plutella xylostella* (Px) in the insect bioassay of Example 2. Broth of each of *Xenorhabdus nematophilus* strain Ps1, *Xenorhabdus poinarii* strain ATCC 49122, and *Photorhabdus luminescens* strain Ps5, likewise gives 100% mortality against *Plutella xylostella* (Px) in the insect bioassay of Example 2.

Example 4

Construction of Cosmid Libraries

Total DNA is isolated from *Xenorhabdus nematophilus* strain ATCC 19061 by treating freshly grown cells resuspended in 100 mM Tris pH 8, 10 mM EDTA with 2 mg/ml lysozyme for 30 minutes at 37° C. Proteinase K is added to a final concentration of 100 μg/ml in 0.5% SDS and incubated at 45° C. The solution clears and becomes very viscous. The SDS concentration is increased to 1% and 300 mM NaCl and equal volume of phenol-chloroform-isoamyl alcohol are added. The sample is gently mixed for 5 minutes and centrifuged at 3K. This is repeated twice. The aqueous phase is then mixed with 0.7 volumes isopropanol and centrifuged. The DNA pellet is washed three times with 70% ethanol and gently resuspended in 0.5× TE. 6 μg of DNA are treated with 0.3 unit of Sau3A per μg of DNA at 37° C. for 3.5 minutes in a volume of 100 μl. The sample is then heated for 30 minutes at 65° C. to inactivate the enzyme, then incubated with 2 units of calf intestinal alkaline phosphatase for 30 minutes at 37° C. The sample is mixed with an equal volume of phenol-chloroform-isoamyl alcohol and centrifuged. The aqueous phase is removed and mixed with 0.7 volumes isopropanol and centrifuged. The pellet is resuspended in 0.5× TE at a concentration of 100 ng/ml.

SuperCos cosmid vector (Stratagene, La Jolla, Calif.) is prepared as described by the supplier utilizing the BamHI cloning site. Prepared SuperCose at 100 ng/ml is litigated with the *X. nematophilus* DNA previously digested with Sau3A at a ratio of 2:1 in a 5 μl volume overnight at 6° C. The ligation mixture is packaged using Gigapack XL III (Stratagene) as described by the supplier. Packaged phages are infected into XL-1MR *E. coli* cells (Stratagene) as described by the supplier. The cosmid library is plated on L-agar with 50 μg/ml kanamycin and incubated 16 hours at 37° C. 500 colonies are patched to fresh L-kan plates at a density of 50/plate. The cells are washed off with L broth and mixed with 20% glycerol and frozen at −80° C.

In the case of the 4.2 Mb large genome of *X. nematophilus*, 450 clones with an average size of 40 Kb correspond to a 4-fold coverage of the genome. Therefore, screening of 450 clones should result in a 99% probability of finding any gene.

Cosmid libraries from *Xenorhabdus nematophilus* strain Ps1, *Xenorhabdus poinarii* strain ATCC 49122, and *Photorhabdus luminescens* strain Ps5 are constructed in a like manner.

Example 5

Results of the Cosmids Bioassays and Identification of Clones Having Insecticidal Activity 400 *E. coli* clones from each cosmid library are screened by insect bioassay yielding clones with activity against *Plutella xylostella*. An insecticidal cosmid clone from *Xenorhabdus nematophilus* strain ATCC 19061 is identified as pCIB9362. A 42 kb insecticidal cosmid clone from *Xenorhabdus nematophilus* strain Ps1 is identified as pCIB9379. A 42 kb insecticidal cosmid clone from *Xenorhabdus poinarii* strain ATCC 49122 is identified as pCIB9354. A 7 kb insecticidal cosmid clone from *Photorhabdus luminescens* strain Ps5 is identified as pCIB9383-21.

Example 6

Isolation of Subclones Having Insecticidal Activity

Clone pCIB9362 is digested with *SacII* and a 9 kb DNA fragment is isolated. This fragment is ligated into Bluescript out with *SacII*. The ligation mixture is transformed into DH5α*E. coli* cells as described in Molecular Cloning, second edition (Sambrook et al.). The transformation mixture is plated on L agar plus 100 μg/ml ampillicin and incubated at 37° C. overnight. Isolated colonies are grown up in L. broth with 100 μg/ml ampillicin and plasmid DNA isolated by alkaline minipreps as described in Molecular Cloning, second edition. The 9 kb *SacII* clone is identified as pCIB9362-3 and gives 100% mortality when bioassayed against *Plutella xylostella*. 3 μg of pCIB9362-3 is isolated digest with 0.3 unit of Sau3A per μg DNA for 4, 6 and 8 min, at 37° C. and heated at 75° C. for 15 min. Samples are pooled and ligated into pUC19 previously digested with BamHI and treated with calf intestinal with Xgal/Amp as described in Molecular Cloning and grown overnight at 37° C. White colonies are picked and grown up in L broth with 100 μg/ml ampicillin and plasmid DNA is isolated as previously described. DNA is digested with EcoRI/HindIII and novel restriction patterns are sequenced. Sequencing primers are ordered from Genosys Biotechnologies (Woodlands, Tex.). Sequencing is performed using the dideoxy chain-termination method and is completed using Applied Biosystems Inc. model 377 automated DNA sequencer (Foster City, Calif.). The sequence is assembled using Sequencer 3.0 from Gene Codes Corporation (Ann Arbor, Mich.).

After identification of restriction sites and of potential ORF's pCIB9362-3 is digested with ClaI and a 3.0 kb fragment is isolated cloned into Bluescript and transformed into DH5α *E. Coli* cells. The isolated colonies are grown as previously described and plasmid DNA isolated by the alkaline method. The subclone is identified as pCIB9369 and gives 100% mortality against *Plutella xylostella* in a bioassay. pCIB9369 has been deposited on Nov. 12, 1997 and identified by NRRL Number B-21883 at the USDA ARS Patent Culture Collection.

A 20 kb fragment identified as pCIB9381 as subcloned from cosmid pCIB9379 using a NotI digest.

Example 7

Bioassay Results

Insect Bioassay are conducted for pCIB9369 for a variety of insects.

| Insect | pCIB9369 |
|---|---|
| *Plutella xylostella* | +++ |
| *Heliothis virescens* | na |
| *Helioverpa zea* | na |
| *Spodoptera exgiua* | na |
| *C. elegans* | na | na = not active
+ = significant growth inhibition
++ = >40% mortality, but less than 100%
+++ = 100% mortality These results show that the insecticidal toxin resulting from expression of the 3.0 kb nucleotide sequence in pCIB9369 is highly active against *Plutella xylostella*.

Bioassays for pCIB9381, pCIB9354, and pCIB9383-21 also show high insecticidal activity against *Plutella xylostella*.

Example 8

Size Fraction of the Insecticidal Activity

*Xenorhabdus nematophilus* cosmid clone pCIB9369 and Stratagene's Blue Script vector in *E. coli* host DH5 are grown in media consisting of 50% Terrific broth and 50% Luria broth, supplemented with 50 μg/ml of ampicilin. Shake flask cultures (300 ml in 1000 ml baffled flasks) are grown at 250 RPM, overnight at 37° C. Cultures of each strain are centrifuged at 7,000 RPM in a Sorvall GS-3 rotor at 4° C. The pelleted cells are resuspended in 30 ml of 50 mM NaCl, 25 mM Tris base, pH 7.0. The concentrated cells are disrupted by sonication using a Branson Model 450 Sonicator for approximately eight 10 second cycles with cooling on ice between cycles. The sonicates are centrifuged in a Sorvall SS34 rotor at 6,000 RPM for 10 minutes at 4° C. The resultant supernatants are filtered through a 0.2 µfilter. The pellets from the centrifuged sonicates are resuspended in 30 ml of 50 mM NaCl, 25 mM Tris base, pH 7.0.

The 3 ml fractions of the filtrates are applied to Bio-Rad Econo-Pac 10DG columns that had been previously equilibrated with 10 ml of 50 mM NaCl, 25 mM Tris base, pH 7.0. The flow through collected during sample loading is discarded. The samples are fractionated with two subsequent additions of 4 ml each of the NaCl—Tris equilibration buffer. The first three fractions are saved for testing. The first fraction should contain all material above about 6,000 mol. wt. The subsequent fractions should contain material smaller than 6,000 mol. wt.

A sample of the sonicated filtrate and the resuspended pellet following sonication, are tested along with the three factors from the 10DG column for activity on *P. xylostella* neonates in surface contamination assays. The filtered supernatant of the sonicate and the first column fraction from the 9369 sample is highly active on *P. xylostella*. The second and third fractions from the 9369 sample are not active. None of the samples from the DH5a with the Blue Script plasmid culture have activity. These results suggest that the insecticidal activity encoded on *X. nematophilus* clone pCIB9369 as well as the homologues from pCIB9381, pCIB9354, and pCIB9383-21 are larger than 6,000 molecular weight.

Example 9

Stability of the Insecticidal Activity

A 300 ml of Luria broth supplemented with 100 μg/ml ampicillin is inoculated with pCIB9369 and grown over night at 37° C. The samples are placed in sterile 15 ml screw cap tubes and stored at 22° C. and 4° C. One sample is centrifuged and the supernatant removed, freeze dried and stored at 22° C. These samples are stored in these conditions for 2 weeks and then bioassayed against Px. The freeze dried material is resuspended in the same volume as prior to freeze drying the sample. All samples are resuspended by vortexing. Another sample is treated at 100° C. for 5 minutes.

| Treatment | Result |
|---|---|
| 22° C. (2 weeks) | ++ |
| 4° C. (2 weeks) | ++ |
| Freeze Dried (2 weeks) | ++ |
| 100° C. for 5 minutes | na | na = not active.

Example 10

Heat Inactivation of the Insecticidal Activity

The heat stability of the toxin is determined. Overnight cultures of the *E. coli* strain pCIB9369 (*E. coli* host DH5a, carrying the 3.0 kb DNA of *Xenorhabdus nematophilus*) are grown in a 50:50 mixture of Luria broth and terrific broth. Cultures are grown at 37° C. in culture tubes on a tube roller. Samples of one ml each of the culture are placed in a 1.5 ml eppendorf tube and placed at 60° C., 80° C. The samples are removed after five minutes and allowed to cool to room temperature. This sample along with an untreated portion of the culture is assayed on *P. xylostella*. 50 μl of sample of sample is spread on diet, allowed to dry and neonate larvae *P. xylostella* applied to the surface. The assay is incubated for 5 days at room temperature.

The untreated sample and the sample treated at 60° C. cause 100% mortality. The sample treated at 80° C. and a diet alone control do not cause observable mortality.

Example 11

Protease Treatment of the Insecticidal Activity

*Xenorhabdus nematophilus* cosmid clone pCIB9369 and Stratagene's Blue Script vector in *E. coli* DH5 are grown in media consisting of 50% Terrific broth and 50% Luria broth, supplemented with 50 μg/ml of ampicilin. Shake flask cultures (300 ml in 1000 ml baffled flasks) are grown at 250 RPM, overnight at 37° C. Cultures of each strain are centrifuged at 7,000 RPM in a Sorvall GS-3 rotor at 4° C. The pelleted cells are resuspended in 30 ml of 50 mM NaCl, 25 mM Tris base, pH 7.0. The concentrated cells are disrupted by sonication using a Branson Model 450 Sonicator for approximately eight 10 second cycles with cooling on ice between cycles. The sonicates are centrifuged in a Sorvall SS34 rotor at 6,000 RPM for 10 minutes at 4° C. The resultant supernatants are filtered through a 0.2 μ filter. One ml samples of the supernatants are adjusted to 5 mM Ca++ with the addition of $CaCl_2$. Protease K (Gibco BRL; Gaithersburg, Md.) is added to 500 μg/ml. Samples are incubated for 2 and 24 hr at 37° C. Control samples are prepared and incubated with added Ca++ but no protease.

The sonicate filtrate from pCIB9369 and the pCIB9369 samples incubated in the presence of 5 mM Ca++ produce 100% mortality on *Plutella xylostella* neonate larvae. The pCIB9369 samples incubated with protease K in addition to Ca++ show slightly less mortality, approximately 90% mortality on Plutella.

Example 12

Sequence Comparisons with the Protein Sequence of cry3A and the Protein Sequence of a Juvenile Hormone Esterase The nucleotide sequence of pCIB9369 (SEQ ID NO:1) reveals two open reading frames (ORFs) at nucleotides 569–976 and 1045–2334. ORF #1 has no homology to any sequence in Genbank after a search with the UWGCG Blast and Gap programs. A Gap analysis of the protein encoded by ORF #2 of pCIB9369 by the Blast program identifies some insignificant homology (21% identity) to *Bacillus thuringensis* cry3A protein. However, a Gap analysis of the protein encoded by ORF #2 of pCIB9369 (SEQ ID NO:3) by the Blast program does identify homology (30.6% AA identity and 44.1% AA similarity) to a juvenile hormone esterase-related protein (GenBank accession 2921553; Henikoff et al., *PNAS USA* 89: 10915–10919 (1992)).

The nucleotide sequences of pCIB9381, pCIB9354, and pCIB9383-21 also reveal two open reading frames in each of these clones. The nucleotide sequences of the two ORFs in each of pCIB9381 and pCIB9383-21 are all over 90% identical to those in pCIB9369. Hence, the ORF #2 proteins of pCIB9381 and pCIB9383-21 have essentially the same homology to the juvenile hormone esterase-related protein as does the ORF #2 protein of pCIB9369. The nucleotide sequence of ORF #1 of pCIB9354 is 77% identical to the nucleotide sequence of ORF #1 of pCIB9369, and the nucleotide sequence of ORF #2 of pCIB9354 is 79% identical to the nucleotide sequence of ORF #2 of pCIB9369. The ORF #2 protein of pCIB9354 also has homology to the juvenile hormone esterase-related protein (29.5% AA identity and 42.2% AA similarity).

Example 13

Sequence Comparison of pCIB9369 and Sequences from WO 98/08388

Twenty-two sequences of 60 nucleotides each (60-mers) are derived from the 38.2 kb DNA fragment whose nucleotide sequence is described in WO 98/08388 and are compared to the nucleotide sequence of pCIB9362-3, which comprises pCIB9369. The first 60-mer starts at base 1 in the 38.2 kb DNA fragment, while the other 60-mers are located at approximately 2 kb intervals on the DNA fragment. Their positions on the 38.2 kb DNA fragment are listed below:

1–60; 2,041–2,100; 4,021–4,080; 6,001–6,060; 8,041–8,100; 10,021–10,080; 12,001–12,060; 14,041–14,100; 16,021–16,080; 18,001–18,060; 20,041–20,100; 22,021–22,080; 24,001–24,060; 26,041–26,100; 28,021–28,080; 30,001–30,060; 32,041–32,100; 34,021–34,080; 36,001–36,060; 38,041–38,100; 38,161–38,220.

The sequences are compared using UWGCG Gap program and each of the 22 60-mer sequences as well their complementary sequences are tested. The results of these alignments indicate that the highest percentage of identity is 53%, which is not considered to be a significant homology in the art.

Example 14

Southern Blot Analysis using Probes Derived from WO 98/08388 Sequences

Pairs of oligonucleotides are designed to amplify DNA fragments of the 38.2 kb DNA fragment published in WO 98/08388. The oligonucleotides are ordered from Genosys Biotechnologies (The Woodlands, Tex.) and their positions in the 38.2 kb DNA fragment are indicated below. Also listed are their and the sizes of the amplified PCR fragments:

VK1046: positions 20–40

VK1047: positions 2,078–2,100

Size of the PCR fragment amplified using VK1046 and VK1047: 2,080 bp

VK1048: positions 11,221–11,241

VK1049: positions 13,360–13,380

Size of the PCR fragment amplified using VK1048 and VK1049: 2,120 bp

VK1050: positions 26,581–26,601

VK1051: positions 28,537–28,560

Size of the PCR fragment amplified using VK1050 and VK1051: 1,979 bp

VK1052: positions 18,901–18,921

VK1053: positions 20,321–20,340

Size of the PCR fragment amplified using VK1052 and VK1053: 1,439 bp

VK1054: positions 34,261–34,281

VK1055: positions 35,320–35,340 BP

Size of the PCR fragment amplified using VK1054 and VK1055: 1,079 bp

The PCR reactions are completed using a Perkin-Elmer 9600 Thermo-Cycle with the following conditions: 94° C. 2 min.; then 30 cycles at 94° C., 30 sec; 54° C., 30 sec; 72° C., 4 min. The samples contain 800 ng of *Xenorhabdus nematophilus* DNA, 0.1–0.5 µM of each pair of oligonucleotides, 250 µM dNTP, 5U Taq Polymerase and 1X buffer (Perkin-Elmer) in a final volume of 100 µl. The completed reactions are precipitated in ethanol, resuspended in TE and loaded on a 1% SeaPlaque (FMC, Rockland, Me.) TBE gel. After electrophoresis, the fragments are cut out from the gel after ethidium bromide staining and visualization under UV light. The gel slices are melted at 65° C. and 10 µl aliquots are mixed with 10 µl distilled water, boiled for 5 min. and placed on ice. Then, 15 µl of Random Priming label buffer (GIBCO-BRL, Gaithersburg, Md.), 6 µl dNTP mix (without dCTP), 80 µCi α-dCT$^{32}$P and 1 µl Klenow are mixed. The labeling reaction is carried out during 60 min. at room temperature. The samples are cleaned up on Nick columns (Pharmacia Biotech) according to the supplier's recommendations. The probes are boiled for 5 min. and placed on ice.

A Southern blot is performed by digesting *Xenorhabdus nematophilus* total DNA, DNA derived from cosmids pCIB9362 and pCIB9363 (these cosmids overlap over 25 kb and both contain the DNA fragment of pCIB9369; pCIB9362 was used to subcloning), DNA derived from subclones pCIB9362-3 (9 kb SacII fragment) and pCIB9369 (2.96 kb ClaI fragment), digested with ClaI, SacII or HindIII. The digestion reactions are loaded on a 0.75% agarose TBE gel and run overnight. A picture is taken and the gel is treated as described by Bio-Rad for blotting to a Zeta-Probe hydrization membrane. After blotting, the membrane is baked at 80° C. for 30 min. The membrane is then placed in 7% SS, 250 mM sodium phosphate, pH 7.2 and incubated at 67° C. for 30 min. Fresh solution is added and after equilibration to 67° C., the radioactive probes described above are added and allowed to hybridize overnight. The membrane is washed in 2X SSC, 0.5% SS for 30 min. at 67° C. and then 0.5X SSC, 0.5% SDS for 30 min. at 67° C. The membrane is exposed on to a film for 1 hr and 3 hr. The film is developed and the results show that the PCR probes from the WO 98/08388 sequence do not hybridize to the DNA of the cosmids or the DNA of the subclones described in this invention. However, a strong hybridization signal is observed with *X. nematophilus* DNA.

These results corroborate the results of the sequence comparisons and show that clone pCIB9369 is different from the nucleotide sequence described in WO 98/8388.

B. Expression of the Nucleic Acid Sequences of the Invention in Heterologous Microbial Hosts Microorganisms which are suitable for the heterologous expression of the nucleotide sequences of the invention are all microorganisms which are capable of colonizing plants or the rhizosphere. As such they will be brought into contact with insect pests. These include gram-negative microorganisms such as *Pseudomonas*, *Enterobacter* and *Serratia*, the gram-positive microorganism *Bacillus* and the fungi *Trichoderma*, *Gliocladium*, and *Saccharomyces cerevisiae*. Particularly preferred heterologous hosts are *Pseudomonas fluorescens*, *Pseudomonas putida*, *Pseudomonas cepacia*, *Pseudomonas aureofaciens*, *Pseudomonas aurantiaca*, *Enterobacter cloacae*, *Serratia marscesens*, *Bacillus*

*subtilis, Bacillus cereus, Trichoderma viride, Trichoderma harzianum, Glioocladium virens,* and *Saccharomyces cerevisiae.*

Example 19

Expression of the Nucleotide Sequences in *E. coli* and Other Gram-Negative Bacteria Many genes have been expressed in gram-negative bacteria in a heterologous manner. Expression vector pKK223-3 (Pharmacia catalogue #27-4935-01) allows expression in *E. coli*. This vector has a strong tac promoter (Brosius, J. et al., *Proc. Natl. Acad. Sci. USA* 81) regulated by the lac repressor and induced by IPTG. A number of other expression systems have been developed for use in *E. coli*. The thermoinducible expression vector pP$_L$ (Pharmacia #27-4946-01) uses a tightly regulated bacteriophage λ promoter which allows for high level expression of proteins. The lac promoter provides another means of expression but the promoter is not expressed at such high levels as the tac promoter. With the addition of broad host range replicons to some of these expression system vectors, expression of the nucleotide sequence in closely related gram negative-bacteria such as *Pseudomonas, Enterobacter, Serratia* and *Erwinia* is possible. For example, pLRKD211 (Kaiser & Kroos, Proc. Natl. Acad. Sci. USA 81: 5816–5820 (1984)) contains the broad host range replicon ori T which allows replication in many gram-negative bacteria.

In *E. coli*, induction by IPTG is required for expression of the tac (i.e. trp-lac) promoter. When this same promoter (e.g. on wide-host range plasmid pLRKD211) is introduced into *Pseudomonas* it is constitutively active without induction by IPTG. This trp-lac promoter can be placed in front of any gene or operon of interest for expression in *Pseudomonas* or any other closely related bacterium for the purposes of the constitutive expression of such a gene. Thus, a nucleotide sequence whose expression results in an insecticidal toxin can therefore be placed behind a strong constitutive promoter, transferred to a bacterium which has plant or rhizosphere colonizing properties turning this organism to an insecticidal agent. Other possible promoters can be used for the constitutive expression of the nucleotide sequence in gram-negative bacteria. These include, for example, the promoter from the *Pseudomonas* regulatory genes gafA and lemA (WO 94/01561) and the *Pseudomonas savastanoi* IAA operon promoter (Gaffney et al., *J. Bacteriol.* 172: 5593–5601 (1990).

Example 20

Expression of the Nucleotide Sequences in Gram-Positive Bacteria

Heterologous expression of the nucleotides sequence in gram-positive bacteria is another means of producing the insecticidal toxins. Expression systems for *Bacillus* and *Streptomyces* are the best characterized. The promoter for the erythromycin resistance gene (ermR) from *Streptococcus pneumoniae* has been shown to be active in gram-positive aerobes and anaerobes and also in *E. coli* (Trieu-Cuot et al., *Nucl Acids Res* 18: 3660 (1990)). A further antibiotic resistance promoter from the thiostreptone gene has been used in *Streptomyces* clong vectors (Bibb, *Mol Gen Genet* 199: 26–36 (1985)). The shuttle vector pHT3101 is also appropriate for expression in *Bacillus* (Lereclus, *FEMS Microbiol Lett* 60: 211–218 (1989)). A significant advantage of this approach is that many gram-positive bacteria produce spores which can be used in formulations that produce insecticidal agents with a longer shelf life. *Bacillus* and *Streptomyces* species are aggressive colonizers of soils

Example 21

Expression of the Nucleotide Sequences in Fungi

*Trichoderma harzianum* and *Gliocladium virens* have been shown to provide varying levels of biocontrol in the field (U.S. Pat. No. 5,165,928 and U.S. Pat. No. 4,996,157, both to Cornell Research Foundation). A nucleotide sequence whose expression results in an insecticidal toxin could be expressed in such a fungus. This could be accomplished by a number of ways which are well known in the art. One is protoplast-mediated transformation of the fungus by PEG or electroporation-mediated techniques. Alternatively, particle bombardment can be used to transform protoplasts or other fungal cells with the ability to develop into regenerated mature structures. The vector pAN7-1, originally developed for *Aspergillus* transformation and now used widely for fungal transformation (Curragh et al., *Mycol. Res.* 97(3):313–317 (1992); Tooley et al., *Curr. Genet.* 21: 55–60 (1992); Punt et al., *Gene* 56: 117–124 (1987)) is engineered to contain the nucleotide sequence. This plasmid contains the *E. coli* the hygromycin B resistance gene flanked by the *Aspergillus nidulans* gpd promoter and the trpC terminator (Punt et al., *Gene* 56: 117–124 (1987)).

In a preferred embodiment, the nucleic acid sequences of the invention are expressed in the yeast *Saccharomyces cerevisiae*. For example, each of the two ORF's from pCIB9369, pCIB9381, pCIB9354, or pCIB9383 are cloned into individual vectors with the GAL1 inducible promoter and the CYC1 terminator. Each vector has ampicillin resistance and the 2 micron replicon. The vectors preferably differ in their yeast growth markers. The constructs are transformed into *S. cerevisiae* independently and together. The ORFs are expressed together and tested for protein expression and insecticidal activity.

C. Formulation of the Insecticidal Toxin

Insecticidal formulations are made using using active ingredients which comprise either the isolated toxin or alternatively suspensions or concentrates of cells which produce it and which are described in the examples above. For example, *E. coli* cells expressing the insecticidal toxin may be used for the control of the insect pests. Formulations are made in liquid or solid form and are described below.

Example 18

Liquid Formulation of Insecticidal Compositions

In the following examples, percentages of composition are given by weight:

| I. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethylene glycol ether (36 moles of ethylene oxide) | 5% | — | — |
| Tributylphenol polyethylene glyco ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160–190°) | — | — | 94% | — |

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgit | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 19

Solid Formulation of Insecticidal Compositions

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 moles of ethylene oxide) | — | 2% | — |
| Highly dispersed silicic acid | 5% | 27% | 10% |
| Kaolin | 67% | — | — |

The acive ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether | 3% |

-continued

| 2. Emulsifiable concentrate: | |
|---|---|
| (4–5 moles of ethylene oxide) | |
| Calcium dodecylbenzenesulfonate | 3% |
| Castor oil polyglycol ether | 4% |
| (36 moles of ethylene oxide) | |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

The insecticidal formulations described above are applied to the plants according to methods well known in the art, in such amounts that the insect pests are controlled by the insecticidal toxin.

D. Expression of the Nucleotide Sequences in Transgenic Plants

The nucleic acid sequences described in this application can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector system λgtII, λgt10 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAII, and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the nucleotide sequence of the invention confer insect resistance to the transgenic plants.

Example 22

Modification of Coding Sequences and Adjacent Sequences

The nucleotide sequences described in this application can be modified for expression in transgenic plant hosts. A host plant expressing the nucleotide sequences and which produces the insecticidal toxins in its cells has enhanced resistance to insect attack and is thus better equipped to withstand crop losses associated with such attack.

The transgenic expression in plants of genes derived from microbial sources may require the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (*Science* 261: 754–756 (1993)) have expressed the *Pseudomonas* nahG gene in transgenic plants under the control of the CaMV 35S promoter and the CaMV tml terminator successfully without modification of the coding sequence and with x bp of the *Pseudomonas* gene upstream of the ATG still attached, and y bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as *Bacillus*. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plants genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (NAR 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | |
|---|---|---|---|---|---|---|---|---|---|
| | −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants at 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

Example 23

Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. *Plant Science* 79: 87–94 (1991); maize—Christensen et al. *Plant Molec. Bio.*, 12: 619–632 (1989); and *Arabidopsis*—Norris et al., *Plant Mol. Biol.* 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (*Plant Cell Rep.* 12: 491–495 (1993)) describe a vector (pAHC25) that comprises the maize ubiquitin promoter and first intron and its high activity in cell suspensions of numerous monocotyledons when introduced via microprojectile bombardment. The *Arabidopsis ubiquitin* promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761eNX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and GalI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translation initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. *Plant Cell* 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. *Mol. Gen. Genet.* 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of the sequences around the initiating ATG (of the GUS reporter gene) also enhanced expression. The promoter expression cassettes described by McElroy et al. (*Mol. Gene. Genet.* 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. *Plant Cell Rep.* 12: 506–509 (1993)).

d. Inducible Expression, the PR-1 Promoter:

The double 35S promoter in pCGN1761ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., 1992). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicyclic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

F. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1968) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6xGAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is described by de Framond (*FEBS* 290: 103–106 (1991)) and also in the published patent application EP 0 452 269, which is herein incorporated by reference. This promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. *Plant Molec. Biol.* 22: 573–588 (1993), Logemann et al. *Plant Cell* 1: 151–158 (1989), Rohrmeier & Lehle, *Plant Molec. Biol.* 22: 783–792 (1993), Firek et al. *Plant Molec. Bio.* 22: 129–142 (1993), Warner et al. *Plant J.* 3: 191–201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques.

Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to −1725 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (*Plant Molec Biol* 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g., Gallie et al. *Nucl. Acids Res.* 15: 8693–8711 (1987); Skuzeski et al. *Plant Molec. Biol.* 15: 65–79 (1990)).

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronze1 gene had a similar effect in enhancing expression. Intron sequences have been 4. Targeting of the Gene Product Within the Cell Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. *J. Biol. Chem.* 263: 15104–15109 (1988)). These signal sequences can be fused to heterologous gene products to effect the import of heterologous products into the chloroplast (van den Broeck, et al. *Nature* 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. *Plant Molec. Biol.* 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (*Proc. Natl. Acad. Sci. USA* 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, *Plant Cell* 2: 769–783 (1990)). Additionally, amino terminal sequences in conjunction with carboxy terminal sequences are responsible for vacuolar targeting of gene products (Shinshi et al. *Plant Molec. Biol.* 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) *Methods in Chloroplast Molecular Biology*, Elsevier pp 1081–1091 (1982) and Wasmann et al. *Mol. Gen. Genet.* 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Example 24

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra, *Gene* 19: 259–268 (1982); Bevan et al., *Nature* 304:184–187 (1983)), the bar gene, which confers resistance to the herbicide phosphinothricin (White et al., *Nucl. Acids Res* 18: 1062 (1990), Spencer et al. *Theor. Appl. Genet* 79: 625–631 (1990)), the hph gene, which confers resistance to the antibiotic hygromycin (Blochinger & Diggelmann, *Mol Cell Biol* 4: 2929–2931), and the dhfr gene, which confers resistance to methatrexate (Bourouis et al., *EMBO J.* 2(7): 1099–1104 (1983)), and the EPSPS gene, which confers resistance to glyphosate (U.S. Pat. Nos. 4,940,935 and 5,188,642).

1. Vectors Suitable for *Agrobacterium* Transformation

Many vectors are available for transformation using *Agrobacterium tumefaciens*. These typically carry at least one T-DNA border sequence and include vectors such as pBIN19 (Beven, *Nucl. Acids Res.* (1984)) and pXYZ. Below, the construction of two typical vectors suitable for *Agrobacterium* transformation is described.

a. pCIB200 and pCIB2001:

The binary vectors pcIB200 and pCIB2001 are used for the construction of recombinant vectors for use with *Agrobacterium* and are constructed in the following manner. pTJS75kan is created by NarI digestion of pTJS75 (Schmidhauser & Helinski, *J. Bacteriol.* 164: 446–455 (1985)) allowing excision of the tetracycline-resistance gene, followed by insertion of an AccI fragment from pUC4K carrying an NPTII (messing & Vierra, *Gene* 19: 259–268 (1982); Bevan et al., *Nature* 304: 184–187 (1983); McBride et al., *Plant Molecular Biology* 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., *Gene* 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (*Gene* 53: 153–161 (1987)). Various derivatives of pCIB10 are constructed which incorporate the gene for hygromycin B phosphotransferase described by Gritz et al. (*Gene* 25: 179–188 (1983)). These derivatives enable selection of transgenic plant cells on hygromycin only (pCIB743), or hygromycin and kanamycin (pCIB715, pCIB717).

2. Vectors Suitable for non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. *EMBO J* 6: 2519–2523 (1987)). This generated pCIB3064, which comprises the bar gene under the control the CaMV 35S promoter and terminator for herbicide selection, a gene for ampicillin resistance (for selection in *E. coli*) and a polylinker with the unique sites SphI, PstI, HindIII, and BamHI. This vector is suitable for the clong of plant expression cassettes containing their own regulatory signals.

b. pSOG19 and pSOG35:

pSOB35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Example 25

Transformation

Once a nucleic acid sequence of the invention has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3: 2717–2722 (1984), Potrykus et al., *Mol. Gen. Genet.* 199: 169–177 (1985), Reich et al., *Biotechnology* 4: 1001–1004 (1986), and Klein et al., *Nature* 327: 70–73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. *Plant Cell* 5: 159–169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, *Nucl. Acids Res.* 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants for transformed protoplasts. Gordon-Kamm et al. (*Plant Cell* 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (*Biotechnology* 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for *Japonica*-type and *Indica*-type (Zhang et al. *Plant Cell Rep* 7: 379–384 (1988); Shimamoto et al. *Nature* 338: 274–277 (1989); Datta et al. *Biotechnology* 8: 736–740 (1990)). Both types are also routinely transformable using particle bombardment (Christou et al. *Biotechnology* 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (*Biotechnology* 10: 667–674 (1992)) using particle bombardment into cells of type C long-term regenerable callus, and also by Vasil et al. (*Biotechnology* 11: 1553–1558 (1993)) and Weeks et al. (*Plant Physiol.* 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, *Physiologia Plantarum* 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, which are incorporated herein by reference.

3. Transformation of Plastids

Seeds of *Nicotiana tabacum* c.v. 'Xanthi nc' are germinated seven per plate in a 1" circular array on T agar medium and bombarded 12–14 days after sowing with 1 μm tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings are incubated on T medium for two days after which leaves are excised and placed abaxial side up in bright light (350–500 μmol photons/m$^2$/s) on plates of RMOP medium (Svab, Z., Hajdukiewicz, P. and Maliga, P. (1990) *PNAS* 87, 8526–8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

E. Breeding and Seed Production

Example 26

Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, N.Y. (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, N.Y. (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant disease, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pestidice treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

Example 27

Seed Production

In seed production, germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compound are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods, such as the methods exemplified above, which are characterized by the use of transgenic plants, transgenic plant material, or transgenic seed according to the present invention.

The seeds may be provided in a bag, container or vessel comprised of a suitable packaging material, the bag or container capable of being closed to contain seeds. The bag, container or vessel may be deigned for either short term or long term storage, or both, of the seed. Examples of a suitable packaging material include paper, such as kraft paper, rigid or pliable plastic or other polymeric material, glass or metal. Desirably the bag, container, or vessel is comprised of a plurality of layers of packaging materials, of the same or differing type. In one embodiment the bag, container or vessel is provided so as to exclude or limit water and moisture from contacting the seed. In one example, the bag, container or vessel is sealed, for example heat sealed, to prevent water or moisture from entering. In another embodiment water absorbent materials are placed between or adjacent to packaging material layers. In yet another embodiment the bag, container or vessel, or packaging material of which it is comprised is treated to limit, suppress or prevent disease, contamination or other adverse affects of storage or transport of the seed. An example of such treatment is sterilization, for example by chemical means or by exposure to radiation. Comprised by the present invention is a commercial bag comprising seed of a transgenic plant comprising a gene of the present invention that is expressed in said transformed plant at higher levels than in a wild type plant, together with a suitable carrier, together with label instructions for the use thereof for conferring broad spectrum disease resistance to plants.

The above disclosed embodiments are illustrative. This disclosure of the invention will place one skilled in the art in possession of many variations of the invention. All such obvious and foreseeable variations are intended to be encompassed by the appended claims.

SEQUENCE LISTING

<160> NUMBER OF SEQ ID NOS: 15

<210> SEQ ID NO 1
<211> LENGTH: 2978
<212> TYPE: DNA
<213> ORGANISM: Xenorhabdus nematophilus
<220> FEATURE:
<221> NAME/KEY: CDS
<222> LOCATION: (569)..(976)

```
<223> OTHER INFORMATION: orf1
<221> NAME/KEY: CDS
<222> LOCATION: (1045)..(2331)
<223> OTHER INFORMATION: JHE-like orf2
<223> OTHER INFORMATION: pCIB9369

<400> SEQUENCE: 1
atcgatgtga cggcagagta tttttattcc tgtaaactga cgacaatgca tttctaagat      60
atcaatataa taatgataaa tttattgatc atatatctgt tatattttga ttgaaaatta     120
ttgaatatac ctcttgtact aaattcatta catttttttt actttaaaca acattaaatt     180
cacacataat acagcttaaa tataacatgt gatatatatt atgattataa aaaacattaa     240
aataaataat acgccacata tattaacaat atctaattac tgatgatact attttctgag     300
tatatataaa tcttaaagaa aataattatt ttttatattt cacatcaatt taaaatctgc     360
ttagaatgcc cccggcatc acaagaaaac aaaatcattc aagtaataca atagagttaa      420 attaaaaat aacatgtata acaaaataca tagacaacta tacatgtaaa tgacagacaa      480
ctgacaaaac atagcaaaaa aacgccttaa atattaaggt atcaaaacaa tatatcagac     540
tatcttaaat ctaataggag aatccctc atg att aca ata cat atc agt ggt        592
                               Met Ile Thr Ile His Ile Ser Gly
                                1               5 ggt agt gta aca att aat aac aat ata gta aca gaa act gat gtc caa       640
Gly Ser Val Thr Ile Asn Asn Asn Ile Val Thr Glu Thr Asp Val Gln
    10              15                  20 aat aca ccc gct tca gcg cct tta tca att act aat ttt agg gat atg       688
Asn Thr Pro Ala Ser Ala Pro Leu Ser Ile Thr Asn Phe Arg Asp Met
25                  30                  35                  40 aca ata gaa cct cat tca tct gtt gag gcg ata aga acc gat aca ccg       736
Thr Ile Glu Pro His Ser Ser Val Glu Ala Ile Arg Thr Asp Thr Pro
                45                  50                  55 att att cct gaa tca cga cca aat tac tat gtt gct aat tct ggc ccg       784
Ile Ile Pro Glu Ser Arg Pro Asn Tyr Tyr Val Ala Asn Ser Gly Pro
    60                  65                  70 gcc tca tca gtc aga gct gtt ttc tat tgg tcc cac tct ttt aca tca       832
Ala Ser Ser Val Arg Ala Val Phe Tyr Trp Ser His Ser Phe Thr Ser
75                  80                  85 gaa tgg ttt gaa tct tcc tct att att gta aaa gca ggc gaa gac gga       880
Glu Trp Phe Glu Ser Ser Ser Ile Ile Val Lys Ala Gly Glu Asp Gly
    90                  95                  100 gtc tta cat tca ccg ggt aat tct tta tat tac agc aag gtt gta att       928
Val Leu His Ser Pro Gly Asn Ser Leu Tyr Tyr Ser Lys Val Val Ile
105                 110                 115                 120 tat aac gat aca gac aaa cgt gct ttt gtt acc ggc tac aat cta taa       976
Tyr Asn Asp Thr Asp Lys Arg Ala Phe Val Thr Gly Tyr Asn Leu
                125                 130                 135 taacgcagaa atacaatcca tatttccaat gaatttcaaa taacatcctt aaggcaagaa    1036 acaaaatc atg aat aat gaa ccg atg aat act aat gaa tca caa gct tca     1086
          Met Asn Asn Glu Pro Met Asn Thr Asn Glu Ser Gln Ala Ser
                    140                 145 gag ata gta ccc tca atg aat gaa tct ata tta gca gca cct tat tca     1134
Glu Ile Val Pro Ser Met Asn Glu Ser Ile Leu Ala Ala Pro Tyr Ser
150                 155                 160                 165 att tct aca cct aat tat gaa tgg gat atg tca tca ata ata aaa gat     1182
Ile Ser Thr Pro Asn Tyr Glu Trp Asp Met Ser Ser Ile Ile Lys Asp
            170                 175                 180 gct att att ggt ggt ata ggc ttt att cct ggt ccg ggc tca gca ata     1230
Ala Ile Ile Gly Gly Ile Gly Phe Ile Pro Gly Pro Gly Ser Ala Ile
    185                 190                 195
```

-continued

| | |
|---|---|
| tca ttt ttg tta ggg tta ttt tgg cca caa caa acc gac aat act tgg<br>Ser Phe Leu Leu Gly Leu Phe Trp Pro Gln Gln Thr Asp Asn Thr Trp<br>200                           205                       210 | 1278 |
| gag caa att ctc caa aaa gta gaa caa atg atc gag caa gcc aat ctc<br>Glu Gln Ile Leu Gln Lys Val Glu Gln Met Ile Glu Gln Ala Asn Leu<br>215                    220                       225                 230 | 1326 |
| aaa act att caa gga ata ttg aac ggc gat ata caa gaa att aaa ggc<br>Lys Thr Ile Gln Gly Ile Leu Asn Gly Asp Ile Gln Glu Ile Lys Gly<br>                235                     240                     245 | 1374 |
| aaa atg gaa cat gtg caa ttc atg cta gaa tcc tca cct ggc act caa<br>Lys Met Glu His Val Gln Phe Met Leu Glu Ser Ser Pro Gly Thr Gln<br>250                           255                       260 | 1422 |
| gaa agc cat gac gca tac atg ttt ctg gcg aga tat ctg gtc agt ata<br>Glu Ser His Asp Ala Tyr Met Phe Leu Ala Arg Tyr Leu Val Ser Ile<br>         265                     270                     275 | 1470 |
| gac gaa aaa ttc aag tct ttt gat aac aaa aca aat tat caa att ctt<br>Asp Glu Lys Phe Lys Ser Phe Asp Asn Lys Thr Asn Tyr Gln Ile Leu<br>280                           285                     290 | 1518 |
| ccc atg tat acc aat acg att atg tta caa gcc cct tat tgg aaa atg<br>Pro Met Tyr Thr Asn Thr Ile Met Leu Gln Ala Pro Tyr Trp Lys Met<br>295                      300                     305                 310 | 1566 |
| ggt ata gag aga aaa gat gag atc aaa cta aca gat ata gaa gtt aat<br>Gly Ile Glu Arg Lys Asp Glu Ile Lys Leu Thr Asp Ile Glu Val Asn<br>                315                     320                     325 | 1614 |
| gaa tta aaa gag ctg ata gga aaa tta tct acc agc gcc gat aaa tat<br>Glu Leu Lys Glu Leu Ile Gly Lys Leu Ser Thr Ser Ala Asp Lys Tyr<br>330                           335                     340 | 1662 |
| att cat gat gtc tat act cgt gaa tat gat aat gcg atg aac act tca<br>Ile His Asp Val Tyr Thr Arg Glu Tyr Asp Asn Ala Met Asn Thr Ser<br>         345                     350                     355 | 1710 |
| aca gca gca aat atc acc aat aat tta tta tct gca aga ggc tat tgt<br>Thr Ala Ala Asn Ile Thr Asn Asn Leu Leu Ser Ala Arg Gly Tyr Cys<br>360                           365                     370 | 1758 |
| tta tta cat ggt tta gaa tgt ctc gaa gtc att aac cat ata caa aat<br>Leu Leu His Gly Leu Glu Cys Leu Glu Val Ile Asn His Ile Gln Asn<br>375                      380                     385                 390 | 1806 |
| aat agc ctt gag caa agt ttt tat cct aaa act atc agc tac tcc acc<br>Asn Ser Leu Glu Gln Ser Phe Tyr Pro Lys Thr Ile Ser Tyr Ser Thr<br>                395                     400                     405 | 1854 |
| gta ttc gat cgc cag aca aat aaa aca agg gtt caa gcc ctg aca gaa<br>Val Phe Asp Arg Gln Thr Asn Lys Thr Arg Val Gln Ala Leu Thr Glu<br>410                           415                     420 | 1902 |
| gac gat caa atg caa gag cca ttc aag cct gct tta att aat ggg aag<br>Asp Asp Gln Met Gln Glu Pro Phe Lys Pro Ala Leu Ile Asn Gly Lys<br>         425                     430                     435 | 1950 |
| tac aac aaa ata aaa tca ttg att ggg tat gta caa aga atc gga aac<br>Tyr Asn Lys Ile Lys Ser Leu Ile Gly Tyr Val Gln Arg Ile Gly Asn<br>440                           445                     450 | 1998 |
| gca ccc aga gtt gga ggc att aaa gtc aca ttt gca aac gat gca tct<br>Ala Pro Arg Val Gly Gly Ile Lys Val Thr Phe Ala Asn Asp Ala Ser<br>455                      460                     465                 470 | 2046 |
| tat acc ctc ggt aca gta act tca gaa gta aac tca att gaa ctg aat<br>Tyr Thr Leu Gly Thr Val Thr Ser Glu Val Asn Ser Ile Glu Leu Asn<br>                475                     480                     485 | 2094 |
| gac agc gtt ata acc agc ctg gaa gta tgg gga aat ggc gct att gat<br>Asp Ser Val Ile Thr Ser Leu Glu Val Trp Gly Asn Gly Ala Ile Asp<br>490                           495                     500 | 2142 |

```
gag gca ttc ttt aca tta agt gac gga cgt caa ttt agg ctt ggc caa        2190
Glu Ala Phe Phe Thr Leu Ser Asp Gly Arg Gln Phe Arg Leu Gly Gln
            505                 510                 515 cgc tat gcc agt aac tat aga aaa tat gct gtc gat aac cac tat att        2338
Arg Tyr Ala Ser Asn Tyr Arg Lys Tyr Ala Val Asp Asn His Tyr Ile
        520                 525                 530 tca gga ttg tac tta gcc agt gat gaa cct tca ttg gca ggt caa gca        2286
Ser Gly Leu Tyr Leu Ala Ser Asp Glu Pro Ser Leu Ala Gly Gln Ala
535                 540                 545                 550 gca ggc att gca gtt tca tac cat atg ata gct gat aaa aaa tca            2331
Ala Gly Ile Ala Val Ser Tyr His Met Ile Ala Asp Lys Lys Ser
                555                 560                 565 tagtattaac aggcttctga tttcagacta agcaagtaag cggatcttca gagtcatata      2391
gcatgcrata tgactgaaga gttatccgct cctcactttt aactaaactc attacatcct      2451
ccactaattt attcagcgat aaaaaacaca caatgaaaac caaacatttg tttgttattt      2511
tcataaaaaa tgcaactctt tgtttaataa aaatttatcg cagtataaaa tattgccagt      2571
tttatagact atattatatt ctcactttat ctatattttt agtttaaaat tcaagactaa      2631
aatcacactt ttatgcaaaa tgttcacttt ataaactta cgatcgtact ctcataatta      2691
gaatcaaata tcaaaataat ctttackgtt tatcagacct gcaatacaac attaatacaa      2751
aaaatagcta aggacatgat atgttgaaaa gggaaatca gatattgcaa ctactgaagg      2811
gcgatccttt catgcagcag caagaaatcg ctgatatcct tggaattagc cgctcgtgtg      2871
ttgcaggaca tattatgaac ctaagcaaaa aaggatatat taaaggcaaa gggtatatct      2931
tatctaatga tgcttatact gttacaattg gtgctgccaa tatcgat                   2978

<210> SEQ ID NO 2
<211> LENGTH: 135
<212> TYPE: PRT
<213> ORGANISM: Xenorhabdus nematophilus

<400> SEQUENCE: 2

Met Ile Thr Ile His Ile Ser Gly Gly Ser Val Thr Ile Asn Asn Asn
1               5                   10                  15

Ile Val Thr Glu Thr Asp Val Gln Asn Thr Pro Ala Ser Ala Pro Leu
            20                  25                  30

Ser Ile Thr Asn Phe Arg Asp Met Thr Ile Glu Pro His Ser Ser Val
        35                  40                  45

Glu Ala Ile Arg Thr Asp Thr Pro Ile Ile Pro Glu Ser Arg Pro Asn
    50                  55                  60

Tyr Tyr Val Ala Asn Ser Gly Pro Ala Ser Ser Val Arg Ala Val Phe
65                  70                  75                  80

Tyr Trp Ser His Ser Phe Thr Ser Glu Trp Phe Ser Ser Ser Ile
                85                  90                  95

Ile Val Lys Ala Gly Glu Asp Gly Val Leu His Ser Pro Gly Asn Ser
            100                 105                 110

Leu Tyr Tyr Ser Lys Val Val Ile Tyr Asn Asp Thr Asp Lys Arg Ala
        115                 120                 125

Phe Val Thr Gly Tyr Asn Leu
    130                 135

<210> SEQ ID NO 3
<211> LENGTH: 429
<212> TYPE: PRT
<213> ORGANISM: Xenorhabdus nematophilus
```

<400> SEQUENCE: 3

```
Met Asn Asn Glu Pro Met Asn Thr Asn Glu Ser Gln Ala Ser Glu Ile
 1               5                  10                  15
Val Pro Ser Met Asn Glu Ser Ile Leu Ala Ala Pro Tyr Ser Ile Ser
            20                  25                  30
Thr Pro Asn Tyr Glu Trp Asp Met Ser Ile Ile Lys Asp Ala Ile
        35                  40                  45
Ile Gly Gly Ile Gly Phe Ile Pro Gly Pro Gly Ser Ala Ile Ser Phe
     50                  55                  60
Leu Leu Gly Leu Phe Trp Pro Gln Gln Thr Asp Asn Thr Trp Glu Gln
 65                  70                  75                  80
Ile Leu Gln Lys Val Glu Gln Met Ile Glu Gln Ala Asn Leu Lys Thr
            85                  90                  95
Ile Gln Gly Ile Leu Asn Gly Asp Ile Gln Glu Ile Lys Gly Lys Met
        100                 105                 110
Glu His Val Gln Phe Met Leu Glu Ser Ser Pro Gly Thr Gln Glu Ser
        115                 120                 125
His Asp Ala Tyr Met Phe Leu Ala Arg Tyr Leu Val Ser Ile Asp Glu
        130                 135                 140
Lys Phe Lys Ser Phe Asp Asn Lys Thr Asn Tyr Gln Ile Leu Pro Met
145                 150                 155                 160
Tyr Thr Asn Thr Ile Met Leu Gln Ala Pro Tyr Trp Lys Met Gly Ile
            165                 170                 175
Glu Arg Lys Asp Glu Ile Lys Leu Thr Asp Ile Glu Val Asn Glu Leu
        180                 185                 190
Lys Glu Leu Ile Gly Lys Leu Ser Thr Ser Ala Asp Lys Tyr Ile His
        195                 200                 205
Asp Val Tyr Thr Arg Glu Tyr Asp Asn Ala Met Asn Thr Ser Thr Ala
        210                 215                 220
Ala Asn Ile Thr Asn Asn Leu Leu Ser Val Arg Gly Tyr Cys Leu Leu
225                 230                 235                 240
His Gly Leu Glu Cys Leu Glu Val Ile Asn His Ile Gln Asn Asn Ser
            245                 250                 255
Leu Glu Gln Ser Phe Tyr Pro Lys Thr Ile Ser Tyr Ser Thr Val Phe
        260                 265                 270
Asp Arg Gln Thr Asn Lys Thr Arg Val Gln Ala Leu Thr Glu Asp Asp
        275                 280                 285
Gln Met Gln Glu Pro Phe Lys Pro Ala Leu Ile Asn Gly Lys Tyr Asn
        290                 295                 300
Lys Ile Lys Ser Leu Ile Gly Tyr Val Gln Arg Ile Gly Asn Ala Pro
305                 310                 315                 320
Arg Val Gly Gly Ile Lys Val Thr Phe Ala Asn Asp Ala Ser Tyr Thr
            325                 330                 335
Leu Gly Thr Val Thr Ser Glu Val Asn Ser Ile Glu Leu Asn Asp Ser
        340                 345                 350
Val Ile Thr Ser Leu Glu Val Trp Gly Asn Gly Ala Ile Asp Glu Ala
        355                 360                 365
Phe Phe Thr Leu Ser Asp Gly Arg Gln Phe Arg Leu Gly Gln Arg Tyr
        370                 375                 380
Ala Ser Asn Tyr Arg Lys Tyr Ala Val Asp Asn His Tyr Ile Ser Gly
385                 390                 395                 400
```

Leu Tyr Leu Ala Ser Asp Glu Pro Ser Leu Ala Gly Gln Ala Ala Gly
                405                 410                 415

Ile Ala Val Ser Tyr His Met Ile Ala Asp Lys Lys Ser
            420                 425

<210> SEQ ID NO 4
<211> LENGTH: 408
<212> TYPE: DNA
<213> ORGANISM: Xenorhabdus nematophilus
<220> FEATURE:
<221> NAME/KEY: CDS
<222> LOCATION: (1)..(405)
<223> OTHER INFORMATION: orf3 of pCIB9381

<400> SEQUENCE: 4

```
atg att aca atc aat atc act ggt gat aat gta aga gtt aat aac aat      48
Met Ile Thr Ile Asn Ile Thr Gly Asp Asn Val Arg Val Asn Asn Asn
  1               5                  10                  15 ata gca aca gaa acc gac ctc caa aat aca cct gct tca gca ccc tta      96
Ile Ala Thr Glu Thr Asp Leu Gln Asn Thr Pro Ala Ser Ala Pro Leu
             20                  25                  30 tca att att aat ttt agg gat atg aca ata gaa cct cat tca tct gtt     144
Ser Ile Ile Asn Phe Arg Asp Met Thr Ile Glu Pro His Ser Ser Val
         35                  40                  45 gag gcg ata aga acc gat aca ccg att att cct gaa tca cga cca aat     192
Glu Ala Ile Arg Thr Asp Thr Pro Ile Ile Pro Glu Ser Arg Pro Asn
     50                  55                  60 tac tat gtt gct aat tct ggc ccg gcc tca tca gtc aga gct gtt ttc     240
Tyr Tyr Val Ala Asn Ser Gly Pro Ala Ser Ser Val Arg Ala Val Phe
 65                  70                  75                  80 tat tgg tcc cac tct ttt aca tca gaa tgg ttt gaa tct tcc tct att     288
Tyr Trp Ser His Ser Phe Thr Ser Glu Trp Phe Glu Ser Ser Ser Ile
                 85                  90                  95 att gta aaa gca ggc gaa gac gga gtc tta cat tca ccg ggt aat tct     336
Ile Val Lys Ala Gly Glu Asp Gly Val Leu His Ser Pro Gly Asn Ser
            100                 105                 110 tta tat tac agc aag gtt gta att tat aac gat aca gac aaa cgt gct     384
Leu Tyr Tyr Ser Lys Val Val Ile Tyr Asn Asp Thr Asp Lys Arg Ala
        115                 120                 125 ttt gtt acc ggc tac aat cta taa                                     408
Phe Val Thr Gly Tyr Asn Leu
    130                 135
```

<210> SEQ ID NO 5
<211> LENGTH: 135
<212> TYPE: PRT
<213> ORGANISM: Xenorhabdus nematophilus

<400> SEQUENCE: 5

Met Ile Thr Ile Asn Ile Thr Gly Asp Asn Val Arg Val Asn Asn Asn
  1               5                  10                  15

Ile Ala Thr Glu Thr Asp Leu Gln Asn Thr Pro Ala Ser Ala Pro Leu
             20                  25                  30

Ser Ile Ile Asn Phe Arg Asp Met Thr Ile Glu Pro His Ser Ser Val
         35                  40                  45

Glu Ala Ile Arg Thr Asp Thr Pro Ile Ile Pro Glu Ser Arg Pro Asn
     50                  55                  60

Tyr Tyr Val Ala Asn Ser Gly Pro Ala Ser Ser Val Arg Ala Val Phe
 65                  70                  75                  80

```
Tyr Trp Ser His Ser Phe Thr Ser Glu Trp Phe Glu Ser Ser Ser Ile
             85                  90                  95
Ile Val Lys Ala Gly Glu Asp Gly Val Leu His Ser Pro Gly Asn Ser
        100                 105                 110
Leu Tyr Tyr Ser Lys Val Val Ile Tyr Asn Asp Thr Asp Lys Arg Ala
    115                 120                 125
Phe Val Thr Gly Tyr Asn Leu
130                 135

<210> SEQ ID NO 6
<211> LENGTH: 1290
<212> TYPE: DNA
<213> ORGANISM: Xenorhabdus nematophilus
<220> FEATURE:
<221> NAME/KEY: CDS
<222> LOCATION: (1)..(1287)
<223> OTHER INFORMATION: JHE-like orf2 of pCIB9381

<400> SEQUENCE: 6 atg aat aat gaa ccg atg aat act aat gaa tca caa gtt tca gag ata      48
Met Asn Asn Glu Pro Met Asn Thr Asn Glu Ser Gln Val Ser Glu Ile
 1               5                  10                  15 gta ccc tca atg aat gaa tct ata tta gca gca cct tat tca att tct      96
Val Pro Ser Met Asn Glu Ser Ile Leu Ala Ala Pro Tyr Ser Ile Ser
             20                  25                  30 aca cct aat tat gaa tgg gat atg tca tca ata ata aaa gat gcc att     144
Thr Pro Asn Tyr Glu Trp Asp Met Ser Ser Ile Ile Lys Asp Ala Ile
         35                  40                  45 att ggt ggt ata ggc ttt att cct ggt ccg ggc tca gca ata tca ttt     192
Ile Gly Gly Ile Gly Phe Ile Pro Gly Pro Gly Ser Ala Ile Ser Phe
     50                  55                  60 ttg tta ggg tta ttt tgg cca caa caa acc gac aat act tgg gag caa     240
Leu Leu Gly Leu Phe Trp Pro Gln Gln Thr Asp Asn Thr Trp Glu Gln
 65                  70                  75                  80 att ctc caa aaa gta gaa caa atg atc gag caa gcc aat ctc aaa act     288
Ile Leu Gln Lys Val Glu Gln Met Ile Glu Gln Ala Asn Leu Lys Thr
                 85                  90                  95 att caa gga ata ttg aac ggc gat ata caa gaa att aaa ggc aaa atg     336
Ile Gln Gly Ile Leu Asn Gly Asp Ile Gln Glu Ile Lys Gly Lys Met
            100                 105                 110 gaa cat gtg caa ttc atg cta gaa tcc tca cct ggc act caa gaa agc     384
Glu His Val Gln Phe Met Leu Glu Ser Ser Pro Gly Thr Gln Glu Ser
        115                 120                 125 cat gac gca tac atg ttt ctg gcg aga tat ctg gtc agt ata gac gaa     432
His Asp Ala Tyr Met Phe Leu Ala Arg Tyr Leu Val Ser Ile Asp Glu
    130                 135                 140 aaa ttc aag tct ttt gat aac aaa aca aat tat caa att ctt ccc atg     480
Lys Phe Lys Ser Phe Asp Asn Lys Thr Asn Tyr Gln Ile Leu Pro Met
145                 150                 155                 160 tat acc aat acg att atg tta caa gcc cct tat tgg aaa atg ggt ata     528
Tyr Thr Asn Thr Ile Met Leu Gln Ala Pro Tyr Trp Lys Met Gly Ile
                165                 170                 175 gag aga aaa gat gag ata aaa cta aca gat ata gaa gtt aat gaa tta     576
Glu Arg Lys Asp Glu Ile Lys Leu Thr Asp Ile Glu Val Asn Glu Leu
            180                 185                 190 aaa gag ctg ata gga aaa tta tct acc agc gcc gat aaa tat att cat     624
Lys Glu Leu Ile Gly Lys Leu Ser Thr Ser Ala Asp Lys Tyr Ile His
        195                 200                 205
```

```
gat gtc tat act cgt gaa tat gat aat gcg atg aac act tca aca gca      672
Asp Val Tyr Thr Arg Glu Tyr Asp Asn Ala Met Asn Thr Ser Thr Ala
210                 215                 220 gca aat atc acc aat aat tta tct gta aga ggc tat tgt tta tta          720
Ala Asn Ile Thr Asn Asn Leu Leu Ser Val Arg Gly Tyr Cys Leu Leu
225                 230                 235                 240 cat ggt tta gaa tgt ctc gaa gtc att aac cat ata caa aat aat agc      768
His Gly Leu Glu Cys Leu Glu Val Ile Asn His Ile Gln Asn Asn Ser
            245                 250                 255 ctt gag caa agt ttt tat cct aaa act atc agc tac tcc acc gta ttc      816
Leu Glu Gln Ser Phe Tyr Pro Lys Thr Ile Ser Tyr Ser Thr Val Phe
        260                 265                 270 gat cgc cag aca aat aaa aca agg gtt caa gcc ctg aca gaa gac gat      864
Asp Arg Gln Thr Asn Lys Thr Arg Val Gln Ala Leu Thr Glu Asp Asp
    275                 280                 285 caa atg caa gag cca ttc aag cct gct tta att aat ggg aag tac aac      912
Gln Met Gln Glu Pro Phe Lys Pro Ala Leu Ile Asn Gly Lys Tyr Asn
290                 295                 300 aaa ata aaa tca ttg att ggg tat gta caa aga atc gga aac gca ccc      960
Lys Ile Lys Ser Leu Ile Gly Tyr Val Gln Arg Ile Gly Asn Ala Pro
305                 310                 315                 320 aga gtt gga ggc att aaa gtc aca ttt gca aac gat gca tct tat acc     1008
Arg Val Gly Gly Ile Lys Val Thr Phe Ala Asn Asp Ala Ser Tyr Thr
            325                 330                 335 ctc ggt aca gta act tca gaa gta aac tca att gaa ctg aat gac agc     1056
Leu Gly Thr Val Thr Ser Glu Val Asn Ser Ile Glu Leu Asn Asp Ser
        340                 345                 350 gtt ata acc agc ctg gaa gta tgg gga aat ggc gct gtt gat gag gca     1104
Val Ile Thr Ser Leu Glu Val Trp Gly Asn Gly Ala Val Asp Glu Ala
    355                 360                 365 ttc ttt aca tta agt gac gga cgt caa ttt agg ctt ggc caa cgc tat     1152
Phe Phe Thr Leu Ser Asp Gly Arg Gln Phe Arg Leu Gly Gln Arg Tyr
370                 375                 380 gcc agt aac tat aga aaa tat gct gtc gat aac cac tat att tca gga     1200
Ala Ser Asn Tyr Arg Lys Tyr Ala Val Asp Asn His Tyr Ile Ser Gly
385                 390                 395                 400 ttg tac tta gcc agt gat gaa cct tca ttg gca ggt caa gca gca ggc     1248
Leu Tyr Leu Ala Ser Asp Glu Pro Ser Leu Ala Gly Gln Ala Ala Gly
            405                 410                 415 att gca gtt tca tac cat atg ata gct gat aaa aaa tca tag             1290
Ile Ala Val Ser Tyr His Met Ile Ala Asp Lys Lys Ser
        420                 425
```

<210> SEQ ID NO 7
<211> LENGTH: 429
<212> TYPE: PRT
<213> ORGANISM: Xenorhabdus nematophilus

<400> SEQUENCE: 7

```
Met Asn Asn Glu Pro Met Asn Thr Asn Glu Ser Gln Val Ser Glu Ile
 1               5                   10                  15

Val Pro Ser Met Asn Glu Ser Ile Leu Ala Ala Pro Tyr Ser Ile Ser
            20                  25                  30

Thr Pro Asn Tyr Glu Trp Asp Met Ser Ser Ile Ile Lys Asp Ala Ile
        35                  40                  45

Ile Gly Gly Ile Gly Phe Ile Pro Gly Pro Gly Ser Ala Ile Ser Phe
    50                  55                  60

Leu Leu Gly Leu Phe Trp Pro Gln Gln Thr Asp Asn Thr Trp Glu Gln
65                  70                  75                  80
```

Ile Leu Gln Lys Val Glu Gln Met Ile Glu Gln Ala Asn Leu Lys Thr
              85                  90                  95

Ile Gln Gly Ile Leu Asn Gly Asp Ile Gln Glu Ile Lys Gly Lys Met
            100                 105                 110

Glu His Val Gln Phe Met Leu Glu Ser Ser Pro Gly Thr Gln Glu Ser
        115                 120                 125

His Asp Ala Tyr Met Phe Leu Ala Arg Tyr Leu Val Ser Ile Asp Glu
    130                 135                 140

Lys Phe Lys Ser Phe Asp Asn Lys Thr Asn Tyr Gln Ile Leu Pro Met
145                 150                 155                 160

Tyr Thr Asn Thr Ile Met Leu Gln Ala Pro Tyr Trp Lys Met Gly Ile
            165                 170                 175

Glu Arg Lys Asp Glu Ile Lys Leu Thr Asp Ile Glu Val Asn Glu Leu
        180                 185                 190

Lys Glu Leu Ile Gly Lys Leu Ser Thr Ser Ala Asp Lys Tyr Ile His
    195                 200                 205

Asp Val Tyr Thr Arg Glu Tyr Asp Asn Ala Met Asn Thr Ser Thr Ala
210                 215                 220

Ala Asn Ile Thr Asn Asn Leu Leu Ser Val Arg Gly Tyr Cys Leu Leu
225                 230                 235                 240

His Gly Leu Glu Cys Leu Glu Val Ile Asn His Ile Gln Asn Asn Ser
            245                 250                 255

Leu Glu Gln Ser Phe Tyr Pro Lys Thr Ile Ser Tyr Ser Thr Val Phe
        260                 265                 270

Asp Arg Gln Thr Asn Lys Thr Arg Val Gln Ala Leu Thr Glu Asp Asp
    275                 280                 285

Gln Met Gln Glu Pro Phe Lys Pro Ala Leu Ile Asn Gly Lys Tyr Asn
290                 295                 300

Lys Ile Lys Ser Leu Ile Gly Tyr Val Gln Arg Ile Gly Asn Ala Pro
305                 310                 315                 320

Arg Val Gly Gly Ile Lys Val Thr Phe Ala Asn Asp Ala Ser Tyr Thr
            325                 330                 335

Leu Gly Thr Val Thr Ser Glu Val Asn Ser Ile Glu Leu Asn Asp Ser
        340                 345                 350

Val Ile Thr Ser Leu Glu Val Trp Gly Asn Gly Ala Val Asp Glu Ala
    355                 360                 365

Phe Phe Thr Leu Ser Asp Gly Arg Gln Phe Arg Leu Gly Gln Arg Tyr
370                 375                 380

Ala Ser Asn Tyr Arg Lys Tyr Ala Val Asp Asn His Tyr Ile Ser Gly
385                 390                 395                 400

Leu Tyr Leu Ala Ser Asp Glu Pro Ser Leu Ala Gly Gln Ala Ala Gly
            405                 410                 415

Ile Ala Val Ser Tyr His Met Ile Ala Asp Lys Lys Ser
        420                 425

<210> SEQ ID NO 8
<211> LENGTH: 408
<212> TYPE: DNA
<213> ORGANISM: Xenorhabdus poinarii
<220> FEATURE:
<221> NAME/KEY: CDS
<222> LOCATION: (1)..(405)
<223> OTHER INFORMATION: orf1 of pCIB9354

<400> SEQUENCE: 8

```
atg atc aca atc aat atc agt ggt ggt aat gta aca att aat aac aat    48
Met Ile Thr Ile Asn Ile Ser Gly Gly Asn Val Thr Ile Asn Asn Asn
  1               5                  10                  15 atc agt tca gta acg gat atc caa aaa ccc ctt gat gca gaa ccc ctc    96
Ile Ser Ser Val Thr Asp Ile Gln Lys Pro Leu Asp Ala Glu Pro Leu
             20                  25                  30 tca gtc acg aat tat aga gat ctg aca ata gag ccg cac tca tct att   144
Ser Val Thr Asn Tyr Arg Asp Leu Thr Ile Glu Pro His Ser Ser Ile
         35                  40                  45 caa gca gac aga acg gac acc ccc att att cct gaa aca cgc cct gat   192
Gln Ala Asp Arg Thr Asp Thr Pro Ile Ile Pro Glu Thr Arg Pro Asp
     50                  55                  60 tat tat atc gct aac tca ggc cct gct tca tca gtc aaa gct gtg ttt   240
Tyr Tyr Ile Ala Asn Ser Gly Pro Ala Ser Ser Val Lys Ala Val Phe
 65                  70                  75                  80 tat tgg tcg cat tcg ttt aca tcg gaa tgg ttc gag tat tca tct atc   288
Tyr Trp Ser His Ser Phe Thr Ser Glu Trp Phe Glu Tyr Ser Ser Ile
                 85                  90                  95 acg gta aaa gca gga gaa gat gga ata tta aaa tca ccg agt aat gct   336
Thr Val Lys Ala Gly Glu Asp Gly Ile Leu Lys Ser Pro Ser Asn Ala
            100                 105                 110 gta tat tac agt aaa gta gtc att tat aat gat aca gat aag cgg gct   384
Val Tyr Tyr Ser Lys Val Val Ile Tyr Asn Asp Thr Asp Lys Arg Ala
        115                 120                 125 ttt gtg act gga tat aac atg taa                                   408
Phe Val Thr Gly Tyr Asn Met
    130                 135

<210> SEQ ID NO 9
<211> LENGTH: 135
<212> TYPE: PRT
<213> ORGANISM: Xenorhabdus poinarii

<400> SEQUENCE: 9

Met Ile Thr Ile Asn Ile Ser Gly Gly Asn Val Thr Ile Asn Asn Asn
  1               5                  10                  15

Ile Ser Ser Val Thr Asp Ile Gln Lys Pro Leu Asp Ala Glu Pro Leu
             20                  25                  30

Ser Val Thr Asn Tyr Arg Asp Leu Thr Ile Glu Pro His Ser Ser Ile
         35                  40                  45

Gln Ala Asp Arg Thr Asp Thr Pro Ile Ile Pro Glu Thr Arg Pro Asp
     50                  55                  60

Tyr Tyr Ile Ala Asn Ser Gly Pro Ala Ser Ser Val Lys Ala Val Phe
 65                  70                  75                  80

Tyr Trp Ser His Ser Phe Thr Ser Glu Trp Phe Glu Tyr Ser Ser Ile
                 85                  90                  95

Thr Val Lys Ala Gly Glu Asp Gly Ile Leu Lys Ser Pro Ser Asn Ala
            100                 105                 110

Val Tyr Tyr Ser Lys Val Val Ile Tyr Asn Asp Thr Asp Lys Arg Ala
        115                 120                 125

Phe Val Thr Gly Tyr Asn Met
    130                 135

<210> SEQ ID NO 10
<211> LENGTH: 1056
<212> TYPE: DNA
<213> ORGANISM: Xenorhabdus poinarii
<220> FEATURE:
<221> NAME/KEY: CDS
<222> LOCATION: (1)..(1053)
```

<223> OTHER INFORMATION: JHE-like orf2 of pCIB9354

<400> SEQUENCE: 10

```
atg aat aat agt cca atg aat gat cag tta tca aca gcg cct tat tca      48
Met Asn Asn Ser Pro Met Asn Asp Gln Leu Ser Thr Ala Pro Tyr Ser
  1               5                  10                  15 att tcg aca ccc aat tat gaa tgg gat atg tca tca atc ata aaa gat      96
Ile Ser Thr Pro Asn Tyr Glu Trp Asp Met Ser Ser Ile Ile Lys Asp
             20                  25                  30 gcc att atc ggt ggc ata gga ttt att ccc gga cca ggc cct gca atc     144
Ala Ile Ile Gly Gly Ile Gly Phe Ile Pro Gly Pro Gly Pro Ala Ile
         35                  40                  45 tct ttt tta tta gga ctg ttc tgg cca caa cag aca gac aat acc tgg     192
Ser Phe Leu Leu Gly Leu Phe Trp Pro Gln Gln Thr Asp Asn Thr Trp
     50                  55                  60 gat caa atc ctc caa aaa atc gaa caa atg ata gaa gaa gcg aat tta     240
Asp Gln Ile Leu Gln Lys Ile Glu Gln Met Ile Glu Glu Ala Asn Leu
 65                  70                  75                  80 aaa acc att aaa ggt ata tta aat gga gat ata caa gaa att aaa gga     288
Lys Thr Ile Lys Gly Ile Leu Asn Gly Asp Ile Gln Glu Ile Lys Gly
                 85                  90                  95 aaa atg gac cat gtg aaa tct atg cta gag aat tct cct ggc agc cag     336
Lys Met Asp His Val Lys Ser Met Leu Glu Asn Ser Pro Gly Ser Gln
            100                 105                 110 gaa agc cat gat gct tat atg ttt ctg gca agg ttt ttg gtc agt att     384
Glu Ser His Asp Ala Tyr Met Phe Leu Ala Arg Phe Leu Val Ser Ile
        115                 120                 125 gat gaa aaa ttc aaa tct ttc gat gat aga acc aat tat caa att ctt     432
Asp Glu Lys Phe Lys Ser Phe Asp Asp Arg Thr Asn Tyr Gln Ile Leu
    130                 135                 140 ccc atg tac acg aat aca att atg tta caa gcg cct tat tgg aaa atg     480
Pro Met Tyr Thr Asn Thr Ile Met Leu Gln Ala Pro Tyr Trp Lys Met
145                 150                 155                 160 ggc atc gaa aag aaa gag gat atc ggt tta acc gat att gaa gtt ggt     528
Gly Ile Glu Lys Lys Glu Asp Ile Gly Leu Thr Asp Ile Glu Val Gly
                165                 170                 175 gaa tta aaa gaa ctt atc gat aaa tta tat act aaa tca tat gat tat     576
Glu Leu Lys Glu Leu Ile Asp Lys Leu Tyr Thr Lys Ser Tyr Asp Tyr
            180                 185                 190 atc aat aat acg tat aat cgt gaa tat aat aat gca atc aat acg tca     624
Ile Asn Asn Thr Tyr Asn Arg Glu Tyr Asn Asn Ala Ile Asn Thr Ser
        195                 200                 205 acc gca gag agt atc acc aat aat tta ttg tct gtc aga gga tat tgt     672
Thr Ala Glu Ser Ile Thr Asn Asn Leu Leu Ser Val Arg Gly Tyr Cys
    210                 215                 220 tta tta cat ggt tgt gaa tgc ctt gaa gtt att gcg cat ata caa aac     720
Leu Leu His Gly Cys Glu Cys Leu Glu Val Ile Ala His Ile Gln Asn
225                 230                 235                 240 aat agt ctt gat aaa ggc ttc tac cct aaa acg atc agc tat tcg agt     768
Asn Ser Leu Asp Lys Gly Phe Tyr Pro Lys Thr Ile Ser Tyr Ser Ser
                245                 250                 255 gtt ttc gat cgt cct aca aac aaa atg aga att cag gcg ctt aca gaa     816
Val Phe Asp Arg Pro Thr Asn Lys Met Arg Ile Gln Ala Leu Thr Glu
            260                 265                 270 gat gac caa atg caa gaa ccg ttc aaa cct tct ttc gtc aat ggt caa     864
Asp Asp Gln Met Gln Glu Pro Phe Lys Pro Ser Phe Val Asn Gly Gln
        275                 280                 285 tat aat aaa ata aaa tca ttg gag ggt tat gtc aca agg atc ggc aat     912
Tyr Asn Lys Ile Lys Ser Leu Glu Gly Tyr Val Thr Arg Ile Gly Asn
    290                 295                 300
```

```
gcc ccc cga gtc ggc gga att aaa atc aca ttt gaa aac aac gca tct     960
Ala Pro Arg Val Gly Gly Ile Lys Ile Thr Phe Glu Asn Asn Ala Ser
305                 310                 315                 320 tat act ctt ggc act gta act tca gaa aca acc tct att gaa ctc aat    1008
Tyr Thr Leu Gly Thr Val Thr Ser Glu Thr Thr Ser Ile Glu Leu Asn
                325                 330                 335 gag agt gtt ata acc agc ata gaa gtg tgg gga gag tgg tgc cgt tga    1056
Glu Ser Val Ile Thr Ser Ile Glu Val Trp Gly Glu Trp Cys Arg
            340                 345                 350
```

<210> SEQ ID NO 11
<211> LENGTH: 351
<212> TYPE: PRT
<213> ORGANISM: Xenorhabdus poinarii

<400> SEQUENCE: 11

```
Met Asn Asn Ser Pro Met Asn Asp Gln Leu Ser Thr Ala Pro Tyr Ser
 1               5                  10                  15

Ile Ser Thr Pro Asn Tyr Glu Trp Asp Met Ser Ser Ile Ile Lys Asp
            20                  25                  30

Ala Ile Ile Gly Gly Ile Gly Phe Ile Pro Gly Pro Gly Pro Ala Ile
        35                  40                  45

Ser Phe Leu Leu Gly Leu Phe Trp Pro Gln Gln Thr Asp Asn Thr Trp
    50                  55                  60

Asp Gln Ile Leu Gln Lys Ile Glu Gln Met Ile Glu Ala Asn Leu
65                  70                  75                  80

Lys Thr Ile Lys Gly Ile Leu Asn Gly Asp Ile Gln Glu Ile Lys Gly
                85                  90                  95

Lys Met Asp His Val Lys Ser Met Leu Glu Asn Ser Pro Gly Ser Gln
            100                 105                 110

Glu Ser His Asp Ala Tyr Met Phe Leu Ala Arg Phe Leu Val Ser Ile
        115                 120                 125

Asp Glu Lys Phe Lys Ser Phe Asp Asp Arg Thr Asn Tyr Gln Ile Leu
    130                 135                 140

Pro Met Tyr Thr Asn Thr Ile Met Leu Gln Ala Pro Tyr Trp Lys Met
145                 150                 155                 160

Gly Ile Glu Lys Lys Glu Asp Ile Gly Leu Thr Asp Ile Glu Val Gly
                165                 170                 175

Glu Leu Lys Glu Leu Ile Asp Lys Leu Tyr Thr Lys Ser Tyr Asp Tyr
            180                 185                 190

Ile Asn Asn Thr Tyr Asn Arg Glu Tyr Asn Asn Ala Ile Asn Thr Ser
        195                 200                 205

Thr Ala Glu Ser Ile Thr Asn Asn Leu Leu Ser Val Arg Gly Tyr Cys
    210                 215                 220

Leu Leu His Gly Cys Glu Cys Leu Glu Val Ile Ala His Ile Gln Asn
225                 230                 235                 240

Asn Ser Leu Asp Lys Gly Phe Tyr Pro Lys Thr Ile Ser Tyr Ser Ser
                245                 250                 255

Val Phe Asp Arg Pro Thr Asn Lys Met Arg Ile Gln Ala Leu Thr Glu
            260                 265                 270

Asp Asp Gln Met Gln Glu Pro Phe Lys Pro Ser Phe Val Asn Gly Gln
        275                 280                 285

Tyr Asn Lys Ile Lys Ser Leu Glu Gly Tyr Val Thr Arg Ile Gly Asn
    290                 295                 300
```

```
Ala Pro Arg Val Gly Gly Ile Lys Ile Thr Phe Glu Asn Asn Ala Ser
305                 310                 315                 320

Tyr Thr Leu Gly Thr Val Thr Ser Glu Thr Thr Ser Ile Glu Leu Asn
                325                 330                 335

Glu Ser Val Ile Thr Ser Ile Glu Val Trp Gly Glu Trp Cys Arg
            340                 345                 350
```

<210> SEQ ID NO 12
<211> LENGTH: 408
<212> TYPE: DNA
<213> ORGANISM: Photorhabdus luminescens
<220> FEATURE:
<221> NAME/KEY: CDS
<222> LOCATION: (1)..(405)
<223> OTHER INFORMATION: orf1 of pCIB9383-21

<400> SEQUENCE: 12

```
atg att aca atc aat atc act ggt gat aat gta aga gtt aat aac aat     48
Met Ile Thr Ile Asn Ile Thr Gly Asp Asn Val Arg Val Asn Asn Asn
  1               5                  10                  15 ata gca aca gaa acc gac ctc caa aat aca cct gct tca gca ccc tta     96
Ile Ala Thr Glu Thr Asp Leu Gln Asn Thr Pro Ala Ser Ala Pro Leu
             20                  25                  30 tca att att aat ttt agg gat atg aca ata gaa cct cat tca tct gtt    144
Ser Ile Ile Asn Phe Arg Asp Met Thr Ile Glu Pro His Ser Ser Val
         35                  40                  45 gag gcg ata aga acc gat aca ccg att att cct gaa tca cga cca aat    192
Glu Ala Ile Arg Thr Asp Thr Pro Ile Ile Pro Glu Ser Arg Pro Asn
     50                  55                  60 tac tat gtt gct aat tct ggc ccg gcc tca gtc aga gct gtt ttc        240
Tyr Tyr Val Ala Asn Ser Gly Pro Ala Ser Ser Val Arg Ala Val Phe
 65                  70                  75                  80 tat tgg tcc cac tct ttt aca tca gaa tgg ttt gaa tct tcc tct att    288
Tyr Trp Ser His Ser Phe Thr Ser Glu Trp Phe Glu Ser Ser Ser Ile
                 85                  90                  95 att gta aaa gca ggc gaa gac gga gtc tta cat tca ccg ggt aat tct    336
Ile Val Lys Ala Gly Glu Asp Gly Val Leu His Ser Pro Gly Asn Ser
            100                 105                 110 tta tat tac agc aag gtt gta att tat aac gat aca gac aaa cgt gct    384
Leu Tyr Tyr Ser Lys Val Val Ile Tyr Asn Asp Thr Asp Lys Arg Ala
        115                 120                 125 ttt gtt acc ggc tac aat cta taa                                    408
Phe Val Thr Gly Tyr Asn Leu
    130                 135
```

<210> SEQ ID NO 13
<211> LENGTH: 135
<212> TYPE: PRT
<213> ORGANISM: Photorhabdus luminescens

<400> SEQUENCE: 13

```
Met Ile Thr Ile Asn Ile Thr Gly Asp Asn Val Arg Val Asn Asn Asn
  1               5                  10                  15

Ile Ala Thr Glu Thr Asp Leu Gln Asn Thr Pro Ala Ser Ala Pro Leu
             20                  25                  30

Ser Ile Ile Asn Phe Arg Asp Met Thr Ile Glu Pro His Ser Ser Val
         35                  40                  45

Glu Ala Ile Arg Thr Asp Thr Pro Ile Ile Pro Glu Ser Arg Pro Asn
     50                  55                  60
```

```
Tyr Tyr Val Ala Asn Ser Gly Pro Ala Ser Ser Val Arg Ala Val Phe
 65                  70                  75                  80

Tyr Trp Ser His Ser Phe Thr Ser Glu Trp Phe Glu Ser Ser Ser Ile
             85                   90                   95

Ile Val Lys Ala Gly Glu Asp Gly Val Leu His Ser Pro Gly Asn Ser
        100                 105                 110

Leu Tyr Tyr Ser Lys Val Val Ile Tyr Asn Asp Thr Asp Lys Arg Ala
    115                 120                 125

Phe Val Thr Gly Tyr Asn Leu
130                 135

<210> SEQ ID NO 14
<211> LENGTH: 1320
<212> TYPE: DNA
<213> ORGANISM: Photorhabdus luminescens
<220> FEATURE:
<221> NAME/KEY: CDS
<222> LOCATION: (1)..(1317)
<223> OTHER INFORMATION: JHE-like orf2 of pCIB9383-21

<400> SEQUENCE: 14 atg aat aat gaa ccg atg aat act aat gaa tca caa gct tca gag ata    48
Met Asn Asn Glu Pro Met Asn Thr Asn Glu Ser Gln Ala Ser Glu Ile
  1               5                  10                  15 gta ccc tca atg aat gaa tct ata tta aat gaa tct ata tta aat gaa    96
Val Pro Ser Met Asn Glu Ser Ile Leu Asn Glu Ser Ile Leu Asn Glu
             20                  25                  30 tct ata tta gca gca cct tat tca att tct aca cct aat tat gaa tgg   144
Ser Ile Leu Ala Ala Pro Tyr Ser Ile Ser Thr Pro Asn Tyr Glu Trp
         35                  40                  45 gat atg tca tca ata ata aaa gat gcc att att ggt ggt ata ggc ttt   192
Asp Met Ser Ser Ile Ile Lys Asp Ala Ile Ile Gly Gly Ile Gly Phe
     50                  55                  60 att cct ggt ccg ggc tca gca ata tca ttt ttg tta ggg tta ttt tgg   240
Ile Pro Gly Pro Gly Ser Ala Ile Ser Phe Leu Leu Gly Leu Phe Trp
 65                  70                  75                  80 cca caa caa acc gac aat act tgg gag caa att ctc caa aaa gta gaa   288
Pro Gln Gln Thr Asp Asn Thr Trp Glu Gln Ile Leu Gln Lys Val Glu
                 85                  90                  95 caa atg atc gag caa gcc aat ctc aaa act att caa gga ata ttg aac   336
Gln Met Ile Glu Gln Ala Asn Leu Lys Thr Ile Gln Gly Ile Leu Asn
            100                 105                 110 ggc gat ata caa gaa att aaa ggc aaa atg gaa cat gtg caa ttc atg   384
Gly Asp Ile Gln Glu Ile Lys Gly Lys Met Glu His Val Gln Phe Met
        115                 120                 125 cta gaa tcc tca cct ggc act caa gaa agc cat gac gca tac atg ttt   432
Leu Glu Ser Ser Pro Gly Thr Gln Glu Ser His Asp Ala Tyr Met Phe
    130                 135                 140 ctg gcg aga tat ctg gtc agt ata gac gaa aaa ttc aag tct ttt gat   480
Leu Ala Arg Tyr Leu Val Ser Ile Asp Glu Lys Phe Lys Ser Phe Asp
145                 150                 155                 160 aac aaa aca aat tat caa att ctt ccc atg tat acc aat acg att atg   528
Asn Lys Thr Asn Tyr Gln Ile Leu Pro Met Tyr Thr Asn Thr Ile Met
                165                 170                 175 tta caa gcc cct tat tgg aaa atg ggt ata gag aga aaa gat gag ata   576
Leu Gln Ala Pro Tyr Trp Lys Met Gly Ile Glu Arg Lys Asp Glu Ile
            180                 185                 190 aaa cta aca gat ata gaa gtt aat gaa tta aaa gag ctg ata gga aaa   624
Lys Leu Thr Asp Ile Glu Val Asn Glu Leu Lys Glu Leu Ile Gly Lys
        195                 200                 205
```

```
tta tct acc agc gcc gat aaa tat att cat gat gtc tat act cgt gaa    672
Leu Ser Thr Ser Ala Asp Lys Tyr Ile His Asp Val Tyr Thr Arg Glu
        210                 215                 220 tat gat aat gcg atg aac act tca aca gca aat atc acc aat aat        720
Tyr Asp Asn Ala Met Asn Thr Ser Thr Ala Ala Asn Ile Thr Asn Asn
225                 230                 235                 240 tta tta tct gta aga ggc tat tgt tta tta cat ggt tta gaa tgt ctc    768
Leu Leu Ser Val Arg Gly Tyr Cys Leu Leu His Gly Leu Glu Cys Leu
                245                 250                 255 gaa gtc att aac cat ata caa aat agc ctt gag caa agt ttt tat        816
Glu Val Ile Asn His Ile Gln Asn Asn Ser Leu Glu Gln Ser Phe Tyr
        260                 265                 270 cct aaa act atc agc tac tcc acc gta ttc gat cgc cag aca aat aaa    864
Pro Lys Thr Ile Ser Tyr Ser Thr Val Phe Asp Arg Gln Thr Asn Lys
275                 280                 285 aca agg gtt caa gcc ctg aca gaa gac gat caa atg caa gag cca ttc    912
Thr Arg Val Gln Ala Leu Thr Glu Asp Asp Gln Met Gln Glu Pro Phe
                290                 295                 300 aag cct gct tta att aat ggg aag tac aac aaa ata aaa tca ttg att    960
Lys Pro Ala Leu Ile Asn Gly Lys Tyr Asn Lys Ile Lys Ser Leu Ile
305                 310                 315                 320 ggg tat gta caa aga atc gga aac gca ccc aga gtt gga ggc att aaa    1008
Gly Tyr Val Gln Arg Ile Gly Asn Ala Pro Arg Val Gly Gly Ile Lys
                325                 330                 335 gtc aca ttt gca aac gat gca tct tat acc ctc ggt aca gta act tca    1056
Val Thr Phe Ala Asn Asp Ala Ser Tyr Thr Leu Gly Thr Val Thr Ser
        340                 345                 350 gaa gta aac tca att gaa ctg aat gac agc gtt ata acc agc ctg gaa    1104
Glu Val Asn Ser Ile Glu Leu Asn Asp Ser Val Ile Thr Ser Leu Glu
                355                 360                 365 gta tgg gga aat ggc gct gtt gat gag gca ttc ttt aca tta agt gac    1152
Val Trp Gly Asn Gly Ala Val Asp Glu Ala Phe Phe Thr Leu Ser Asp
370                 375                 380 gga cgt caa ttt agg ctt ggc caa cgc tat gcc agt aac tat aga aaa    1200
Gly Arg Gln Phe Arg Leu Gly Gln Arg Tyr Ala Ser Asn Tyr Arg Lys
385                 390                 395                 400 tat gct gtc gat aac cac tat att tca gga ttg tac tta gcc agt gat    1248
Tyr Ala Val Asp Asn His Tyr Ile Ser Gly Leu Tyr Leu Ala Ser Asp
                405                 410                 415 gaa cct tca ttg gca ggt caa gca gca ggc att gca gtt tca tac cat    1296
Glu Pro Ser Leu Ala Gly Gln Ala Ala Gly Ile Ala Val Ser Tyr His
        420                 425                 430 atg ata gct gat aaa aaa tca tag                                    1320
Met Ile Ala Asp Lys Lys Ser
                435
```

<210> SEQ ID NO 15
<211> LENGTH: 439
<212> TYPE: PRT
<213> ORGANISM: Photorhabdus luminescens

<400> SEQUENCE: 15

```
Met Asn Asn Glu Pro Met Asn Thr Asn Glu Ser Gln Ala Ser Glu Ile
1               5                   10                  15

Val Pro Ser Met Asn Glu Ser Ile Leu Asn Glu Ser Ile Leu Asn Glu
            20                  25                  30

Ser Ile Leu Ala Ala Pro Tyr Ser Ile Ser Thr Pro Asn Tyr Glu Trp
        35                  40                  45
```

```
Asp Met Ser Ser Ile Ile Lys Asp Ala Ile Ile Gly Gly Ile Gly Phe
 50                  55                  60

Ile Pro Gly Pro Gly Ser Ala Ile Ser Phe Leu Leu Gly Leu Phe Trp
 65                  70                  75                  80

Pro Gln Gln Thr Asp Asn Thr Trp Glu Gln Ile Leu Gln Lys Val Glu
                 85                  90                  95

Gln Met Ile Glu Gln Ala Asn Leu Lys Thr Ile Gln Gly Ile Leu Asn
         100                 105                 110

Gly Asp Ile Gln Glu Ile Lys Gly Lys Met Glu His Val Gln Phe Met
         115                 120                 125

Leu Glu Ser Ser Pro Gly Thr Gln Glu Ser His Asp Ala Tyr Met Phe
 130                 135                 140

Leu Ala Arg Tyr Leu Val Ser Ile Asp Glu Lys Phe Lys Ser Phe Asp
 145                 150                 155                 160

Asn Lys Thr Asn Tyr Gln Ile Leu Pro Met Tyr Thr Asn Thr Ile Met
                 165                 170                 175

Leu Gln Ala Pro Tyr Trp Lys Met Gly Ile Glu Arg Lys Asp Glu Ile
         180                 185                 190

Lys Leu Thr Asp Ile Glu Val Asn Glu Leu Lys Glu Leu Ile Gly Lys
         195                 200                 205

Leu Ser Thr Ser Ala Asp Lys Tyr Ile His Asp Val Tyr Thr Arg Glu
 210                 215                 220

Tyr Asp Asn Ala Met Asn Thr Ser Thr Ala Ala Asn Ile Thr Asn Asn
225                 230                 235                 240

Leu Leu Ser Val Arg Gly Tyr Cys Leu Leu His Gly Leu Glu Cys Leu
                 245                 250                 255

Glu Val Ile Asn His Ile Gln Asn Asn Ser Leu Glu Gln Ser Phe Tyr
         260                 265                 270

Pro Lys Thr Ile Ser Tyr Ser Thr Val Phe Asp Arg Gln Thr Asn Lys
         275                 280                 285

Thr Arg Val Gln Ala Leu Thr Glu Asp Asp Gln Met Gln Glu Pro Phe
 290                 295                 300

Lys Pro Ala Leu Ile Asn Gly Lys Tyr Asn Lys Ile Lys Ser Leu Ile
305                 310                 315                 320

Gly Tyr Val Gln Arg Ile Gly Asn Ala Pro Arg Val Gly Gly Ile Lys
                 325                 330                 335

Val Thr Phe Ala Asn Asp Ala Ser Tyr Thr Leu Gly Thr Val Thr Ser
         340                 345                 350

Glu Val Asn Ser Ile Glu Leu Asn Asp Ser Val Ile Thr Ser Leu Glu
         355                 360                 365

Val Trp Gly Asn Gly Ala Val Asp Glu Ala Phe Phe Thr Leu Ser Asp
 370                 375                 380

Gly Arg Gln Phe Arg Leu Gly Gln Arg Tyr Ala Ser Asn Tyr Arg Lys
385                 390                 395                 400

Tyr Ala Val Asp Asn His Tyr Ile Ser Gly Leu Tyr Leu Ala Ser Asp
                 405                 410                 415

Glu Pro Ser Leu Ala Gly Gln Ala Ala Gly Ile Ala Val Ser Tyr His
         420                 425                 430

Met Ile Ala Asp Lys Lys Ser
         435
```

What is claimed is:

1. An isolated toxin that is active against insects, wherein said toxin comprises an amino acid sequence encoded by a nucleotide sequence that has a compliment that hybridize to a nucleotide sequence selected from the group consisting of nucleotide 569–979 of SEQ ID NO: 1, nucleotide 1045–2334 of SEQ ID NO: 1, SEQ ID NO: 4, SEQ ID NO: 6, SEQ ID NO: 8, SEQ ID NO: 10, SEQ ID NO: 12, and SEQ ID NO: 14 in 7% sodium dodecyl sulfate (SDS), 0.5M NaPO$_4$, 1 mM EDTA at 50° C. with washing in 0.1X SSC, 0.1% SS at 65° C.

2. A toxin according to claim 1, wherein said toxin is active against *Plutella xylostella*.

3. A toxin according to claim 1, wherein said toxin is produced by the *E. coli* strain designated as NRRL accession number B-21883.

4. A toxin according to claim 1, wherein said toxin comprises an amino acid sequence selected from the group consisting of: SEQ ID NOs:2, 3, 5, 7, 9, 11, 13, and 15.

5. A toxin according to claim 4, wherein said toxin comprises an amino acid sequence selected from the group consisting of: SEQ ID NO:2, 5, 9, and 13.

6. A toxin according to claim 4, wherein said toxin comprises an amino acid sequence selected from the group consisting of: SEQ ID NOs:3, 7, 11, and 15.

7. A composition comprising an insecticidally effective amount of a toxin according to claim 1.

8. A method of controlling an insect comprising delivering to the insect an effective amount of a toxin according to claim 1.

9. The method of claim 8, wherein the insect is *Plutella xylostella*.

10. The method of claim 9, wherein the toxin is delivered to the insect orally.

11. A toxin according to claim 1, wherein said nucleotide sequence has a compliment that hybridize to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14 in 7% sodium dodecyl sulfate (SDS), 0.5 M NaPO$_4$, 1 mM EDTA at 50° C. with washing in 0.1X SC, 0.1% SDS at 65° C.

12. A toxin according to claim 1, wherein said nucleotide sequence has a compliment that hybridizes to nucleotides 569–979 of SEQ ID NO:1, SEQ ID NO:4, SEQ ID NO:8, or SEQ ID NO:12 in 7% sodium dodecyl sulfate (SS), 0.5 M NaPO$_4$, 1 mM EDTA at 50° C. with washing in 0.1X SSC, 0.1% SS at 65° C.

13. A toxin according to claim 1, wherein said nucleotide sequence has a compliment that hybridizes to nucleotide 1045–233 of SEQ ID NO:1, EQ ID NO:6, SEQ ID NO:10, or SEQ ID NO:14 in 7% sodium dodecyl sulfate (SDS), 0.5 M NaPO$_4$, 1 mM EDTA at 50° C. with washing in 0.1X SC, 0.1% SS at 65°0 C.

* * * * *